（12）United States Patent
Decant, Jr. et al.

(10) Patent No.: US 8,267,954 B2
(45) Date of Patent: Sep. 18, 2012

(54) VASCULAR FILTER WITH SENSING CAPABILITY

(75) Inventors: Leonard J. Decant, Jr., Scottsdale, AZ (US); Robert W. Kalis, Mesa, AZ (US); David Micky Graves, Mesa, AZ (US); David G. Spilka, Phoenix, AZ (US); Avijit Mukherjee, Scottsdale, AZ (US); Daniel O. Almazan, Avondale, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 1219 days.

(21) Appl. No.: 11/051,101

(22) Filed: Feb. 4, 2005

(65) Prior Publication Data

US 2006/0178695 A1    Aug. 10, 2006

(51) Int. Cl.
*A61M 29/00* (2006.01)

(52) U.S. Cl. ........................................ 606/200

(58) Field of Classification Search ................ 606/158, 606/191, 200; 600/202, 594, 300, 301, 464, 600/465, 468, 469, 480, 485; 604/6.09
See application file for complete search history.

(56) References Cited

U.S. PATENT DOCUMENTS

| | | | |
|---|---|---|---|
| 3,540,431 A | 11/1970 | Mobin-Uddia | |
| 3,952,747 A * | 4/1976 | Kimmell, Jr. ................ | 606/195 |
| 4,000,739 A | 1/1977 | Stevens | |
| 4,282,876 A | 8/1981 | Flynn | |
| 4,283,447 A | 8/1981 | Flynn | |
| 4,411,655 A | 10/1983 | Schreck | |
| 4,419,095 A | 12/1983 | Nebergau et al. | |
| 4,425,908 A | 1/1984 | Simon | |
| 4,494,531 A | 1/1985 | Gianturco | |
| 4,586,501 A | 5/1986 | Claracq | |
| 4,588,399 A | 5/1986 | Nebergall et al. | |
| 4,590,938 A | 5/1986 | Segura et al. | |
| 4,611,594 A | 9/1986 | Grayhack et al. | |
| 4,619,246 A | 10/1986 | Molgaard-Nielsen et al. | |
| 4,643,184 A | 2/1987 | Mobin-Uddin | |
| 4,657,024 A | 4/1987 | Coneys | |

(Continued)

FOREIGN PATENT DOCUMENTS

EP    1 042 996 A2    10/2000

(Continued)

OTHER PUBLICATIONS

Authors' Abstract, "Abstracts of Current Literature", Journal of Vascular and Interventional Radiology, Mar. 2000, vol. 11, No. 3, pp. 402-407.

(Continued)

*Primary Examiner* — Kevin T Truong
*Assistant Examiner* — Jonathan Hollm
(74) *Attorney, Agent, or Firm* — Rutan & Tucker, LLP

(57) ABSTRACT

An implantable vessel filter having an integrated sensing capability for monitoring the condition of the vessel filter. In one variation, the vessel filter comprises a plurality of legs that would themselves perform as a sensor device for detecting distention, which would indicate the presence of a clot or thrombus therein. A passive electrical circuit may be implemented on the vessel filter to receive electromagnetic energy and transmit signals indicative of the condition of the implanted vessel filter. In another variation, a miniaturized sensor is adapted for measuring the strain and/or other physical parameters of the filter legs.

15 Claims, 16 Drawing Sheets

U.S. PATENT DOCUMENTS

| | | | |
|---|---|---|---|
| 4,688,553 A | 8/1987 | Metals | |
| 4,710,192 A | 12/1987 | Liotta et al. | |
| 4,722,344 A | 2/1988 | Cambron et al. | |
| 4,727,873 A | 3/1988 | Mobin-Uddin | |
| 4,781,177 A | 11/1988 | Lebigot | |
| 4,793,348 A | 12/1988 | Palmaz | |
| 4,798,591 A | 1/1989 | Okada | |
| 4,817,600 A | 4/1989 | Herms et al. | |
| 4,832,055 A | 5/1989 | Palestrant | |
| 4,838,879 A | 6/1989 | Tanabe et al. | |
| 4,857,062 A | 8/1989 | Russell | |
| 4,863,442 A | 9/1989 | De Mello et al. | |
| 4,873,978 A | 10/1989 | Ginsburg | |
| 4,886,506 A | 12/1989 | Lovgren et al. | |
| 4,898,591 A | 2/1990 | Jang et al. | |
| 4,922,905 A | 5/1990 | Strecker | |
| 4,950,227 A | 8/1990 | Savin et al. | |
| 4,957,501 A | 9/1990 | Lahille et al. | |
| 4,969,891 A | 11/1990 | Gewertz | |
| 4,990,156 A | 2/1991 | Lefebvre | |
| 5,045,072 A | 9/1991 | Castillo et al. | |
| 5,053,008 A | 10/1991 | Bajaj | |
| 5,059,205 A | 10/1991 | El-Noumou et al. | |
| 5,108,418 A | 4/1992 | Lefebvre | |
| 5,114,408 A | 5/1992 | Fleischhaker et al. | |
| 5,133,733 A | 7/1992 | Rasmussen et al. | |
| 5,147,379 A | 9/1992 | Sabbaghian et al. | |
| 5,152,777 A | 10/1992 | Goldberg et al. | |
| 5,171,232 A | 12/1992 | Castillo | |
| 5,188,616 A | 2/1993 | Nadal | |
| 5,203,776 A | 4/1993 | Durfee | |
| 5,234,416 A | 8/1993 | Macaulay et al. | |
| 5,234,458 A | 8/1993 | Metais | |
| 5,242,462 A | 9/1993 | El-Nounou et al. | |
| 5,300,086 A | 4/1994 | Gory et al. | |
| 5,304,156 A | 4/1994 | Sylvanowicz et al. | |
| 5,324,304 A | 6/1994 | Rasmussen | |
| 5,329,942 A | 7/1994 | Gunther et al. | |
| 5,344,427 A | 9/1994 | Cottenceau et al. | |
| 5,350,398 A | 9/1994 | Pavenik et al. | |
| 5,358,493 A | 10/1994 | Schweich, Jr. | |
| 5,370,657 A | 12/1994 | Irie | |
| 5,375,612 A | 12/1994 | Cottenceau et al. | |
| 5,383,887 A | 1/1995 | Nadal | |
| 5,413,586 A | 5/1995 | Dibie et al. | |
| 5,421,832 A | 6/1995 | Lefebvre | |
| 5,423,851 A | 6/1995 | Samuels | |
| 5,443,497 A | 8/1995 | Venbrux | |
| 5,485,667 A | 1/1996 | Kleshinski | |
| 5,531,788 A | 7/1996 | Dibie et al. | |
| 5,545,151 A | 8/1996 | O'Connor | |
| 5,549,576 A | 8/1996 | Patterson et al. | |
| 5,558,652 A | 9/1996 | Henke | |
| 5,581,248 A | 12/1996 | Spillman, Jr. et al. | |
| 5,601,568 A | 2/1997 | Chevillon et al. | |
| 5,601,595 A | 2/1997 | Smith | |
| 5,624,508 A | 4/1997 | Flomenblit et al. | |
| 5,626,605 A | 5/1997 | Irie | |
| 5,634,942 A | 6/1997 | Chevillon et al. | |
| 5,641,364 A | 6/1997 | Golberg et al. | |
| 5,649,906 A | 7/1997 | Gory et al. | |
| 5,669,879 A | 9/1997 | Duer | |
| 5,669,933 A | 9/1997 | Simon et al. | |
| 5,672,153 A | 9/1997 | Lax | |
| 5,672,158 A | 9/1997 | Okada et al. | |
| 5,681,347 A | 10/1997 | Cathcart et al. | |
| 5,683,411 A | 11/1997 | Kavteladze et al. | |
| 5,695,518 A | 12/1997 | Laerum | |
| 5,695,519 A | 12/1997 | Summers et al. | |
| 5,702,370 A | 12/1997 | Sylvanowicz et al. | |
| 5,704,910 A | 1/1998 | Humes | |
| 5,704,926 A | 1/1998 | Sutton | |
| 5,709,704 A | 1/1998 | Nott et al. | |
| 5,720,764 A | 2/1998 | Naderlinger | |
| 5,725,550 A | 3/1998 | Nadal | |
| 5,746,767 A | 5/1998 | Smith | |
| 5,755,790 A | 5/1998 | Chevillon et al. | |
| 5,759,192 A | 6/1998 | Saunders | |
| 5,769,816 A | 6/1998 | Barbut | |
| 5,776,162 A | 7/1998 | Kleshinski | |
| 5,780,807 A | 7/1998 | Saunders | |
| 5,800,457 A | 9/1998 | Gelbfish | |
| 5,800,515 A | 9/1998 | Nadal et al. | |
| 5,830,222 A | 11/1998 | Makower | |
| 5,836,968 A | 11/1998 | Simon et al. | |
| 5,836,969 A | 11/1998 | Kim et al. | |
| 5,853,420 A | 12/1998 | Chevillon et al. | |
| 5,893,869 A | 4/1999 | Barnhart et al. | |
| 5,897,497 A | 4/1999 | Fernandez | |
| 5,911,704 A | 6/1999 | Humes | |
| 5,919,224 A | 7/1999 | Thompson et al. | |
| 5,928,261 A | 7/1999 | Ruiz | |
| 5,951,585 A | 9/1999 | Cathcart | |
| 5,954,741 A | 9/1999 | Fox | |
| 5,968,071 A | 10/1999 | Chevillon et al. | |
| 5,972,019 A | 10/1999 | Engelson et al. | |
| 5,976,172 A | 11/1999 | Homsma et al. | |
| 5,984,947 A | 11/1999 | Smith | |
| 6,001,118 A | 12/1999 | Daniel et al. | |
| 6,007,558 A | 12/1999 | Ravenscroft et al. | |
| 6,013,093 A | 1/2000 | Nott et al. | |
| 6,036,723 A | 3/2000 | Anidjar et al. | |
| 6,051,015 A | 4/2000 | Maahs | |
| 6,053,873 A | 4/2000 | Govari et al. | |
| 6,059,814 A | 5/2000 | Ladd | |
| 6,059,825 A | 5/2000 | Hobbs et al. | |
| 6,066,158 A | 5/2000 | Engelson et al. | |
| 6,068,638 A | 5/2000 | Makower | |
| 6,071,292 A | 6/2000 | Makower et al. | |
| 6,077,880 A | 6/2000 | Castillo et al. | |
| 6,080,178 A | 6/2000 | Meglin | |
| 6,092,530 A | 7/2000 | Weissman et al. | |
| 6,099,549 A | 8/2000 | Bosma et al. | |
| 6,126,645 A | 10/2000 | Thompson | |
| 6,126,673 A | 10/2000 | Kim et al. | |
| 6,131,266 A | 10/2000 | Saunders | |
| 6,132,388 A | 10/2000 | Fleming | |
| 6,146,404 A | 11/2000 | Kim et al. | |
| 6,156,055 A | 12/2000 | Ravenscroft | |
| 6,159,225 A | 12/2000 | Makower | |
| 6,162,357 A | 12/2000 | Pakki et al. | |
| 6,165,179 A | 12/2000 | Cathcart | |
| 6,165,200 A | 12/2000 | Tsugita et al. | |
| 6,171,297 B1 | 1/2001 | Pedersen | |
| 6,190,353 B1 | 2/2001 | Makower et al. | |
| 6,193,739 B1 | 2/2001 | Chevillon et al. | |
| 6,193,748 B1 | 2/2001 | Thompson et al. | |
| 6,206,835 B1 | 3/2001 | Spillman, Jr. et al. | |
| 6,214,025 B1 | 4/2001 | Thistle et al. | |
| 6,217,600 B1 | 4/2001 | DiMatteo | |
| 6,228,052 B1 | 5/2001 | Pohndorf | |
| 6,231,516 B1 * | 5/2001 | Keilman et al. | 600/485 |
| 6,231,581 B1 | 5/2001 | Shank et al. | |
| 6,231,587 B1 | 5/2001 | Makower | |
| 6,231,588 B1 | 5/2001 | Zadno-Azizi | |
| 6,231,589 B1 | 5/2001 | Wessman et al. | |
| 6,235,045 B1 | 5/2001 | Barbut | |
| 6,241,746 B1 | 6/2001 | Bosma et al. | |
| 6,245,012 B1 | 6/2001 | Kleshinski | |
| 6,251,122 B1 | 6/2001 | Tsukernik | |
| 6,254,633 B1 | 7/2001 | Pinchuk et al. | |
| 6,258,026 B1 | 7/2001 | Ravenscroft | |
| 6,258,101 B1 | 7/2001 | Blake | |
| 6,264,671 B1 | 7/2001 | Stack et al. | |
| 6,267,776 B1 | 7/2001 | O'Connell | |
| 6,267,777 B1 | 7/2001 | Bosma et al. | |
| 6,273,900 B1 | 8/2001 | Nott et al. | |
| 6,273,901 B1 | 8/2001 | Whitcher et al. | |
| 6,283,983 B1 | 9/2001 | Makower et al. | |
| 6,287,317 B1 | 9/2001 | Makower et al. | |
| 6,290,710 B1 | 9/2001 | Cryer et al. | |
| 6,302,875 B1 | 10/2001 | Makower et al. | |
| 6,302,891 B1 | 10/2001 | Nadal | |
| 6,322,541 B2 | 11/2001 | West et al. | |
| 6,325,790 B1 | 12/2001 | Trotta | |
| 6,328,755 B1 | 12/2001 | Marshall | |
| 6,331,183 B1 | 12/2001 | Suon | |

| | | | | | | |
|---|---|---|---|---|---|---|
| 6,336,934 B1 | 1/2002 | Gilson et al. | | 6,696,667 B1 | 2/2004 | Flanagan |
| 6,342,062 B1 | 1/2002 | Suon et al. | | 6,702,834 B1 | 3/2004 | Boylan et al. |
| 6,342,063 B1 | 1/2002 | DeVries et al. | | 6,702,847 B2 | 3/2004 | DiCarlo |
| 6,383,193 B1 | 5/2002 | Cathcart | | 6,706,054 B2 | 3/2004 | Wessman et al. |
| 6,383,206 B1 | 5/2002 | Gillick et al. | | 6,716,208 B2 | 4/2004 | Humes |
| 6,391,045 B1 | 5/2002 | Kim et al. | | 6,719,717 B1 | 4/2004 | Johnson et al. |
| 6,402,771 B1 | 6/2002 | Palmer et al. | | 6,719,772 B2 | 4/2004 | Trask et al. |
| 6,416,530 B2 | 7/2002 | DeVries et al. | | 6,726,621 B2 | 4/2004 | Suon |
| 6,428,559 B1 | 8/2002 | Johnson | | 6,726,703 B2 | 4/2004 | Broome et al. |
| 6,432,127 B1 | 8/2002 | Kim et al. | | 6,730,108 B2 | 5/2004 | Van Tassel et al. |
| 6,436,121 B1 | 8/2002 | Blom | | 6,736,842 B2 | 5/2004 | Healy et al. |
| 6,440,077 B1 | 8/2002 | Jung et al. | | 6,755,846 B1 | 6/2004 | Yadav |
| 6,442,413 B1 | 8/2002 | Silver | | 6,761,732 B2 | 7/2004 | Burkett et al. |
| 6,443,971 B1 | 9/2002 | Boylan et al. | | 6,773,448 B2 | 8/2004 | Kusleika et al. |
| 6,443,972 B1 | 9/2002 | Bosma et al. | | 6,776,770 B1 | 8/2004 | Trerotola |
| 6,447,530 B1 | 9/2002 | Ostrovsky et al. | | 6,776,774 B2 | 8/2004 | Tansey, Jr. et al. |
| 6,458,145 B1 | 10/2002 | Ravenscroft et al. | | 6,783,538 B2 | 8/2004 | McGuckin, Jr. et al. |
| 6,468,290 B1 | 10/2002 | Weldon et al. | | 6,792,979 B2 | 9/2004 | Konya et al. |
| 6,482,222 B1 | 11/2002 | Bruckheimer et al. | | 6,793,665 B2 | 9/2004 | McGuckin, Jr. et al. |
| 6,485,500 B1 | 11/2002 | Kokish et al. | | 6,818,006 B2 | 11/2004 | Douk et al. |
| 6,485,501 B1 | 11/2002 | Green | | 6,840,950 B2 | 1/2005 | Stanford et al. |
| 6,485,502 B2 | 11/2002 | Don Michael et al. | | 6,843,798 B2 | 1/2005 | Kusleika et al. |
| 6,488,662 B2 | 12/2002 | Sirimanne | | 6,849,061 B2 | 2/2005 | Wagner |
| 6,497,709 B1 | 12/2002 | Heath | | 6,872,217 B2 | 3/2005 | Walak et al. |
| 6,506,205 B2 | 1/2003 | Goldberg et al. | | 6,881,218 B2 | 4/2005 | Beyer et al. |
| 6,511,492 B1 | 1/2003 | Rosenbluth et al. | | 7,001,424 B2 | 2/2006 | Patel et al. |
| 6,511,496 B1 | 1/2003 | Huter et al. | | 7,033,376 B2 | 4/2006 | Tsukernik |
| 6,511,503 B1 | 1/2003 | Burkett et al. | | 7,041,117 B2 | 5/2006 | Suon et al. |
| 6,517,559 B1 | 2/2003 | O'Connell | | 7,147,649 B2 | 12/2006 | Thomas |
| 6,517,573 B1 | 2/2003 | Pollock et al. | | 7,340,960 B2 * | 3/2008 | Niblock .................... 73/760 |
| 6,537,295 B2 | 3/2003 | Petersen | | 2001/0000799 A1 | 5/2001 | Wessman et al. |
| 6,540,722 B1 | 4/2003 | Boyle et al. | | 2001/0020175 A1 | 9/2001 | Yassour et al. |
| 6,540,767 B1 | 4/2003 | Walak et al. | | 2001/0023358 A1 | 9/2001 | Tsukernik |
| 6,540,768 B1 | 4/2003 | Diaz et al. | | 2001/0039431 A1 | 11/2001 | DeVries et al. |
| 6,544,280 B1 | 4/2003 | Daniel et al. | | 2002/0032461 A1 | 3/2002 | Marshall |
| 6,551,303 B1 | 4/2003 | Van Tassel et al. | | 2002/0042626 A1 | 4/2002 | Hanson et al. |
| 6,551,340 B1 | 4/2003 | Konya et al. | | 2002/0045918 A1 | 4/2002 | Suon et al. |
| 6,551,342 B1 | 4/2003 | Shen et al. | | 2002/0055767 A1 | 5/2002 | Forde et al. |
| 6,558,404 B2 | 5/2003 | Tsukernik | | 2002/0116024 A1 | 8/2002 | Goldberg et al. |
| 6,558,405 B1 | 5/2003 | McInnes | | 2002/0138097 A1 | 9/2002 | Ostrovsky et al. |
| 6,558,406 B2 | 5/2003 | Okada | | 2002/0165575 A1 | 11/2002 | Saleh |
| 6,563,080 B2 | 5/2003 | Shapovalov et al. | | 2002/0193825 A1 | 12/2002 | McGuckin, Jr. et al. |
| 6,569,183 B1 | 5/2003 | Kim et al. | | 2002/0193826 A1 | 12/2002 | McGuckin, Jr. et al. |
| 6,569,184 B2 | 5/2003 | Huter | | 2002/0193827 A1 | 12/2002 | McGuckin, Jr. et al. |
| 6,572,605 B1 | 6/2003 | Humes | | 2002/0193828 A1 | 12/2002 | Griffin et al. |
| 6,575,997 B1 | 6/2003 | Palmer et al. | | 2003/0004540 A1 | 1/2003 | Linder et al. |
| 6,582,447 B1 | 6/2003 | Patel et al. | | 2003/0004541 A1 | 1/2003 | Linder et al. |
| 6,589,266 B2 | 7/2003 | Whitcher et al. | | 2003/0028241 A1 | 2/2003 | Stinson |
| 6,592,607 B1 | 7/2003 | Palmer et al. | | 2003/0071285 A1 | 4/2003 | Tsukernik |
| 6,592,616 B1 | 7/2003 | Stack et al. | | 2003/0093110 A1 | 5/2003 | Vale |
| 6,596,011 B2 | 7/2003 | Johnson et al. | | 2003/0097145 A1 | 5/2003 | Goldberg et al. |
| 6,602,273 B2 | 8/2003 | Marhall | | 2003/0109824 A1 | 6/2003 | Anderson et al. |
| 6,607,553 B1 | 8/2003 | Healy et al. | | 2003/0109897 A1 | 6/2003 | Walak et al. |
| 6,610,077 B1 | 8/2003 | Hancock et al. | | 2003/0114735 A1 | 6/2003 | Silver et al. |
| 6,616,680 B1 | 9/2003 | Thielen | | 2003/0120286 A1 * | 6/2003 | Burbank et al. ............. 606/142 |
| 6,616,681 B2 | 9/2003 | Hanson et al. | | 2003/0130680 A1 | 7/2003 | Russell |
| 6,620,183 B2 | 9/2003 | DiMatteo | | 2003/0139765 A1 | 7/2003 | Patel et al. |
| 6,623,450 B1 | 9/2003 | Dutta | | 2003/0153943 A1 | 8/2003 | Michael et al. |
| 6,623,506 B2 | 9/2003 | McGucken, Jr. et al. | | 2003/0153945 A1 | 8/2003 | Patel et al. |
| 6,623,507 B2 | 9/2003 | Saleh | | 2003/0163159 A1 | 8/2003 | Patel et al. |
| 6,629,993 B2 | 10/2003 | Voinov | | 2003/0171771 A1 | 9/2003 | Anderson et al. |
| 6,640,077 B2 | 10/2003 | Suzuki | | 2003/0171803 A1 | 9/2003 | Shimon |
| 6,641,590 B1 | 11/2003 | Palmer et al. | | 2003/0176888 A1 | 9/2003 | O'Connell |
| 6,645,152 B1 | 11/2003 | Jung et al. | | 2003/0191516 A1 | 10/2003 | Weldon et al. |
| 6,645,224 B2 | 11/2003 | Gilson et al. | | 2003/0195554 A1 | 10/2003 | Shen et al. |
| 6,652,555 B1 | 11/2003 | Van Tassel et al. | | 2003/0195556 A1 | 10/2003 | Stack et al. |
| 6,652,556 B1 | 11/2003 | Van Tassel et al. | | 2003/0199918 A1 | 10/2003 | Patel et al. |
| 6,652,558 B2 | 11/2003 | Patel et al. | | 2003/0208227 A1 | 11/2003 | Thomas |
| 6,652,692 B2 | 11/2003 | Pedersen | | 2003/0208253 A1 | 11/2003 | Beyer et al. |
| 6,656,203 B2 | 12/2003 | Roth et al. | | 2004/0006364 A1 | 1/2004 | Ladd |
| 6,660,021 B1 | 12/2003 | Palmer et al. | | 2004/0059373 A1 | 3/2004 | Shapiro et al. |
| 6,663,650 B2 | 12/2003 | Sepetka et al. | | 2004/0068288 A1 | 4/2004 | Palmer et al. |
| 6,679,902 B1 | 1/2004 | Boyle et al. | | 2004/0073252 A1 | 4/2004 | Goldberg et al. |
| 6,679,903 B2 | 1/2004 | Kurz | | 2004/0082867 A1 | 4/2004 | Esch et al. |
| 6,682,490 B2 | 1/2004 | Roy et al. | | 2004/0082966 A1 | 4/2004 | WasDyke |
| 6,685,722 B1 | 2/2004 | Rosenbluth et al. | | 2004/0087999 A1 | 5/2004 | Bosma et al. |
| 6,685,738 B2 | 2/2004 | Chouinard et al. | | 2004/0088000 A1 | 5/2004 | Muller |
| 6,689,150 B1 | 2/2004 | Van Tassel et al. | | 2004/0088001 A1 | 5/2004 | Bosma et al. |
| 6,695,813 B1 | 2/2004 | Boyle et al. | | 2004/0088002 A1 | 5/2004 | Boyle et al. |

| | | | |
|---|---|---|---|
| 2004/0093015 A1 | 5/2004 | Ogle | |
| 2004/0102806 A1 | 5/2004 | Broome et al. | |
| 2004/0116959 A1 | 6/2004 | McGuckin, Jr. et al. | |
| 2004/0138693 A1 | 7/2004 | Eskuri et al. | |
| 2004/0153110 A1 | 8/2004 | Kurz et al. | |
| 2004/0153118 A1 | 8/2004 | Clubb et al. | |
| 2004/0153119 A1 | 8/2004 | Kusleika et al. | |
| 2004/0158273 A1 | 8/2004 | Weaver et al. | |
| 2004/0158274 A1 | 8/2004 | WasDyke | |
| 2004/0167568 A1 | 8/2004 | Boyle et al. | |
| 2004/0172042 A1 | 9/2004 | Suon et al. | |
| 2004/0176672 A1 | 9/2004 | Silver et al. | |
| 2004/0186510 A1 | 9/2004 | Weaver | |
| 2004/0186512 A1 | 9/2004 | Bruckheimer et al. | |
| 2004/0193209 A1 | 9/2004 | Pavcnik et al. | |
| 2004/0199240 A1 | 10/2004 | Dorn | |
| 2004/0210121 A1* | 10/2004 | Fuimaono et al. | 600/374 |
| 2004/0220610 A1 | 11/2004 | Kreidler et al. | |
| 2004/0220611 A1 | 11/2004 | Ogle | |
| 2004/0230220 A1 | 11/2004 | Osborne | |
| 2004/0243173 A1 | 12/2004 | Inoue | |
| 2004/0254523 A1 | 12/2004 | Fitzgerald et al. | |
| 2005/0015111 A1 | 1/2005 | McGuckin, Jr. et al. | |
| 2005/0019370 A1 | 1/2005 | Humes | |
| 2005/0021075 A1 | 1/2005 | Bonnette et al. | |
| 2005/0021076 A1 | 1/2005 | Mazzocchi et al. | |
| 2005/0021152 A1 | 1/2005 | Ogle et al. | |
| 2005/0027314 A1 | 2/2005 | WasDyke | |
| 2005/0055045 A1 | 3/2005 | DeVries et al. | |
| 2005/0055046 A1 | 3/2005 | McGuckin, Jr. et al. | |
| 2005/0080447 A1 | 4/2005 | McGuckin, Jr. et al. | |
| 2005/0080449 A1 | 4/2005 | Mulder | |
| 2005/0085847 A1 | 4/2005 | Galdonik et al. | |
| 2005/0090858 A1 | 4/2005 | Pavlovic | |
| 2005/0131451 A1 | 6/2005 | Kleshinski et al. | |
| 2005/0159771 A1 | 7/2005 | Peterson | |
| 2005/0165442 A1* | 7/2005 | Thinnes et al. | 606/200 |
| 2005/0182439 A1 | 8/2005 | Lowe | |
| 2005/0222604 A1 | 10/2005 | Schaeffer | |
| 2005/0288703 A1 | 12/2005 | Beyer et al. | |
| 2005/0288704 A1* | 12/2005 | Cartier et al. | 606/200 |
| 2006/0004402 A1 | 1/2006 | Voeller et al. | |
| 2006/0015137 A1 | 1/2006 | WasDyke et al. | |
| 2006/0036279 A1 | 2/2006 | Eidenschink et al. | |
| 2006/0041271 A1 | 2/2006 | Bosma et al. | |
| 2006/0069405 A1 | 3/2006 | Schaeffer et al. | |
| 2006/0069406 A1 | 3/2006 | Hendriksen et al. | |
| 2006/0079928 A1 | 4/2006 | Cartier et al. | |
| 2006/0079930 A1 | 4/2006 | McGuckin, Jr. et al. | |
| 2006/0095068 A1 | 5/2006 | WasDyke et al. | |
| 2006/0122522 A1* | 6/2006 | Chavan et al. | 600/505 |
| 2006/0203769 A1 | 9/2006 | Saholt et al. | |
| 2006/0206138 A1 | 9/2006 | Eidenschink | |
| 2006/0259067 A1 | 11/2006 | Welch et al. | |
| 2006/0259068 A1 | 11/2006 | Eidenschink | |
| 2007/0005095 A1 | 1/2007 | Osborne et al. | |
| 2007/0005104 A1 | 1/2007 | Kusleika et al. | |
| 2007/0005105 A1 | 1/2007 | Kusleika et al. | |

FOREIGN PATENT DOCUMENTS

| | | | |
|---|---|---|---|
| EP | 1 092 401 A1 | | 4/2001 |
| EP | 1 336 393 A2 | | 8/2003 |
| EP | 1 475 110 A1 | | 11/2004 |
| FR | 2 781 143 A1 | | 1/2000 |
| FR | 2 791 551 A1 | | 10/2000 |
| WO | WO-97/29794 A1 | | 8/1997 |
| WO | 9926530 A1 | | 6/1999 |
| WO | WO0032092 | * | 6/2000 |
| WO | WO-00/56390 A1 | | 9/2000 |
| WO | WO-02/055125 A2 | | 7/2002 |
| WO | WO-03/003927 A1 | | 1/2003 |
| WO | WO-03/004074 A3 | | 1/2003 |
| WO | WO-2004/012587 A2 | | 2/2004 |
| WO | WO-2005/009214 A2 | | 2/2005 |

OTHER PUBLICATIONS

Consensus Conference, "Prevention of Venous Thrombosis and Pulmonary Embolism", JAMA, Aug. 8, 1986, vol. 256, No. 6, pp. 744-749.

Hirsch, D. R. et al., "Prevalence of Deep Venous Thrombosis Among Patients in Medical Intensive Care", JAMA, Jul. 26, 1995, 274(4):335-337.

Hirsch, S. B. et al., Case Reports: Accidental Placement of the Greenfield Filter in the Heart: Report of Two Cases et al., Journal of Vascular Surgery, Dec. 1987, vol. 6, No. 6.

Hoff, W. S. et al., "Early Experience With Retrievable Inferior Vena Cava Filters in High-Risk Trauma Patients", Journal of the American College of Surgeons, Dec. 2004, vol. 199, No. 6, pp. 869-874.

Hyers, T. M. et al., "Antithrombotic Therapy for Venous Thromboembolic Disease", Chest, Jan. 2001, 119(1):176S-193S.

Ihnat, D. M. et al., "Treatment of Patients With Venous Thromboembolism and Malignant Disease: Should Vena Cava Filter Placement Be Routine?", Journal of Vascular Surgery, Nov. 1998, vol. 28, No. 8, pp. 800-807.

Inge, T. H. et al., "Bariatric Surgery for Severely Overweight Adolescents: Concerns and Recommendations", Pediatrics, Jul. 2004, vol. 114, No. 1, pp. 217-223.

Izutani, H. et al., "Migration of an Inferior Vena Cava Filter to the Right Ventricle and Literature Review", Can J Cardiol, Feb. 2004, vol. 20, No. 2, pp. 233-235.

Jacobs, D. G. et al., "The Role of Vena Caval Filters in the Management of Venous Thromboembolism" The American Surgeon, Aug. 2003, vol. 69, No. 8, pp. 635-642.

Jacobs, D. G. et al., Letters to the Editor, The Journal of Trauma, Dec. 1997, vol. 43, No. 6, pp. 988-989.

Jain, V. et al., "Preoperative Vena Caval Interruption for Venous Thrombosis Associated With Ovarian Malignancy", Acta Obstetricia Et Gynecologica Scandinavica.

Jarrett B.P. et al., Inferior Vena Cava Filters in Malignant Disease, Journal of Vascular Surgery, 2002, 36:704-707.

Joels, C. S. et al., "Complications of Inferior Vena Cava Filters", The American Surgeon, Aug. 2003, vol. 69, No. 8, pp. 654-659.

Jones K. V. et al., "Tricuspid Insufficiency After Intracardiac Migration of a Greenfield Filter: Case Report and Review of The Literature", Journal of Vascular Surgery, Sep. 1996, vol. 24, No. 3, pp. 494-498.

Kellum, J. M., "Gastric Banding" Annals of Surgery, Jan. 2003, vol. 237, No. 1, pp. 17-18.

Kelly, J. et al., "Anticoagulation or Inferior Vena Cava Filter Placement for Patients With Primary Intracerebral Hemorrhage Developing Venous Thromboembolism?", Stroke, 2003, 34:2999-3005.

Kerr, A. et al., "Bidirectional Vena Cava Filter Placement", Journal of Vascular Surgery, Oct. 1995, vol. 22, No. 4.

Khansarinia, S. et al., Prophylactic Greenfield Filter Placement in Selected High-Risk Trauma Patients, Journal of Vascular Surgery, 1995, 22:231-236.

Kim, D. et al., "Insertion of the Simon Nitinol Caval Filter: Value of the Antecubital Vein Approach", American Journal of Roentgenology, Sep. 1991, 157:521-522.

Kim, J. et al., "Preliminary Report on the Safety of Heparin for Deep Venous Thrombosis Prophylaxis After Severe Head Injury", The Journal of Trauma: Injury, Infection, and Critical Care, Jul. 2002, vol. 53, No. 1, pp. 38-43.

Kim, V. et al., "Epidemiology of Venous Thromboembolic Disease", Emergency Medicine Clinics of North America, Nov. 2001, vol. 19, No. 4, pp. 839-859.

Kimmerly, W. S. et al., "Graduate Surgical Trainee Attitudes Toward Postoperative Thromboprophylaxis", Southern Medical Journal, Aug. 1999, vol. 92, No. 9, pp. 790-794.

Kinney, T. B. et al., "Does Cervical Spinal Cord Injury Induce a Higher Incidence of Complications After Prophylactic Greenfield Inferior Vena Cava Filter Usage?", Journal of Vascular and Interventional Radiology, 1996, 7:907-915.

Kinney, T. B. et al., "Regarding "Limb Asymmetry in Titanium Greenfield Filters: Clinically Significant?"", Journal of Vascular Surgery, Jun. 1998, vol. 27, No. 6.

Kistner, R. L., Definitive Diagnosis and Definitive Treatment in Chronic Venous Disease: A Concept Whose Time Has Come:, Journal of Vascular Surgery, Nov. 1996, vol. 24, No. 5, pp. 703-710.

Knudson, M. M. et al., "Prevention of Venous Thromboembolism in Trauma Patients", The Journal of Trauma, Sep. 1994, vol. 37, No. 3, pp. 480-487.

Knudson, M. M. et al., "Thromboembolism After Trauma—An Analysis of 1602 Episodes From the American College of Surgeons National Trauma Data Bank" Annals of Surgery, Sep. 2004, vol. 240, No. 3, pp. 490-498.

Knudson, M. M. et al., Thromboembolism Following Multiple Trauma, The Journal of Trauma, Jan. 1992, vol. 32, No. 1, pp. 2-11.

Knudson, M. M. et al., "Venous Thromboembolism After Trauma", Current Opinion in Critical Care, 2004, 10:539-548.

Koga, F. et al., "Deep Vein Thrombosis During Chemotherapy in a Patient With Advanced Testicular Cancer: Successful Percutaneous Thrombectomy Under Temporary Placement of Retrievable Inferior Vena Cava Filter", International Journal of Uroloty, 2001, 8:90-93.

Konya, A. et al., "New Embolization Coil Containing a Nitinol Wire Core: Preliminary in Vitro and in Vivo Experiences", Journal of Vascular and Interventional Radiology, 2001, 12:869-877.

Kreutzer J.et al., "Healing Response to the Clamshell Device for Closure of Intracardiac Defects in Humans", Catheterization and Cardiovascular Interventions, 2001, vol. 54.

Kudsk, K. A. et al., "Silent Deep Vein Thrombosis in Immobilized Multiple Trauma Patients", The American Journal of Surgery, Dec. 1989, vol. 158, pp. 515-519.

Kyrle, P. A. et al., Deep Vein Thrombosis, The Lancet, Mar. 26-Apr. 1, 2005, 365(9465):1163-1174.

Langan III, E. M. et al., "Prophylactic Inferior Vena Cava Filters in Trauma Patients at High Risk: Follow-Up Examination and Risk/Benefit Assessment", Journal of Vascular Surgery, 1999, 30:484-490.

Leach, T. A. et al., "Surgical Prophylaxis for Pulmonary Embolism", The American Surgeon, Apr. 1994, vol. 60, No. 4, pp. 292-295.

Leoni, C. J. et al., "Classifying Complications of Interventional Procedures: A Survey of Practicing Radiologists", Journal of Vascular and Interventional Radiology, 2001, 12:55-59.

Letai, A., "Cancer, Coagulation, and Anticoagulation", The Oncologist, 1999, 4:443-449.

Lewis-Carey, M. B. et al., "Temporary IVC Filtration Before Patent Foramen Ovale Closure in a Patient With Paradoxic Embolism", Journal of Vascular and Interventional Radiology, 2002, 13:1275-1278.

Lidagoster, M. I. et al., Superior Vena Cava Occlusion After Filter Insertion, Journal of Vascular Surgery, Jul. 1994, vol. 20, No. 1.

Lin, J. et al., "Factors Associated With Recurrent Venous Thromboembolism in Patients With Malignant Disease", Journal of Vascular Surgery, 2003, 37:976-983.

Lin, P. H. et al., "The Regained Referral Ground and Clinical Practice of Vena Cava Filter Placement in Vascular Surgery", The American Surgeon, Oct. 2002, vol. 68, No. 10, pp. 865-870.

Linsenmaier U. et al, "Indications, Management, and Complications of Temporary Inferior Vena Cava Filters", Cardiovascular and Interventional Radiology, 1998, 21:464-469.

Lopez-Beret, P. et al., "Systematic Study of Occult Pulmonary Thromboembolism in Patients With Deep Venous Thrombosis", Journal of Vascular Surgery, 2001, 33:515-521.

Lorch, H. et al., "In Vitro Studies of Temporary Vena Cava Filters", Cardiovascular and Interventional Radiology, 1998, 21:146-150.

Lujan, J. A. et al., "Laparoscopic Versus Open Gastric Bypass in the Treatment of Morbid Obesity", Annals of Surgery, Apr. 2004, vol. 239, No. 4, pp. 433-437.

Luo, X. Y. et al., "Non-Newtonian Flow Patterns Associated With an Arterial Stenosis", Journal of Biomechanical Engineering, Nov. 1992, 114:512-514.

MacDonald, K. G. Jr., "Overview of the Epidemiology of Obesity and the Early History of Procedures to Remedy Morbid Obesity", Archives of Surgery, Apr. 2003, 138(4):357-360.

Manke, C. et al., "MR Imaging-Guided Stent Placement in Iliac Arterial Stenoses: A Feasibility Study", Radioilogy, 2001, 219:527-534.

Matthews, B. D. et al., "Inferior Vena Cava Filter Placement: Preinsertion Inferior Vena Cava Imaging", The American Surgeon, Aug. 2003, vol. 69, No. 8, pp. 649-653.

Mortele, K. J. et al., "The Swedish Laparoscopic Adjustable Gastric Banding for Morbid Obesity: Radiologic Findings in 218 Patients", American Journal of Roentgenology, 2001, 177:77-84.

Murakami, M. et al., "Deep Venous Thrombosis Prophylaxis in Trauma: Improved Compliance With a Novel Miniaturized Pneumatic Compression Device", Journal of Vascular Surgery, 2003, 38:923-927.

Nakagawa, N. et al., "A Retrievable Nitinol Vena Cava Filter: Experimental and Initial Clinical Results", Journal of Vascular and Interventional Radiology, 1994, 5:507-512.

Napolitano, L. M. et al., "Asymptomatic Deep Venous Thrombosis in the Trauma Patient: Is an Aggressive Screening Protocol Justified?", The Journal of Trauma: Injury, Infection, and Critical Care, 1997, vol. 39, No. 4, pp. 651-659.

Nazario, R. et al., "Treatment of Venous Thromboembolism", Cardiology in Review, 2002, 10(4):249-259.

Neeman, Z. et al., "Metastatic Involvement of a Retrieved Inferior Vena Cava Filter", (Clinical Center) and National Cancer Institute, National Institutes of Health, Bethesda, MD), p. 1585.

Neill, A. M. et al., "Retrievable Inferior Vena Caval Filter for Thromboembolic Disease in Pregnancy", British Journal of Obstetrics and Gynaecology, Dec. 1997, vol. 104, pp. 1416-1418.

Neri, E. et al., "Protected Iliofemoral Venous Thrombectomy in a Pregnant Woman With Pulmonary Embolism and Ischemic Venous Thrombosis", Texas Heart Institute Journal, 2002, vol. 29, No. 2, pp. 130-132.

Nguyen, N. T. et al., "A Comparison Study of Laparoscopic Versus Open Gastric Bypass for Morbid Obesity", Journal of The American College of Surgeons, Aug. 2000, vol. 191, No. 2, pp. 149-155.

Nguyen, N. T. et al., "Comparison of Pulmonary Function and Postoperative Pain After Laparoscopic Versus Open Gastric Bypass: A Randomized Trial", Journal of Americal College of Surgeons, 2001, 192:469-477.

Norwood, S. H. et al., "A Potentially Expanded Role for Enoxaparin in Preventing Venous Thromboembolism in High Risk Blunt Trauma Patients", Journal of The American College of Surgeons, 2001, 192:161-167.

Nunn, C. R. et al., "Cost-Effective Method for Bedside Insertion of Vena Caval Filters in Trauma Patients,"The Journal of Trauma, Nov. 1997, vol. 43, No. 5, pp. 752-758.

O'Brien, P. E. et al., "Laparoscopic Adjustable Gastric Banding in the Treatment of Morbid Obesity", Archives of Surgery, Apr. 2003, 138(4):376-382.

O'Malley, K. F. et al., "Prevention of Pulmonary Embolism After Pelvic Fracture: Rational Use of Inferior Vena Caval Filters", (Cooper Hospital/University Medical Center), Jan. 1996, vol. 40.

O'Sullivan, G. J. et al., "Endovascular Management of Iliac Vein Compression (May-Thurner) Syndrome", Journal of Vascular and Interventional Radiology, 2000, 11:823-836.

Offner, P. J. et al., "The Role of Temporary Inferior Vena Cava Filters in Critically Ill Surgical Patients", Archives of Surgery, Jun. 2003, vol. 138, pp. 591-595.

Olearchyk, A. S., "Insertion of the Inferior Vena Cava Filter Followed by Iliofemoral Venous Thrombectomy for Ischemic Venous Thrombosis", Journal of Vascular Surgery, Apr. 1987, vol. 5, No. 4, pp. 645-647.

Olin, J. W., "Pulmonary Embolism", Reviews in Cardiovascular Medicine, 2002, 3(2):S68-S75.

Ornstein, D. L. et al., "Cancer, Thrombosis, and Anticoagulants", Current Opinion in Pulmonary Medicine, 2000, 6:301-308.

Ortega, M. et al., "Efficacy of Anticoagulation Post-Inferior Vena Caval Filter Placement", American Surgeon, May 1998, vol. 64, Issue 5, pp. 419-423.

Ortiz-Saracho, J. et al., "An Unusual Cause of Pulmonary Artery Thrombosis", Chest, 1998, 114:309-310.

Owings, J. T. et al., "Timing of the Occurrence of Pulmonary Embolism in Trauma Patients", Archives of Surgery, Aug. 1997, 132(8):862-867.

Padberg, F. T. et al, "Hemodynamic and Clinical Improvement After Superficial Vein Ablation in Primary Combined Venous Insufficiency With Ulceration", Journal of Vascular Surgery, 1996, 24:711-718.

Pais, S. O. et al., "Percutaneous Insertion of the Greenfield Inferior Vena Cava Filter: Experience With Ninety-Six Patients", Journal of Vascular Surgery, Oct. 1988, vol. 8. No. 4.

Papers of the Western Surgical Association, "Directed Parathyroidectomy—Feasibility and Performance in 100 Consecutive Patients With Primary Hyperparathyroidism", Archives of Surgery, Jun. 2003, vol. 138, p. 637.

Participants in the Vena Caval Filter Consensus Conference, "Recommended Reporting Standards for Vena Caval Filter Placement and Patient Follow-Up", Journal of Vascular Surgery, 1999, 30:573-579.

Partsch, H. et al., "Frequency of Pulmonary Embolism in Patients Who Have Iliofemoral Deep Vein Thrombosis and Are Treated With Once- or Twice-Daily Low-Molecular Weight Heparin", Journal of Vascular Surgery, 1996, 24:774-782.

Passman, M. A. et al., "Pulmonary Embolism is Associated With the Combination of Isolated Calf Vein Thrombosis and Respiratory Symptoms", Journal of Vascular Surgery, 1997, 25:39-45.

Patton, J. H. Jr., et al., "Prophylactic Greenfield Filters: Acute Complications and Long-Term Follow-Up", The Journal of Trauma: Injury, Infection, and Critical Care, 1996, vol. 41, No. 2, pp. 231-237.

Peck, K. E. et al., "Postlaparoscopic Traumatic Inferior Vena Caval Thrombosis", Heart & Lung, Jul./Aug. 1998, vol. 27, No. 4, pp. 279-281.

Peterson, D. A. et al., "Computed Tomographic Venography is Specific But Not Sensitive for Diagnosis of Acute Lower-Extremity Deep Venous Thrombosis in Patients With Suspected Pulmonary Embolus", Journal of Vascular Surgery, 2001, 34:798-804.

Podnos, Y. D. et al., "Complications After Laparoscopic Gastric Bypass", Archives of Surgery, Sep. 2003, 138:957-961.

Porter, J. M. et al., "Reporting Standards in Venous Disease: An Update", Journal of Vascular Surgery, 1995, 21:635-645.

Prince, M. R. et al., "The Diameter of the Inferior Vena Cava and Its Implications for the Use of Vena Caval Filters", Radiology, 1983, 149:687-689.

Proctor, M. C. et al., "Assessment of Apparent Vena Caval Penetration by the Greenfield Filter", Journal of Endovascualr Surgery, 1998, 5:251-258.

Proctor, M. C., "Indications for Filter Placement", Seminars in Vascular Surgery, Sep. 2000, vol. 13, No. 3, pp. 194-198.

Qanadli, S. D. et al., "Pulmonary Embolism Detection: Prospective Evaluation of Dual-Section Helical CT Versus Selective Pulmonary Arteriography in 157 Patients", Radiology, 2000, 217:447-455.

Quirke, T. E. et al., "Inferior Vena Caval Filter Use in U.S. Trauma Centers a Practitioner Survey", The Journal of Trauma: Injury, Infection, and Critical Care, 1997, vol. 43, No. 2, pp. 333-337.

Rabkin, D. J. et al., "Nitinol Properties Affecting Uses in Interventional Radiology", Journal of Vascular and Interventional Radiology, 2000, 11:343-350.

Radke, P. W. et al., "Thrombosis in Behcet's Disease: Report of a Case Followed by a Systematic Review Using the Methodology of Evidence-Based Medicine", Journal of Thrombosis and Thrombolysis, Apr. 2001, 11(2):137-141.

Raju, N. L. et al., "Case 37: Juxtacaval Fat Collection-Mimic of Lipoma in the Subdiaphragmatic Inferior Vena Cava", Radiology, 2001, 220:471-474.

Rascona, D. A. et al., "Pulmonary Embolism-Treatment vs Nontreatment", Chest, Jun. 1999, vol. 115, No. 6, p. 1755.

Razavi, M. K. et al., "Chronically Occluded Inferior Venae Cavae: Endovascular Treatment", Radiology, 2000, 214:133-138.

Reddy, K. et al., "Insertion of an Inferior Venocaval Filter in a Pregnant Woman at Risk for Pulmonary Embolism—A Challenging Management", Departments of Obstetrics and Gynaecology and Radiology, Wexham Park Hospital, Slough, UK, 2003, p. 198.

Reekers, J. A. et al., "Evaluation of the Retrievability of the OptEase IVC Filter in an Animal Model", Journal of Vascular and Interventional Radiology, 2004, 15:261-267.

Ricotta, J. J., "Regarding Recurrent Thromboembolism in Patients With Vena Caval Filters", Journal of Vascular Surgery, 2001, vol. 33, p. 657.

Riedel, M., "Acute Pulmonary Embolism 2: Treatment", Heart, Mar. 2001, 85(3):351-360.

Robrer, M. J. et al., "Extended Indications for Placement of an Inferior Vena Cava Filter", Journal of Vascular Surgery, Jul. 1990, vol. 12, No. 1.

Rodrigues, H. L. et al., "Update of the Management of Venous Thromboembolism [16]", Rev Port Cardiol, 2002, 21(2):183-199.

Rodriguez, J. L. et al., "Early Placement of Prophylactic Vena Caval Filters in Injured Patients at High Risk for Pulmonary Embolism", The Journal of Trauma, Injury, Infection, and Critical Care, 1996, vol. 40, No. 5, pp. 797-804.

PCT Search Report application No. PCT/US06/03888, Aug. 9, 2007.

Ashley, D. W. et al., "Accurate Deployment of Vena Cava Filters: Comparison of Intravascular Ultrasound and Contrast Venography", The Journal of Trauma: Injury, Infection, and Critical Care, Jun. 2001, vol. 50, No. 6, pp. 975-981.

Authors' Abstract, Journal of Vascular and Interventional Radiology, Oct. 2002, 13(10):1062-1068.

Critical Care Medicine, vol. 32, No. 12 (Suppl.), pp. A181-A188.

Doherty, C., "Special Problems of Massive Obesity", Primary Care Physician's Resource Center, file:// D:\Special%20Problems%20of%20Massive%20Obesity.htm, retrieved Jul. 26, 2005.

Gosin, J. S., "Efficacy of Prophylactic Vena Cava Filters in High-Risk Trauma Patients", Annals of Vascular Surgery, 1997, 11:100-105.

Greenfield, L. J., "Does Cervical Spinal Cord Injury Induce a Higher Incidence of Complications After Prophylactic Greenfield Filter Usage?", Journal of Vascular and Interventional Radiology, Jul.-Aug. 1997, pp. 719-720.

Ha, T. G. Van et al., "Removal of Gunther Tulip Vena Cava Filter Through Femoral Vein Approach", Journal of Vascular and Interventional Radiology, 2005, 16:391-394.

Letters to the Editor, Journal of the American College of Surgeons, Mar. 1996, vol. 182, pp. 279-280.

Miller, A. C., "British Thoracic Society Guidelines for the Management of Suspected Acute Pulmonary Embolism", Thorax, Jun. 2003, 58(6): 470-483.

Millward, S., "Temporary IVC Filtration Before Patent Foramen Ovale Closure in a Patient With Paradoxic Embolism", Letter to the Editor, p. 937.

Natta, T. L. Van et al., "Elective Bedside Surgery in Critically Injured Patients is Safe and Cost-Effective", American Surgery, May 1998, 227(5):618-626.

Oppat, W. F. et al., "Intravascular Ultrasound-Guided Vena Cava Filter Placement", Journal of Endovascular Surgery, 1999, 6:285-287.

Participants in the Vena Caval Filter Consensus Conference, Recommended Reporting Standards for Vena Caval Filter Placement and Patient Follow-Up, Journal of Vascular Surgery, Sep. 1999, 30(3):573-579.

Poster: Clinical Science: Pulmonary Disease or Dysfunctional/Mechanical Ventilation/Weaning (Adult, Critical Care Medicine, vol. 32, No. 12 (Suppl.), pp. A111-A120.

Rogers, F. B. et al., "Five-Year Follow-Up of Prophylactic Vena Cava Filters in High-Risk Trauma Patients", Archives of Surgery, Apr. 1998, 133:406-411.

Rogers, F. B. et al., "Practice Management Guidelines for the Prevention of Venous Thromboembolism in Trauma Patients: The East Practice Management Guidelines Work Group", The Journal of Trauma: Injury, Infection, and Critical Care, Jul. 2002, 53:142-164.

Rogers, F. B. et al., "Prophylactic Vena Cava Filter Insertion in Severely Injured Trauma Patients: Indications and Preliminary Results", The Journal of Trauma, Oct. 1993, 35(4):637-642.

Rogers, F. B. et al., "Prophylactic Vena Cava Filter Insertion in Selected High-Risk Orthopaedic Trauma Patients", Journal of Orthopaedic Trauma, 1997, 11(4):267-272.

Rogers, F. B. et al., "Routine Prophylactic Vena Cava Filter Insertion in Severely Injured Trauma Patients Decreases the Incidence of Pulmonary Embolism", Journal of the American College of Surgeons, Jun. 1995 180(6):641-647.

Rogers, F. B., "Venous Thromboembolism in Trauma Patients: A Review", Surgery, Jul. 2001, vol. 130, No. 1, pp. 1-12.

Rohrer, M. J. et al., "Extended Indications for Placement of an Inferior Vena Cava Filter", Journal of Vascular Surgery, Jul. 1989, vol. 10. No. 1, pp. 44-50.

Rose, S. C. et al., "Placement of Inferior Vena Caval Filters in the Intensive Care Unit", Journal of Vascular and Interventional Radiology, 1997, 8:61-64.

Rose, S. C. et al., "Regarding "Bedside Vena Cava Filter Placement Guided With Intravascular Ultrasound"", Journal of Vascular Surgery, Apr. 2002, vol. 35, No. 4.

Rossi, G. et al., "Open to Critique: An Unusual Complication of Vena Cava Filter Placement", Journal of Vascular Surgery, Nov. 1996, vol. 24, No. 5.

Rubin, B. G. et al., "Care of Patients With Deep Venous Thrombosis in an Academic Medical Center: Limitations and Lessons", Journal of Vascular Surgery, 1994, 20:698-704.

Ruiz, A. J. et al., "Heparin, Deep Venous Thrombosis, and Trauma Patients", The American Journal of Surgery, Aug. 1991, 162:159-162.

Ryskamp, R. P. et al., "Utilization of Venous Thromboembolism Prophylaxis in a Medical-Surgical ICU", Chest, Jan. 1998, 113(1):162-164.

Sapala, J. A. et al., "Fatal Pulmonary Embolism After Bariatric Operations for Morbid Obesity: A 24-Year Retrospective Analysis", Obesity Surgery, 2003, 13:819-825.

Sarasin, F. P. et al., "Management and Prevention of Thromboemboli in Patients With Cancer-Related Hypercoagulable", Journal of General Internal Medicine, Sep. 1993, 8:476-485.

Schultz, D. J. et al., "Incidence of Asymptomatic Pulmonary Embolism in Moderately to Severely Injured Trauma Patients", Journal of Trauma: Injury, Infection, and Critical Care, 2004, 56:727-733.

Shackford, S. R. et al., "Venous Thromboembolism in Patients With Major Trauma", The American Journal of Surgery, Apr. 1990, vol. 1 59, pp. 365-369.

Shaer, J. et al., "An Unusual Cause of Low Back Pain?: A Case Report", SPINE, Jun. 15, 1998, 23(12):1349-1350.

Sharpe, R. P. et al., "Incidence and Natural History of Below-Knee Deep Venous Thrombosis in High-Risk Trauma Patients", The Journal of Trauma: Injury, Infection, and Critical Care, Dec. 2002, 53:1048-1052.

Sheikh, M. A. et al., "Images in Vascular Medicine", Vascular Medicine 2001, 6:63-64.

Sheikh, M. A. et al., "Isolated Internal Jugular Vein Thrombosis: Risk Factors and Natural History", Vascular Medicine, 2002, 7:177-179.

Siddique, R. M. et al., "Thirty-Day Case-Fatality Rates for Pulmonary Embolism in the Elderly", Archives of Internal Medicine, Nov. 11, 1996, 156:2343-2347.

Simon, M. et al., "Comparative Evaluation of Clinically Available Inferior Vena Cava Filters With an in Vitro Physiologic Simulation of the Vena Cava", Radiology, 1993, 189:769-774.

Simon, M. et al., "Paddle-Wheel CT Display of Pulmonary Arteries and Other Lung Structures: A New Imaging Approach", American Journal of Roentgenology, Jul. 2001, pp. 195-198.

Simon, M., "Vena Cava Filters: Prevalent Misconceptions", Journal of Vascular and Interventional Radiology, 1999, 10:1021-1024.

Simon, M. et al., "A Vena Cava Filter Using Thermal Shape Memory Alloy", Radiology, Oct. 1977, 125:89-94.

Sing, R. F. et al., "Bedside Carbon Dioxide ($CO_2$) Preinsertion Cavagram for Inferior Vena Cava Filter Placement: Case Report", Journal of Trauma, Dec. 1999, 47(6):1140-1142.

Sing, R. F. et al., "Bedside Carbon Dioxide Cavagrams for Inferior Vena Cava Filters: Preliminary Results", Journal of Vascular Surgery, 2000, 32:144-147.

Sing, R. F. et al., "Bedside Insertion of Inferior Vena Cava Filters in the Intensive Care Unit", Journal of Trauma, Dec. 1999, 47(6):1104-1109.

Sing, R. F. et al., "Bedside Insertion of Inferior Vena Cava Filters in the Intensive Care Unit", Journal of American College of Surgeons, May 2001, 192(5):570-575.

Sing, R. F. et al., "Bedside Insertion of the Inferior Vena Cava Filter in the Intensive Care Unit", The American Surgeon, Aug. 2003, 69:660-662.

Sing, R. F. et al., "Guidewire Incidents With Inferior Vena Cava Filters", JAOA, Apr. 2001, 101(4):231-233.

Sing, R. F. et al., "Preliminary Results of Bedside Inferior Vena Cava Filter Placement", Chest, Jul. 1998, 114(1):315.

Sing, R. F. et al., "Regarding Bedside Vena Cava Filter Placement Guided With Intravascular Ultrasound", Journal of Vascular Surgery, May 2002, vol. 25, No. 5.

Smith, T. P. et al., "Acute Pulmonary Thromboembolism-Comparison of the Diagnostic Capabilities of Convention Film-Screen and Digital Angiography", Chest, 2002, 122:968-972.

Smith, T. P., "Pulmonary embolism: What's Wrong With This Diagnosis", American Journal of Roentgenology, Jun. 2000, 174:1489-1498.

Spain, D. A. et al., "Venous Thromboembolism in the High-Risk Trauma Patient: Do Risks Justify Aggressive Screening and Prophylaxis?", The Journal of Trauma: Injury, Infection, and Critical Care, 1997, vol. 42, No. 3, pp. 463-469.

Stavropoulos, S. W. et al., "In Vitro Study of Guide Wire Entrapment in Currently Available Inferior Vena Cava Filters", Journal of Vascular and Interventional Radiology, 2003, 14:905-910.

Stecker, M. S. et al., "Evaluation of a Spiral Nitinol Temporary Inferior Vena Caval Filter", Academic Radiology, 2001, 8:484-493.

Stein, P. D. et al., "Deep Venous Thrombosis in a General Hospital", Chest, 2002, 122:960-962.

Stein, P. D., "Opinions Regarding the Diagnosis and Management of Venous Thromboembolic Disease", Chest, Feb. 1998, vol. 113, No. 2, pp. 499-504.

Still, J. et al., "Experience With the Insertion of Vena Caval Filters in Acutely Burned Patients", The American Surgeon, Mar. 2000, vol. 66, No. 3, pp. 277-279.

Stover, M. D. et al., "Prospective Comparison of Contrast-Enhanced Computed Tomography Versus Magnetic Resonance Venography in the Detection of Occult Deep Pelvic Vein Thrombosis in Patients With Pelvic and Acetabular Fractures", Journal of Orthopaedic Trauma, 2002, 16(9):613-621.

Streib, E. W. et al., "Complications of Vascular Access Procedures in Patients With Vena Cava Filters", The Journal of Trauma: Injury Infection, and Critical Care, Sep. 2000, vol. 49, No. 3, pp. 553-558.

Sue, L. P. et al., "Iliofemoral Venous Injuries: An Indication for Prophylactic Caval Filter Placement", The Journal of Trauma: Injury, Infection, and Critical Care, 1995, vol. 39, No. 4, pp. 693-695.

Sugerman, H. J. et al., "Risks and Benefits of Gastric Bypass in Morbidity Obese Patients With Severe Venous Stasis Disease", Annals of Surgery, 2001, vol. 234, No. 1, pp. 41-46.

Sultan, S. et al., "Operative and Endovascular Management of Extracranial Vertebral Artery Aneurysm in Ehlers-Danlos Syndrome: A Clinical Dilemma", Vascular and Endovascular Surgery, 2002, 36(5):389-392.

Tai, N. R. M. et al., "Modern Management of Pulmonary Embolism", British Journal of Surgery, 1999, 86:853-868.

Thomas, J. H. et al., "Vena Caval Occlusion After Bird's Nest Filter Placement", American Journal of Surgery, Dec. 1998, vol. 176, pp. 598-600.

Thomas, L. A. et al., "Use of Greenfield Filters in Pregnant Women at Risk for Pulmonary Embolism", Southern Medical Journal, Feb. 1997, vol. 90, Issue 2.

Tillie-Leblond, I. et al., "Risk of Pulmonary Embolism After a Negative Spiral CT Angiogram in Patients With Pulmonary Disease: 1-Year Clinical Follow-Up Study", Radiology, 2002, 223:461-467.

Tips From Other Journals, American Family Physician, Feb. 1, 2003, vol. 67, No. 3, p. 593.

Tola, J. C. et al., "Bedside Placement of Inferior Vena Cava Filters in the Intensive Care Unit", The American Surgeon, Sep. 1999, vol. 65, No. 9, pp. 833-838.

Tovey, C. et al., "Diagnosis, Investigation, and Management of Deep Vein Thrombosis", British Medical Journal, May 31, 2003, vol. 326, i7400, p. 1180(5), 9 pages.

Trerotola, S. O. et al., "Preclinical in Vivo Testing of the Arrow-Trerotola Percutaneous Thrombolytic Device for Venous Thrombosis", Journal of Vascular and Interventional Radiology, 2001, 12:95-103.

Trujillo-Santos, J. et al., "Bed Rest or Ambulation in the Initial Treatment of Patients With Acute Deep Vein Thrombosis or Pulmonary Embolism", Chest, 2005, 127:1631-1636.

Tuna, I. C. et al., "Massive Pulmonary Embolus", Texas Heart Institute Journal, 2002, vol. 29, No. 2, pp. 144-145.

Urena, R. et al., "Bird's Nest Filter Migration to the Right Atrium", American Journal of Roentgenology, Oct. 2004, 183:1037-1039.

Valji, K., "Evolving Strategies for Thrombolytic Therapy of Peripheral Vascular Occlusion", Journal of Vascular and Interventional Radiology, 2000, 11:411-420.

Vedantham, S. et al., "Endovascular Recanalization of the Thrombosed Filter-Bearing Inferior Vena Cava", Journal of Vascular and Interventional Radiology, 2003, 14:893-903.

Vedantham, S. et al., "Lower Extremity Venous Thrombolysis With Adjunctive Mechanical Thrombectomy", Journal of Vascular and Interventional Radiology, 2002, 13:1001-1008.

Vedantham, S. et al., "Pharmacomechanical Thrombolysis and Early Stent Placement for Iliofemoral Deep Vein Thrombosis", Journal of Vascular and Interventional Radiology, 2004, 15:565-574.

Velmahos, G. C. et al., "Inability of an Aggressive Policy of Thromboprophylaxis to Prevent Deep Venous Thrombosis (DVT) in Critically Injured Patients: Are Current Methods of DVT Prophylaxis Insufficient?", Journal of the American College of Surgeons, 1998, 187:529-533.

Velmahos, G. C. et al., "Prevention of Venous Thromboembolism After Injury: An Evidence-Based Report-Part 1: Analysis of Risk Factors and Evaluation of the Role of Vena Caval Filters", The Journal of Trauma: Injury, Infection, and Critical Care, Jul. 2000, 49:132-139.

Velmahos, G. C. et al., "Prevention of Venous Thromboembolism After Injury: An Evidence-Based Report-Part II: Analysis of Risk Factors and Evaluation of the Role of Vena Caval Filters", The Journal of Trauma: Injury, Infection, and Critical Care, Jul. 2000, 49:140-144.

Velmahos, G. C. et al., "Spiral Computed Tomography for the Diagnosis of Pulmonary Embolism in Critically Ill Surgical Patients", Archives of Surgery, May 2001, 136(5):505-511.

Venbrux, Anthony C., "Protection Against Pulmonary Embolism: Permanent and Temporary Caval Filters" Department of Radiology-CVDL, The Johns Hopkins Medical Institutions, Baltimore MD, 7 pages.

Vesely, T. M. et al., "Preliminary Investigation of the Irie Inferior Vena Caval Filter", Journal of Vascular and Interventional Radiology, 1996, 7:529-535.

Vorwerk, D. et al., "Use of a Temporary Caval Filter to Assist Percutaneous Iliocaval Thrombectomy: Experimental Results", Journal of Vascular and Interventional Radiology, Sep.-Oct. 1995, 6(5):737-740.

Vrachliotis, T. G. et al., "Percutaneous Management of Extensive Clot Trapped in a Temporary Vena Cava Filter", Journal of Endovascular Therapy, 2003, 10:1001-1005.

Wakefield, T. W., Treatment Options for Venous Thrombosis, Journal of Vascular Surgery, Mar. 2000, 31(3):613-620.

Wallace, M. J., "Transatrial Stent Placement for Treatment of Inferior Vena Cava Obstruction Secondary to Extension of Intracardiac Tumor Thrombus From Hepatocellular Carcinoma", Journal of Vascular Interventional Radiology, 2003, 14:1339-1343.

Wang, W. Y. et al., "Use of a Nitinol Gooseneck Snare to Open an Incompletely Expanded Over-the-Wire Stainless Steel Greenfield Filter", American Journal of Roentgenology, Feb. 1999, 172:499-500.

Watanabe, N. et al., "Images in Cardiology: Large Thrombus Entrapped in a Patent Foramen Ovale of the Atrial Septum, Which Apparently "Disappeared" Without Embolic Events", Heart, Nov. 2002, 88(5):474.

Watanabe, S. et al., "Superior Vena Caval Placement of a Temporary Filter: A Case Report", Vascular Surgery, Jan./Feb. 2001, vol. 35, Issue 1.

Welch, H. J. et al., "Duplex Assessment of Venous Reflux and Chronic Venous Insufficiency: The Significance of Deep Venous Reflux", Journal of Vascular Surgery, 1996, 24:755-762.

Wellons, E. D. et al., "Bedside Intravascular Ultrasound-Guided Vena Cava Filter Placement", Journal of Vascular Surgery, 2003, 38:455-458.

Wells, J. L. et al., "Diagnosing Pulmonary Embolism: A Medical Masquerader", Clinician Reviews, 2001, 11(2):66-79.

Westling, A. et al., "Incidence of Deep Venous Thrombosis in Patients Undergoing Obesity Surgery", World Journal of Surgery, 2002, 26:470-473.

White, R. H. et al., "A Population-Based Study of the Effectiveness of Inferior Vena Cava Filter Use Among Patients With Venous Thromboembolism", Archives of Internal Medicine, Jul. 10, 2000, 160(13):2033-2041.

Whitehill, T. A., "Current Vena Cava Filter Devices and Results", Seminars in Vascular Surgery, Sep. 2000, 13(3):204-212.

Wholey, M. et al., "Technique for Retrieval of a Guidewire Lodged in a Vena Cava Filter", Vascular and Endovascular Surgery, 2002, 36(5):385-387.

Wiles, C. E., Letters to Editor, Journal of Trauma, Aug. 1999, 47(2):438.

Wilson, J. T. et al., "Prophylactic Vena Cava Filter Insertion in Patients With Traumatic Spinal Cord Injury: Preliminary Results", Neurosurgery, 1994, 35:234-239.

Winchell, R. J. et al., "Risk Factors Associated With Pulmonary Embolism Despite Routine Prophylaxis: Implications for Improved Protection", The Journal of Trauma, 1994, 37(4):600-606.

Wittenberg, G. et al., "Long-Term Results of Vena Cava Filters: Experiences With the LGM and the Titanium Greenfield Devices", Cardiovascular and Interventional Radiology, 1998, 21:225-229.

Wittich, G. R. et al., "Anchoring a Migrating Inferior Vena Cava Stent With Use of a T-Fastener", Journal of Vascular and Interventional Radiology, 2001, 12:994-996.

Wojcik, R. et al., "Long-Term Follow-Up of Trauma Patients With a Vena Caval Filter, The Journal of Trauma: Injury, Infection, and Critical Care", Nov. 2000, 49(5):839-843.

Wojtowycz, M. M. et al., "The Bird's Nest Inferior Vena Caval Filter: Review of a Single-Center Experience", Journal of Vascular and Interventional Radiology, 1997, 8:171-179.

Woodward, E. B. et al., "Delayed Retroperitoneal Arterial Hemorrhage After Inferior Vena Cava (IVC) Filter Insertion: Case Report and Literature Review of Caval Perforations by IVC Filters", Annals of Vascular Surgery, 2002, 16:193-196.

Xian, Z. Y. et al., "Multiple Emboli and Filter Function: An in Vitro Comparison of Three Vena Cava Filters", Journal of Vascular and Interventional Radiology, 1995, 6:887-893.

Xu, X. Y. et al., "Flow Studies in Canine Artery Bifurcations Using a Numerical Simulation Method", Journal of Biochemical Engineering, Nov. 1992, 114:504-511.

Yagi, A. et al., "Pulmonary Thromboembolism Evaluating the Indication and Effect of a Vena Caval Filter With Indium-111-Platelet Scintigraphy", Circulation Journal, Jun. 2004, 68:599-601.

Yonezawa, K. et al., "Effectiveness of an Inferior Vena Cava Filter as a Preventive Measure Against Pulmonary Thromboembolism After Abdominal Surgery", Surgery Today, 1999, 29:821-824.

Yucel, E. Kent, "Pulmonary MR Angiography: Is It Ready Now?", Radiology, 1999, 210:301-303.

Zamora, C. A. et al., "Prophylactic Stenting of the Inferior Vena Cava Before Transcatheter Embolization of Renal Cell Carcinomas: An Alternative to Filter Placement", Journal of Endovascular Therapy, 2004, 11:84-88.

Zanchetta, M. et al., "A New Permanent and Retrievable Vena Cava Filter: Its Removal After Five Months", Italian Heart Journal, Sep. 2001, 2(9):715-716.

Zeni, P. T. et al., "Use of Rheolytic Thrombectomy in Treatment of Acute Massive Pulmonary Embolism", Journal of Vascular and Interventional Radiology, 2003, 14:1511-1515.

Zinzindohoue, F. et al., "Laparoscopic Gastric Banding: A Minimally Invasive Surgical Treatment for Morbid Obesity—Prospective Study of 500 Consecutive Patients", Annals of Surgery, 2003, 237(1):1-9.

Adye, B. A., "Case Report: Errant Percutaneous Greenfield Filter Placement Into the Retroperitoneum", Journal of Vascular Surgery, Jul. 1990, vol. 12, No. 1.

Aklog, L. et al., "Acute Pulmonary Embolectomy", Circulation, 2002, 105:1416-1419.

Alexander, J. J. et al., "Is the Increasing Use of Prophylactic Percutaneous IVC Filters Justified?", The American Journal of Surgery, Aug. 1994, vol. 168, pp. 102-106.

Andrews, R. T. et al., "Entrapment of J-Tip Guidewires by Venatech and Stainless-Steel Greenfield Vena Cava Filters During Central Venous Catheter Placement: Percutaneous Management in Four Patients", Correspondence to R.T. Andrews, M.D., The Dotter Interventional Institute, Oregon Heal Sciences University, Portland, OR, pp. 424-427.

Arjomand, H. et al., "Right Ventricular Foreign Body: Percutaneous Transvenous Retrieval of a Greenfield Filter From the Right Ventricle", Angiology, 2003, vol. 54, No. 1, pp. 109-113.

Ascer, E. et al., "Superior Vena Caval Greenfield Filters: Indications, Techniques, and Results", Journal of Vascular Surgery, Mar. 1996, vol. 23, No. 3.

Asch, M. R., "Initial Experience in Humans With a New Retrievable Inferior Vena Cava Filter", Radiology, 2002, 225:835-844.

Ascher, E. et al., "Lessons Learned From a 6-Year Clinical Experience With Superior Vena Cava Greenfield Filters", Journal of Vascular Surgery, Nov. 2000, 32:881-887.

Ashley, D.W. et al., "Accurate Deployment of Vena Cava Filters: Comparison of Intravascular Ultrasound and Contrast Venography", The Journal of Trauma Injury, Infection, and Critical Care, Jun. 2001, vol. 50, No. 6, pp. 975-981.

Aswad, M. A. et al., "Early Duplex Scan Evaluation of Four Venal Interruption Devices", Journal of Vascular Surgery, 1996, 24:809-818.

Athanasoulis, C.A. et al., "Inferior Venal Caval Filters: Review of a 26-Year Single-Center Clinical Experience", Radiology, 2000, 216:54-66.

Avery, M. et al., "Reverse Engineering of Nitinol Vena Cava Filters", Material Science 102 Semester Project, Nov. 21, 2000.

Baker, R. J., "Treatment Considerations for Inherited Thrombophilia and Pulmonary Embolus", Archives of Surgery, Feb. 2001, 136,2:237.

Balshi, J. D. et al., "Original Articles" Complications of Caval Interruption by Greenfield Filter in Quadriplegics, Journal of Vascular Surgery, Apr. 1989, vol. 9, No. 4.

Barraco, R. D. et al., "Dislodgment of Inferior Vena Cava Filters During Central Line Placement: Case Report", The Journal of Trauma, Injury, Infection and Critical Care, 2000, vol. 48, No. 1, pp. 140-142.

Barreras, J. R. et al., "Recurrent Pulmonary Embolism Despite the Use of a Greenfield Filter", Clinical Nuclear, Dec. 2001, vol. 26, No. 12, pp. 1040-1041.

Barton, A. L. et al., "Caval Filter Placement for Pulmonary Embolism in a Patient With a Deep Vein Thrombosis and Primary Intracerebral Haemorrhage", Age and Ageing, Mar. 31, 2002, 2:144-146.

Becker, D. M. et al., "Inferior Vena Cava Filters", Archives of Internal Medicine, Oct. 1992, vol. 152, pp. 1985-1994.

Benjamin, M. E. et al., Duplex Ultrasound Insertion of Inferior Vena Cava Filters in Multitrauma Patients:, American Journal of Surgery, Aug. 1999, vol. 178, pp. 92-97.

Binkert, C. A. et al., "Inferior Vena Cava Filter Removal After 317-Day Implantation", Journal of Vascular Radiology, Mar. 2005, 16:393-398.

Bjarnason, H. et al., "In Vitro Metal Fatigue Testing of Inferior Vena Cava Filters", Investigative Radiology, 1994, vol. 29, No. 9, pp. 817-821.

Blebea J. et al., "Deep Venous Thrombosis After Percutaneous Insertion of Vena Cava Filters", Journal of Vascular Surgery, Nov. 1999, 30:821:829.

Bochenek, K. M. et al., "Right Atrial Migration and Percutaneous Retrieval of a Gunther Tulip Inferior Vena Cava Filter", Journal of Vascular Interventional Radiology, Sep. 2003, 14:1207-1209.

Bochicchio, G. V. et al., "Acute Caval Perforation by an Inferior Vena Cava Filter in a Multitrauma Patient: Hemostatic Control With a New Surgical Hemostat", The Journal of Trauma Injury, Infection and Critical Care, 2001, 51:991-993.

Bracale, G. et al., "Spontaneous Rupture of the Iliac Vein", The Journal of Cardiovascular Surgery, 1999, 40:871-875.

Bravo, S. M. et al., "Percutaneous Venous Interventions", Vascular Medicine, 1998, 3:61-66.

Brountzos, E. N. et al., "A New Optional Vena Cava Filter: Retrieval at 12 Weeks in an Animal Model", Journal of Vascular and Interventional Radiology, Jun. 2003, 14:763-772.

Brown, D. R. et al., "Gadolinium, Carbon Dioxide, and Iodinated Contrast Material for Planning Inferior Vena Cava Filter Placement: a Prospective Trial", Journal of Vascular and Interventional Radiology, Aug. 2003, 14:1017-1022.

Browne, R. J. et al., "Guidewire Entrapment During Greenfield Filter Deployment", Journal of Vascular Surgery, Jan. 1998, 27:174-176.

Bruckheimer, E. et al., "In Vitro Evaluation of a Retrievable Low-Profile Nitinol Vena Cava Filter", Journal of Vascular and Interventional Radiology, Apr. 2003, 14:469-474.

Bucker, A. et al., "Real-Time MR Guidance for Inferior Vena Cava Filter Placement in an Animal Model", Journal of Vascular and Interventional Radiology, Jun. 2001, 12:753-756.

Burbridge, B. E. et al., "Incorporation of the Gunther Temporary Inferior Vena Cava Filter Into the Caval Wall", Journal of Vascular and Interventional Radiology, Mar.-Apr. 1996, 7:289-290.

Cahn, M. D. et al., "Long Term Follow-up of Greenfield Inferior Vena Cava Filter Placement in Children", Journal of Vascular Surgery, Nov. 2001, 34:820-825.

Cain Jr., J.E. et al., "The Morbidity of Heparin Therapy After Development of Pulmonary Embolus in Patients Undergoing Thoracolumbar or Lumbar Spinal Fusion", SPINE, vol. 20, No. 14, 1995, pp. 1600-1603.

Campbell, J. J. et al., "Aortic Pseudoaneurysm From Aortic Penetration With a Bird's Nest Vena Cava Filter", Journal of Vascular Surgery, Sep. 2003, 38:596-599.

Carabasi III, R. A. et al., "Complications Encountered With the Use of the Greenfield Filter", The American Journal of Surgery, Aug. 1987, Vo. 154, pp. 163-168.

Carlin, A. M. et al., "Prophylactic and Therapeutic Inferior Vena Cava Filters to Prevent Pulmonary Emboli in Trauma Patients", Archives of Surgery, May 2002, vol. 137, p. 521.

Chaturvedi, R. R. et al., "Intraoperative Apical Ventricular Septal Defect Closure Using a Modified Rashkind Double Umbrella", Heart, Oct. 1996, vol. 76, No. 4, pp. 367-369.

Cherian, J. et al., "Recurrent Pulmonary Embolism Despite Inferior Vena Cava Filter Placement in Patients With the Antiphospholipid Syndrome", Journal of Clinical Rheumatology, Feb. 2005, vol. 11, No. 1, pp. 56-58.

Cho, K. J. et al., "Evaluation of a New Percutaneous Stainless Steel Greenfield Filter", Journal of Vascular and Interventional Radiology, Mar.-Apr. 1997, 8:181-187.

Conners III, M. S et al., "Duplex Scan-Directed Placement of Inferior Vena Cava Filters: A Five-year Institutional Experience", Journal of Vascular Surgery, Feb. 2002, vol. 35, No. 2, pp. 286-291.

Couch, G. G. et al., "An in Vitro Comparison of the Hemodynamics of Two Inferior Vena Cava Filters", Journal of Vascular Surgery, Mar. 2000, 31:539-549.

Couch, G. G. et al., "In Vitro Assessment of the Hemodynamic Effects of a Partial Occlusion in a Vena Cava Filter", Journal of Vascular Surgery, Apr. 1997, vol. 25, No. 4, pp. 663-672.

Crochet, D. et al., "Evaluation of the LGM Vena-Tech Infrarenal Vena Cava Filter in an Ovine Venous Thromboembolism Model", Journal of Vascular Interventional Radiology, Jun. 2001, 12:739-745.

Crochet, D. P. et al., "Long-Term Follow-Up of Vena Tech-LGM Filter: Predictors and Frequency of Caval Occlusion, Journal of Vascular Interventional Radiology", Feb. 1999, 10:137-142.

Crochet, D. P. et al., "Vena Tech-LGM Filter: Long-Term Results of a Prospective Study", Radiology, 1993, 188:857-860.

Cvoro,V. et al., "Inferior Vena Caval Filters or Anticoagulation for Patients With Haemorrhagic Stroke Complicated by Venouse Thromboembolism?", Age and Ageing, Mar. 2002, vol. 32, No. 2, Research Library, pp. 85-86.

Danetz, J. S. et al., "Selective Venography Versus Nonselective Venography Before Vena Cava Filter Placement: Evidence for More, Not Less", Journal of Vascular Surgery, Nov. 2003, Vo. 38, No. 5, pp. 928-934.

Dick, A. et al., "Declotting of Embolized Temporary Vena Cava Filter by Ultrasound and the Angiojet: Comparative Experimental in Vitro Studies, Investigative Radiology", Feb. 1998, vol. 33(2), pp. 91-97.

Gabelmann, A. et al., "Percutaneous Retrieval of Lost of Misplaced Intravascular Objects", American Journal of Radiology, Jun. 2001, 176:1509-1513.

Gelbfish, G. A. et al., "Intracardiac and Intrapulmonary Greenfield Filters: A Long-Term Follow-Up", Journal of Vascular Surgery, Nov. 1991, Vo. 14, No. 5, pp. 614-617.

Girard, T. D. et al., "Prophylactic Vena Cava Filters for Trauma Patients: A Systematic Review of the Literature", Thrombosis Research, 2003, 112:261-267.

Greenfield, L. J. et al., "Experimental Embolic Capture by Asymmetric Greenfield Filters", Journal of Vascular Surgery, Sep. 1992, vol. 16, No. 3, pp. 436-444.

Kronemyer, B., Temporary Filter Traps Pulmonary Emboly, Orthopedics Today, p. 34.

Kuszyk, B. et al., "Subcutaneously Tethered Temporary Filter: Pathologic Effects in Swine", Journal of Vascular and Interventional Radiology, Nov.-Dec. 1995, Vo. 6, No. 6, pp. 895-902.

Mobin-Uddin, K. et al., "Evolution of a New Device for the Prevention of Pulmonary Embolism", The American Journal of Surgery, Oct. 1994, vol. 168, pp. 330-334.

Patterson, R. B. et al., "Case Reports: Repositioning of Partially Dislodged Greenfield Filters From the Right Atrium by Use of a Tip Deflection Wire, Journal of Vascular Surgery", Jul. 1990, vol. 12, No. 1, pp. 70-72.

Rogers, F. B. et al., "Immediate Pulmonary Embolism After Trauma: Case Report, Journal of Trauma: Injury, Infection, and Critical Care", vol. 48, No. 1, pp. 146-148.

Salamipour, H. et al., "Percutaneous Transfemoral Retrieval of a Partially Deployed Simon-Nitinol Filter Misplaced Into the Ascending Lumbar Vein", Journal of Vascular and Interventional Radiology, 1996, 7:917-919.

Savin, M. A. et al., "Greenfield Filter Fixation in Large Vena Cavae", Journal of Vascular and Interventional Radiology, 1998, 9:75-80.

Schanzer, H. et al., "Guidewire Entrapment During Deployment of the Over-the-Guidewire Stainless Steel Greenfield Filter: A Device Design-Related Complication", Journal of Vascular Surgery, 2000, 31:607-610.

Sharafuddin, M. J. et al., "Endovascular Management of Venous Thrombotic and Occlusive Diseases of the Lower Extremities", Journal of Vascular and Interventional Radiology, Apr. 2003, 14:405-423.

Shellock, F. G. et al., "MR Procedures: Biologic Effects, Safety, and Patient Care", Radiology, 2004, 232:635-652.

"Staff Development Special, Get the Edge on Deep Vein Thrombosis", Nursing Management, Jan. 2004, pp. 21-29.

Taheri, S. A. et al., "Case Report: A Complication of the Greenfield Filter: Fracture and Distal Migration of Two Struts—A Case Report", Journal of Vascular Surgery, Jul. 1992, vol. 16, No. 1, pp. 96-99.

Tardy, B. et al, "Older People Included in a Venous Thrombo-Embolism Clinical Trial: A Patients' Viewpoint", Age and Ageing, 2003, 32:149-153.

Teitelbaum, G. P. et al., Low-Artifact Intravascular Devices: MR Imaging Evaluation, Radiology, Sep. 1988, 168:713-719.

Trerotola, S. O. et al., "Mechanical Thrombolysis of Venous Thrombosis in an Animal Model With Use of Temporary Caval Filtration", Journal of Vascular and Interventional Radiology, Sep. 2001, 12:1075-1085.

Uflacker, R., "Interventional Therapy for Pulmonary Embolism", Journal of Vascular Interventional Radiology, Feb. 2001, 12:147-164.

Weeks, S. M. et al., "Primary Gianturco Stent Placement for Inferior Vena Cava Abnormalities Following Liver Transplantation", Journal of Vascular and Interventional Radiology, Feb. 2000, 11:177-187.

Osamu Nakajima, et al., "Massive Deep Vein Thrombosis After Cesarean Section Treated With A Temporary Inferior Vena Cava Filter: A Case Report", J Cardiol 2000; 36(5): pp. 337-342.

J. Neuerburg et al., "New Retrievable Percutaneous Vena Cava Filter: Experimental in Vitro and in Vitro Evaluation", Cardiovasc Intervent Radiol, 1993, 16:224-229.

J.M. Neuerburg, et al.,"Percutaneous Retrieval of the Tulip Vena Cava Filter: Feasibility, Short-and Long-Term Changes-An Experimental Study in Dogs", Cardiovascular and Interventional Radiology, 2001, 24:418-423.

O. A. Terhaar, et al., "Extended Interval for Retrieval of Gunther Tulip Filters", J Vasc Interv Radiol, Nov. 2004, 15:1257-1262.

J. Neuerburg, et al., "Developments in Inferior Vena Cava Filters", Seminars in Interventional Radiology, vol. II, No. 4, Dec. 1994, pp. 349-357.

A. M. Palestrant, et al., "Comparative in Vitro Evaluation of the Nitinol Inferior Vena Cava Filter", Radiology, Nov. 1982, 145:351-355.

P.A. Poletti, et al., "Long-Term Results of the Simon Nitinol Inferior Vena Cava Filter", Eur. Radiol, 1998, vol. 8, pp. 289-294.

D. Putterman, et al., "Aortic Pseudoaneurysm After Penetration by a Dion Nitinol Inferior Vena Cava Filter", J Vasc Interv Radiol, 2005, 16:535-538.

Z. Qian et al., "In Vitro and in Vivo Experimental Evaluation of a New Vena Cava Filter", Journal of Vascular and Interventional Radiology, May-Jun. 1994, pp. 513-518.

C.E. Ray Jr., et al., "Complications of Inferior Vena Cava Filters", Abdominal Imaging, 1996, 21:368-374.

S. Raghavan et al., "Migration of Inferior Vena Cava Filter Into Renal Hilum", Nephron, Jun. 2002; 91, 2; Health & Medical Complete; p. 333.

J.O.F. Roehm Jr., "The Bird's Nest Filter: A New Percutaneous Transcatheter Inferior Vena Cava Filter", Journal of Vascular Surgery, Oct. 1984, vol. 1, No. 3.

J.O.F. Roehm Jr., et al., "The Bird's Nest Inferior Vena Cava Filter: Progress Report", Radiology, Sep. 1988, 168:745-749.

M. A. Savin et al., "Placement of Vena Cava Filters: Factors Affecting Technical Success and Immediate Complications", AJR, Sep. 2002, Vo. 179, pp. 597-602.

F. B. Rogers et al., "Five-Year Follow-Up of Prophylactic Vena Cava Filters in High-Risk Trauma Patients", Archives of Surgery, Apr. 1998, vol. 133, 4:Health & Medical Complete, p. 406.

J.-M. Schleich, et al., "Long-Term Follow-up of Percutaneous Vena Cava Filters: A Prospective Study in 100 Consecutive Patients", Eur J Vasc Endovasc Surg, 2001, vol. 21, pp. 450-457.

M. Shahmanesh et al., "Inferior Vena Cava Filters for HIV Infected Patients With Pulmonary Embolism and Contraindications to Anticoagulation", Sex Transm INF, 2000, 76:395-397.

H. Rousseau, et al., "The 6-F Nitinol TrapEase Inferior Vena Cava Filter: Results of a Prospective Multicenter Trial", J Vasc Interv Radiol, 2001, 12:299-304.

G. W. Stoneham et al., "Temporary Inferior Vena Cava Filters: In Vitro Comparison With Permanent IVC Filters", Journal of Vascular and Interventional Radiology, Sep.-Oct. 1995, vol. 6, pp. 731-736.

R.F. Sing, "Safety and Accuracy of Bedside Carbon Dioxide Cavography for Insertion of Inferior Vena Cava Filters In The Intensive Care Unit", American College of Surgeons, Feb. 2, 2001, vol. 192, pp. 168-171.

M. Simon et al., "Simon Nitinol Inferior Vena Cava Filter: Initial Clinical Experience", Radiology, vol. 172, No. 1, pp. 99-103, Jul. 1989.

L.D. Spence et al., "Acute Upper Extremity Deep Venous Thrombosis, Safety and Effectiveness of Superior Vena Caval Filters", Radiology, Jan. 1999, vol. 210, pp. 53-58.

R.L. Leask et al., "In Vito Hemodynamic Evaluation of a Simon Nitinol Vena Cava Filter: Possible Explanation of IVC Occlusion", J Vas Interv Radiol, May 2001, 12:613-618.

F. Stosslein et al., "A Rare Complication With An Antheor Vena Cava Filter", Cardiovascular and Interventional Radiology 1998, 21:165-167.

M.B. Streiff, "Vena Caval Filters: A Comprehensive Review", Blood, Jun. 15, 2000, vol. 95, No. 12, pp. 3669-3677.

K. Tay et al, "Repeated Gunther Tulip Inferior Vena Cava Filter Repositioning to Prolong Implantation Time", J Vasc Interv Radiol, May 2002, 13:509-512.

F. C. Taylor et al., "Vena Tech Vena Cava Filter: Experience and Early Follow-up", Journal of Vascular Interventional Radiology, Nov. 1991, 2:435-440.

C. Thery et al., "Use of a New Removable Vena Cava Filter in Order to Prevent Pulmonary Embolism in Patients Submitted to Thrombolysis", European Heart Journal, 1990, vol. 11, 334-341.

M. Porcellini et al., "Intracardiac Migration of Nitinol TrapEase Vena Cava Filter and Paradoxical Embolism", European Journal of Cardio-Thoracic Surgery, vol. 22, 2002, pp. 460-461.

L. D. Vos et al., "The Gunther Temporary Inferior Vena Cava Filter for Short-Term Protection Against Pulmonary Embolism", Cardiovascular and Interventional Radiology, 1997, 20:91-97.

S. Watanabe et al., "Clinical Experience With Temporary Vena Cava Filters", Vascular Surgery, vol. 35, No. 4, 2001, pp. 285-291.
M. Zwaan et al., "Clinical Experience With Temporary Vena Caval Filters", JVIR, Jul.-Aug. 1998, vol. 9, No. 4, pp. 594-601.
A. Dardik et al., "Vena Cava Filter Ensnarement and Delayed Migration: An Unusual Series of Cases", Journal of Vascular Surgery, Nov. 1997, vol. 26, No. 5.
J. M. Pereira de Godoy et al., "In-Vitro Evaluation of a New Inferior Vena Cava Filter-The Stent-Filter", Vascular and Endovascular Surgery, Nov. 3, 2004, vol. 38, pp. 225-228.
B. D. Davison et al., "TrapEase Inferior Vena Cava Filter Placed Via the Basilic Arm Vein: A New Antecubital Access", J Vasc Interv Radiol, Jan. 2002, 13:107-109.
M. A. De Gregorio et al, "Retrievability of Uncoated Versus Paclitaxel-Coated Gunther-Tulip IVC Filters in an Animal Model", J Vasc Interv Radiol, Jul. 2004, 15:719-726.
M.A. de Gregorio, "Inferior Vena Cava Filter Update", Arch Bronconeumol, 2004, vol. 40, No. 5, pp. 193-195.
M.A. de Gregorio et al., "The Gunther Tulip Retrievable Filter: Prolonged Temporary Filtration by Repositioning Within the Inferior Vena Cava", J Vasc Interv Radiol, Oct. 2003, 14:1259-1265.
J.L. Ebaugh et al., "Bedside Vena Cava Filter Placement Guided With Intravascular Ultrasound", Journal of Vascular Surgery, Jul. 2001, 34:21-26.
L. J. Greenfield et al., "A New Intracaval Filter Permitting Continued Flow and Resolution of Emboli", Surgery, Apr. 1973, vol. 73, No. 4, pp. 599-606.
R. W. Gunther et al., "Vena Caval Filter to Prevent Pulmonary Embolism: Experimental Study", Radiology, Aug. 1985, 156:315-320.
A. C. Venbrux, "Protection Against Pulmonary Embolism: Permanent and Temporary Caval Filters", Associate Professor of Radiology and Surgery, Department of Radiology—CVDL, The Johns Hopkins Medical Institutions, Baltimore, MD.
J.S. Gosin et al., "Efficacy of Prophylactic Vena Cava Filters in High-Risk Trauma Patients", Ann Vasc Surg, 1997, 11:100-105.
P. Haage et al., "Prototype Percutaneous Thrombolytic Device: Preclinical Testing in Subacute Inferior Vena Caval Thrombosis in a Pig Model", Radiology, Jul. 2001, 220:135-141.
W. F. Oppat et al., "Intravascular Ultrasound-Guided Vena Cava Filter Placement" J Endovasc Surg, 1999, 6:285-287.
F.D. Hammer et al., "In Vitro Evaluation of Vena Cava Filters", Journal of Vascular and Interventional Radiology, Nov.-Dec. 1994, 5:869-876.
S.J. Savader, Inferior Vena Cava Filters, Chapter 28, pp. 367-399.
S.C. Rose et al., "Placement of Inferior Vena Caval Filters in the Intensive Care Unit", Journal of Vascular Interventional Radiology, Jan.-Feb. 1997, 8:6164.
D. H. Epstein et al., "Experience With the Amplatz Retrievable Vena Cava Filter", Radiology, 1989, 172:105-110.
C.A. Athanasoulis et al., "Inferior Vena Caval Filters: Review of a 26-Year Single-Center Clinical Experience", Radiology, 2000, 216:54-66.
F. Fobbe et al., "Gunther Vena Caval Fitter: Results of Long-Term Follow-Up", AJR, Nov. 1988, 151:1031-1034.
L.J. Greenfield et al., "Extended Evaluation of the Titanium Greenfield Vena Caval Filter", Journal of Vascular Surgery, Nov. 1994, vol. 20, No. 3, pp. 458-465.
L. J. Greenfield et al., "Vena Caval Filter Use in Patients With Sepsis", Archives of Surgery, Nov. 2003, vol. 138, No. 11, Health & Medical Complete, p. 1245.
L.J. Greenfield et al., "Suprarental Filter Placement, Journal of Vascular Surgery", Sep. 1998, 28:432-438.
L.J. Greenfield et al., "Clinical Experience With The Kim-Ray Greenfield* Vena Caval Filter", Ann Surg, Jun. 1977, vol. 185, No. 6, pp. 692-698.
C. Nutting et al., "Use of a TrapEase Device as a Temporary Caval Filter", Journal of Vascular Interventional Radiology, Aug. 2001, 12:991-993.
D. Pavcnik et al., "Retrievable IVC Square Stent Filter: Experimental Study", Cardiovascular Interventional Radiology, 1999, 22:239-245.
M. Ponchon et al., "Temporary Vena Caval Filtration Preliminary Clinical Experience With Removable Vena Caval Filters", ACTA Clinica Belgica, 1999, vol. 54, pp. 223-228.

J.A. Reekers, "Re Current Practice of Temporary Vena Cava Filter Insertion: A Multicenter Registry", Journal of Vascular Interventional Radiology, Nov.-Dec. 2000, p. 1363.
J.A. Reekers et al., "Evaluation of the Retrievability of the OptEase IVC Filter in an Animal Model", Journal of Vascular Interventional Radiology, Mar. 2003, 15:261-267.
R.A. Reed, "The Use of Inferior Vena Cava Filters in Pediatric Patients for Pulmonary Embolus Prophylaxis", Cardiovascular and Interventional Radiology, 1996, 19:401-405.
J. B. Ricco et al., "Percutaneous Transvenous Caval Interruption with the LGM Filter", Ann Vasc Surg, 1988, 3:242-247.
J.D. Robinson et al., "In Vitro Evaluation of Caval Filters", Cardiovascular A ND Interventional Radiology, 1988, 11:346-351.
M.J. Wallace et al., "Inferior Vena Caval Stent Filter", AJR, Dec. 1986, 147:1247-1250.
K. Yavuz et al., "Retrievable of a Malpositioned Vena Cava Filter With Embolic Protection With Use of a Second Filter, Journal of Vascular Interventional Radiology", 2005, 16:531-534.
D. Danikas et al., "Use of a Fogarty Catheter to Open an Incompletely Expanded Vena Tech-LGM LGM Vena Cava Filter", Angiology, Apr. 2001, vol. 52, No. 4, p. 283.
PCT/US2006/003888 filed Feb. 3, 2006 Preliminary Report on Patentability dated Aug. 28, 2007.
PCT/US2006/003888 filed Feb. 3, 2006 Written Opinion dated Aug. 9, 2007.
EP 06734315.2 filed Sep. 3, 2007 Extended Search Report dated Apr. 1, 2010.
AbuRahma, A.F. et al., "Endovascular Caval Interruption in Pregnant Patients With Deep Vein Thrombosis of the Lower Extremity", Journal of Vascular Surgery, 2001, 33:375378.
Allen, T.L. et al., "Retrievable Vena Cava Filters in Trauma Patients for High-Risk Prophylaxis and Prevention of Pulmonary Embolism", The American Journal of Surgery, 2005, 189:656-661.
Arcasoy, S.M. et al., "Thrombolytic Therapy of Pulmonary Embolism", Chest, 1999, 115:1695-1707.
Arnold, D.M. et al., "Missed Opportunities for Prevention of Venous Thromboembolism", Chest, 2001, 120:1964-1971.
Brasel, K.J. et al., "Cost-Effective Prevention of Pulmonary Embolus in High-Risk Trauma Patients", The Journal of Trauma: Injury, Infection, and Critical Care, Mar. 1997, vol. 42, No. 3, pp. 456-462.
Buerger, P.M. et al., "Risk of Pulmonary Emboli in Patients With Pelvic Fractures", The American Surgeon, Aug. 1993, vol. 59, pp. 505-508.
Darcy, M.D. et al., "Short-Term Prophylaxis of Pulmonary Embolism by Using a Retrievable Vena Cava Filter", American Journal of Roentgenology, 1986, 147:836-838.
David, W. et al., "Pulmonary Embolus After Vena Cava Filter Placement", The American Surgeon, Apr. 1999, vol. 65, pp. 341-346.
Ferraro, F. et al., "Thromboembolism in Pregnancy: A New Temporary Caval Filter", Miverva Anestesiologica, 2001, vol. 67, No. 5, pp. 381-385.
Georgopoulos, S.E. et al., "Paradoxical Embolism", Journal of Cardiovascular Surgery, 2001, 42:675-677.
Goldhaber, S.Z. et al., "Acute Pulmonary Embolism: Part II Risk Stratification, Treatment, and Prevention", Circulation, 2003, 108:2834-2838.
Goldhaber, S.Z., "A Free-Floating Approach to Filters", Archives of Internal Medicine, Feb. 10, 1997, vol. 157, No. 3, pp. 264-265.
Goldhaber, S.Z., "Venous Thromboembolism in The Intensive Care Unit: The Last Frontier for Pro . . . ", Chest, Jan. 1998, 113(1):5-7.
Goldman, H.B. et al., "Ureteral Injury Secondary to an Inferior Vena Caval Filter", The Journal of Urology, Nov. 1996, vol. 156, No. 5, p. 1763.
Golueke, P.J. et al., "Interruption of the Vena Cava by Means of the Greenfield Filter: Expanding the Indications", Surgery, Jan. 1988, vol. 103, No. 1, pp. 111-117.
Gonze, M.D. et al., "Orally Administered Heparin for Preventing Deep Venous Thrombosis", American Journal of Surgery, Aug. 1998, vol. 176, pp. 176-178.
Goodman, L.R. et al., "Subsequent Pulmonary Embolism: Risk After a Negative Helical CT Pulmonary Angiogram-Prospective Comparison With Scintigraphy", Radiology, 2000, 215:535-542.

Gottlieb, R.H., "Randomized Prospective Study Comparing Routine Versus Selective Use of Sonography of the Complete Calf in Patients With Suspected Deep Venous Thrombosis", American Journal of Roentgenology, Jan. 2003, 180:241-245.

Grandas, O.H. et al., "Deep Venous Thrombosis in the Pediatric Trauma Population: An Unusual Event: Report of Three Cases", The American Surgeon, Mar. 2000, vol. 66, pp. 273-276.

Grassi, C.L. et al., "Quality Improvement Guidelines for Percutaneous Permanent Inferior Vena Cava Filter Placement for the Prevention of Pulmonary Embolism", Journal of Vascular and Interventional Radiology, Sep. 2003, 14:S271-S275.

Grassi, C.L. et al., "Vena Caval Occlusion After Simon Nitinol Filter Placement: Identification With MR Imaging in Patients With Malignancy", Journal of Vascular and Interventional Radiology, 1992, 3(3):535-539.

Greene, F.L. et al., Letters to the Editor, The Journal of Trauma: Injury, Infection, and Critical Care, May 2005, vol. 5 8, No. 5, pp. 1091-1092.

Greenfield, L.J. et al., "Free-Floating Thrombus and Pulmonary Embolism/Reply", Archives of Internal Medicine, Dec. 8-Dec. 22, 1997, pp. 2661-2662.

Greenfield, L.J. et al., "Limb Asymmetry in Titanium Greenfield Filters: Clinically Significant?", Journal of Vascular Surgery, 1997, 26:770-775.

Greenfield, L.J. et al., "Prophylactic Vena Caval Filters in Trauma: The Rest of the Story", Journal of Vascular Surgery, 2000, 32:490-497.

Greenfield, L.J. et al., "Recommended Reporting Standards for Vena Caval Filter Placement and Patient Follow-Up", Journal of Vascular and Interventional Radiology, 1999, 10:1013-1019.

Greenfield, L.J. et al., "Results of a Multicenter Study of the Modified Hood-Titanium Greenfield Filter", Journal of Vascular Surgery, 1991, 14:253-257.

Greenfield, L.J. et al., "The Percutaneous Greenfield Filter: Outcomes and Practice Patterns", Journal of Vascular Surgery, 2000, 32:888-893.

Greenfield, L.J. et al., "Twenty-Year Clinical Experience With the Greenfield Filter", Cardiovascular Surgery, Apr. 1995, vol. 3, No. 2, pp. 199-205.

Greenfield, L.J., "Cost vs Value in Vena Caval Filters", Chest, Jul. 1998, vol. 114, No. 1, pp. 9-10.

Greenfield, L.J., "Current Indications for and Results of Greenfield Filter Placement", Journal Vascular Surgery, May 1984, vol. 1, No. 3, pp. 502-504.

Greenfield, L.J., "Does Cervical Spinal Cord Injury Induce Higher Incidence of Complications After Prophylactic Greenfield Filter Usage?", Journal of Vascular and Interventional Radiology, Jul.-Aug. 1997, pp. 719-720.

Greenfield, L.J., "Recurrent Thromboembolism in Patients With Vena Cava Filters", Journal of Vascular Surgery, 2001, 33:510-514.

Greenfield, L.J., "Results of a Multi-Center Study of the Modified Hook-Titanium Greenfield Filter", Journal of Vascular Surgery, Sep. 1991.

Greenfield, L.J., "Staging of Fixation and Retrievability of Greenfield Filters", Journal of Vascular Surgery, Nov. 1994, vol. 20, No. 5, pp. 744-750.

Hagspiel, K.D. et al., "Inferior Vena Cava Filters: An Update", Applied Radiology, Nov. 1998, pp. 20-34.

Hagspiel, K.L. et al., "Difficult Retrieval of a Recovery IVC Filter", Journal of Vascular and Interventional Radiology (Letters to the Editor), Jun. 2004, vol. 15, No. 6, pp. 645-650.

Hainaux, B. et al., "Intragastric Band Erosion After Laparoscopic Adjustable Gastric Banding for Morbid Obesity: Imaging Characteristics of an Underreported Complication", American Journal of Roentgenology, Jan. 2005, 184:109-112.

Harold, K.L. et al., "Laparoscopic Approach to Open Gastric Bypass", The American Journal of Surgery, 2002, 184:61-62.

Harries, S.R., "Long-Term Follow-Up of the Antheor Inferior Vena Cava Filter", Clinical Radiology, 1998, 53:350-352.

Hastings, G.S. et al., "Repositioning the 12-F Over-the-Wire Greenfield Filter", Journal of Vascular and Interventional Radiology, 2000, 11:1207-1210.

Hill, S.L. et al., "Deep Venous Thrombosis in the Trauma Patient", The American Surgeon, Jun. 1994, vol. 60, pp. 405-408.

Hingorani, A. et al., "Upper Extremity Deep Venous Thrombosis and Its Impact on Morbidity and Mortality Rates in a Hospital-Based Population", Journal of Vascular Surgery, Nov. 1997, 26:853-860.

Holtzman, R.B. et al., "Comparison of Carbon Dioxide and Iodinated Contrast for Cavography Prior to Inferior Vena Cava Filter Placement", The American Journal of Surgery, 2003, 185:364-368.

Hosaka, J. et al., "Placement of a Spring Filter During Interventional Treatment of Deep Venous Thrombosis to Reduce the Risk of Pulmonary Embolism", ACTA Radiologica, 1999, 40:545-551.

Hughes, G.C. et al., "The Use of a Temporary Vena Caval Interruption Device in High-Risk Trauma Patients Unable to Receive Standard Venous Thromboembolism Prophylaxis", Investigative Radiology, Feb. 1999, vol. 46, No. 2, pp. 246-249.

Hunter, D.W. et al., "Retrieving the Amplatz Retrievable Vena Cava Filter", Cardiovascular and Interventional Radiology, 1987, 10:32-36.

Jackson Slappy, A.L. et al., "Delayed Transcaval Renal Penetration of a Greenfield Filter Presenting as Symptomatic Hydronephrosis", The Journal of Urology, Apr. 2002, vol. 167, pp. 1778-1779.

Jaeger, H.J. et al., "A Physiologic in Vitro Model of the Inferior Vena Cava With a Computer-Controlled Flow System for Testing of Inferior Vena Cava Filters", Investigative Radiology, Sep. 1997, vol. 32, No. 9, pp. 511-522.

Johnson, S.P. et al., "Single Institution Prospective Evaluation of the Over-The-Wire Greenfield Vena Caval Filter", Journal of Vascular and Interventional Radiology, 1998, 9:766-773.

Jones, A.L. et al., "Case Report: Use of an IVC Filter in the Management of IVC Thrombosis Occurring as a Complication of Acute Pancreatitis", Clinical Radiology, 1998, 53:462-464.

Joshi, A. et al., "Filter-Related, Thrombotic Occlusion of the Inferior Vena Cava Treated With a Gianturco Stent", Journal of Vascular and Interventional Radiology, 2003, 14:381-385.

Kasirajan, K. et al., "Percutaneous AngioJet Thrombectomy in the Management of Extensive Deep Venous Thrombosis", Journal of Vascular and Interventional Radiology, 2001, 12:179-185.

Katsamouris, A.A. et al., "Inferior Vena Cava Filters: In Vitro Comparison of Clot Trapping and Flow Dynamics", Radiology, 1988, 166:361-366.

Kaufman, J.A. et al., "Guide-Wire Entrapment by Inferior Vena Caval Filters: In Vitro Evaluation", Radiology, 1996, 198:71-76.

Kaufman, J.A. et al., "Operator Errors During Percutaneous Placement of Vena Cava Filters", American Journal of Roentgenology, Nov. 1995, 165:1281-1287.

Kaw, L.L., Jr. et al., "Use of Vena Cava Filters", Techniques in Orthopaedics, 2004, 19(4):327-336.

Kercher, K. et al., "Overview of Current Inferior Vena Cava Filters", The American Surgeon, Aug. 2003, vol. 69, pp. 643-648.

Kerlan, R.K., Jr. et al., "Residual Thrombus Within a Retrievable IVC Filter", Journal of Vascular and Interventional Radiology, 16:555-557, (Apr. 2005).

King, J.N. et al., "Vena Cava Filters", The Western Journal of Medicine, Mar. 1992, vol. 156, No. 3, pp. 295-296.

Kinney, T.B. et al., "Does Cervical Spinal Cord Injury Induce a Higher Incidence of Complications After Prophylactic Greenfield Inferior Vena Cava Filter Usage?", Journal of Vascular and Interventional Radiology, 1996, 7:907-915.

Kinney, T.B. et al., "Fatal Paradoxic Embolism Occurring During IVC Filter Insertion in a Patient With Chronic Pulmonary Thromboembolic Disease, Journal of Vascular and Interventional Radiology", 2001, 12:770-772.

Kinney, T.B., "Translumbar High Inferior Vena Cava Access Placement in Patients With Thrombosed Inferior Vena Cava Filters", Journal of Vascular and Interventional Radiology, 2003, 14:1563-1567.

Kinney, T.B., "Update on Inferior Vena Cava Filters", Journal of Vascular and Interventional Radiology, 2003, 14:425-440.

Kozak, T.K.W. et al., "Massive Pulmonary Thromboembolism After Manipulation of an Unstable Pelvic Fracture: A Case Report and Review of the Literature", The Journal of Trauma: Injury, Infection, and Critical Care, 1995, vol. 38, pp. 366-367.

Kraimps, J. et al., "Optical Central Trapping (OPCETRA) Vena Caval Filter: Results of Experimental Studies", Journal of Vascular and Interventional Radiolory, 1992, 3:697-701.

Kupferschmid, J.P. et al., "Case Report: Small-Bowel Obstruction From an Extruded Greenfield Filter Strut: An Unusual Late Complication", Journal of Vascular Surgery, Jul. 1992, vol. 16, No. 1, pp. 113-115.

Kurgan, A. et al., "Case Reports: Penetration of the Wall of an Abdominal Aortic Aneurysm by a Greenfield Filter Prong: A Late Complication", Journal of Vascular Surgery, Aug. 1993, vol. 18, No. 2, pp. 303-306.

Kuszysk, B. et al., "Subcutaneously Tethered Temporary Filter: Pathologic Effects in Swine", Journal of Vascular and Interventional Radiology, Nov.-Dec. 1995, vol. 6, No. 6, pp. 895-902.

Leask, R.L. et al., "Hemodynamic Effects of Clot Entrapment in the TrapEase Inferior Vena Cava Filter, Journal of Vascular and Interventional Radiology", 2004, 15:485-490.

Leask, R.L. et al., "In Vitro Hemodynamic Evaluation of a Simon Nitinol Vena Cava Filter: Possible Explanation of IVC Occlusion", Journal of Vascular and Interventional Radiology, 2001, 12:613-618.

Lemmon, G.W. et al., "Incomplete Caval Protection Following Suprarenal Caval Filter Placement", Angiology The Journal of Vascular Diseases, Feb. 2000, vol. 51, No. 2, pp. 155-159.

Lin, M. et al., "Successful Retrieval of Infected Gunther Tulip IVC Filter", Journal of Vascular and Interventional Radiology, 2000, 11:1341-1343.

Lipman, J.C., "Removal of Vena Caval Filter at 224 Days", Southern Medical Journal, May 2005, vol. 98, No. 5, pp. 556-558.

Loehr, S.P. et al., "Retrieval of Entrapped Guide Wire in an IVC Filter Facilitated With Use of a Myocardial Biopsy Forceps and Snare Device", Journal of Vascular and Interventional Radiology (Letter to Editor), Sep. 2001, vol. 12, No. 9, pp. 1116-1118.

Lorch, H. et al., "Current Practice of Temporary Vena Cava Filter Insertion: A Multicenter Registry", Journal of Vascular and Interventional Radiology, 2001, 11:83-88.

Lorch, H. et al., "Temporary Vena Cava Filters and Ultrahigh Streptokinase Thrombolysis Therapy: A Clinical Study", Cardiovascular Interventional Radiology, 2000, 23:273-278.

Lund, G. et al., "A New Vena Caval Filter for Percutaneous Placement and Retrieval Experimental Study", Radiology, 1984, 152:369-372.

Lund, G. et al., "Retrievable Vena Caval Filter Percutaneously Introduced", Radiology, 1985, vol. 155, p. 831.

Machado, L.G. et al., "Medical Applications of Shape Memory Alloys", Brazilian Journal of Medical and Biological Research, 2003, 36:683-691.

Magnant, J.G. et al., "Current Use of Inferior Vena Cava Filters", Journal of Vascular Surgery, Nov. 1992, vol. 16, No. 5, pp. 701-706.

Marston, W.A. et al., "Re: Comparison of the AngioJet Rheolytic Catheter to Surgical Thrombectomy for the Treatment of Thrombosed Hemodialysis Grafts", Journal of Vascular and Interventional Radiology (Letters to the Editor), Sep. 2000, vol. 11, No. 8, pp. 1095-1099.

McCowan, T.C. et al., "Complications of the Nitinol Vena Caval Filter", Journal of Vascular and Interventional Radiology, 1992, 3:401-408.

Melinek, J. et al., "Autopsy Findings Following Gastric Bypass Surgery for Morbid Obesity", Arch Path Lab Med, 2002 126:1091-1095.

Mihara, H. et al., "Use of Temporary Vena Cava Filters After Catheter-Directed Fragmentation and Thrombolysis in Patients With Acute Pulmonary Thromboembolism", Japanese Circulartion Journal, Jun. 1998, vol. 62, pp. 462-464.

Millward, S.F. et a l., "Preliminary Clinical Experience with the Gunther Temporary Inferior Vena Cava Filter", Journal of Vascular and Interventional Radiology, 1994, 5:863-868.

Millward, S.F. et al., "Gunther Tulip Filter Preliminary Clinical Experience With Retrieval", Journal of Vascular and Interventional Radiology, 2000, 11:75-82.

Millward, S.F. et al., "Gunther Tulip Retrievable Vena Cava Filter: Results From the Registry of the Canadian Interventional Radiology Association", Journal of Vascular and Interventional Radiology, 2001, 12:1053-1058.

Millward, S.F. et al., "LGM (Vena Tech), Vena Caval Filter: Clinical Experience in 64 Patients", Journal of Vascular and Interventional Radiology, Nov. 1991, 2:429-433.

Millward, S.F. et al., "LGM (Vena Tech), Vena Caval Filter: Experience at a Single Institution", Journal of Vascular and Interventional Radiology, Mar.-Apr. 1994, 5:351-356.

Millward, S.F. et al., "Reporting Standards for Inferior Venal Caval Filter Placement and Patient Follow-Up: Supplement for Temporary and Retrievable/Optional Filters", Journal of Vascular and Interventional Radiology, Apr. 2005, 16:441-443.

Millward, S.F., "Gunther Tulip Retrievable Filter Why, When and How?", JACR, Jun. 2001, vol. 52, No. 3, pp. 188-192.

Millward, S.F., "Temporary and Retrievable Inferior Vena Cava Filters Current Status", Journal of Vascular and Interventional Radiology, May-Jun. 1998, vol. 9, No. 3, pp. 381-387.

Mobin-Uddin, K. et al., "Evolution of a New Device for the Prevention of Pulmonary Embolism, The American Journal of Surgery", vol. 168, Oct. 1994, pp. 330-334.

Mohan, C.R. et al., "Comparative Efficacy and Complications of Vena Caval Filters", Journal of Vascular Surgery, 1995, 21:235-236.

Montessuit, M. et al., "Screening for Patent Foramen Ovale and Prevention of Paradoxical Embolus", Ann FASC Surg, 1997, 11:168-172.

Montgomery, K.D. et al., The Detection and Management of Proximal Deep Venous Thrombosis in Patients With Acute Acetabular Fractures: A Follow-up Report:, Journal of Orthopedic Trauma, Jul. 1997, 1(5):330-336.

Munir, M.A. et al., "An in Situ Technique to Retrieve an Entrapped J-Tip Guidewire From an Inferior Vena Cava Filter", Anesth Analo, 2002, 95:308-309.

Stosslein, F. et al., "A Rare Complication With an Antheor Vena Cava Filter", Cardiovascular and Interventional Radiology, 1998, 21:165-167.

Wholey, M. et al., "Technique or Retrieval of a Guidewire Lodged in a Vena Cava Filter", Vascular and Endovascular Surgery, 2002, vol. 36, No. 5, pp. 385-387.

AbuRahma, A.F. et al., "Management of Deep Vein Thrombosis of the Lower Extremity in Pregnancy: A Challenging Dilemma", The American Surgeon, Feb. 1999, vol. 65, No. 2, pp. 164-167A.

AbuRahma, F. et al., "Etiology of Peripheral Arterial Thromboembolism in Young Patients", The American Journal of Surgery, vol. 176, Aug. 1998, pp. 158-161.

Adams, E. et al., "Retrievable Inferior Vena Cava Filter for Thrombolic Disease in Pregnancy", British Journal of Obstetrics and Gynaecology, Sep. 1998, vol. 105, pp. 1039-1042.

Ahearn, G.S. et al., "Massive Pulmonary Embolism During Pregnancy Successfully Treated With Recombinant Tissue Plasminogen Activator", Archives of Interal Medicine, Jun. 10, 2002, 162(11):1221-1227.

American Gastroenterological Association Clinical Practice Committee, Americal Gastroenterological Associattion, Sep. 2002 123:883-932.

Anderson, J.T. et al., "Bedside Noninvasive Detection of Acute Pulmonary Embolism in Critically Ill Surgical Patients", Archives of Surgery, Aug. 1999, 134(8):869-875.

Anthone, G.J. et al., The Duodenal Switch Operation for the Treatment of Morbid Obesity, Annals of Surgery, Oct. 2003, 238(4):618-628.

Arcelus, J.I. et al, "The Management and Outcome of Acute Venous Thromboembolism: A Prospective Registry Including 4011 Patients", Journal of Vascular Surgery, 2003, 38:916-922.

Authors' Abstract, "Abstracts of Current Literature", Journal of Vascular and Interventional Radiology, Oct. 2003, vol. 14, No. 10, pp. 1351-1357.

Authors' Abstracts, "Abstract of Current Literature", Journal of Vascular and Interventional Radiology, Apr. 2004, pp. 408-415.

Bass, B.L., "What's New in General Surgery: Gastrointestinal Conditions", The Journal of American College Surgeons, Dec. 2002, vol. 195, No. 6, pp. 835-854.

Bendick, P.J. et al., Serial Duplex Ultrasound Examination for Deep Vein Thrombosis in Patients With Suspected Pulmonary Embolism, Journal of Fascular Surgery, Nov. 1996, vol. 24, No. 5, pp. 732-737.

Bessoud, B. et al., Experience at a Single Institution With Endovascular Treatment of Mechanical Complications Caused by Implanted Central Venous Access Devices in Pediatric and Adult Patients, American Journal of Roentgenology, Feb. 2003, 180:527-532.

Bevoni, L., "Management of Adult Obesity", Clinician Reviews, May 2003, 13(5):56-62.

Biertho, L. et al., "Laparoscopic Gastric Bypass Versus Laparoscopic Adjustable Gastric Banding: A Comparative Study of 1,200 Cases", Journal of the American Colloge of Surgeons, Oct. 2003, vol. 197, No. 4, pp. 536-545.

Blachar A. et al., "Gastrointestinal Complications of Laparoscopic Roux-en-Y Gastric Bypass Surgery in Patients Who Are Morbidly Obese: Findings on Radiography and CT", American Journal of Roentgenology, Dec. 2002, 179:1437-1442.

Blachar, A. et al., "Gastrointestinal Complications of Laparoscopic Roux-en-Y Gastric Bypass Surgery: Clinical and Imaging Findings", Radiology, 2002, 223:625-632.

Blaszyk, H. et al., "Factor V Leiden and Morbid Obesity in Fatal Postoperative Pulmonary Embolism", Archives of Surgery, Dec. 2000, 135(12):1410-1413.

Bovyn, G. et al., "The Tempofilter®: A Multicenter Study of a New Temporary Caval Filter Implantable for up to Six Weeks", Annals of Vascular Surgery, 1997, 11:520-528.

Bridges, G.G. et al., "Expedited Discharge in Trauma Patients Requiring Anticoagulation for Deep Venous Thrombosis Prophylaxis: The LEAP Program", The Journal of Trauma: Injury, Infection and Critical Care, Feb. 2003, vol. 54, No. 2, pp. 232-235.

Brolin, R.E., "Laparoscopic Verses Open Gastric Bypass to Treat Morbid Obesity", Annals of Surgery, Apr. 2004, vol. 239, No. 4, pp. 438-440.

Capella, J.F. et al., An Assessment of Vertical Banded Gastroplasty-Roux-en-Y Gastric Bypass for the Treatment of Morbid Obesity, (Feb 2002).

Carter, Y. et al., "Deep Venous Thrombosis and ABO Blood Group Are Unrelated in Trauma Patients", The Journal of Trauma: Injury, Infection, and Critical Care, 2002, 52:112-116.

Castaneda, F. et al., "Catheter-Directed Thrombolysis in Deep Venous Thrombosis With Use of Reteplase: Immediate Results and Complications From a Pilot Study", Journal of Vascular and Interventional Radiology, 2002, 13:577-580.

Ceelen, W. et al., "Surgical Treatment of Severe Obesity With a Low-Pressure Adjustable Gastric Band, Experimental Data and Clinical Results in 625 Patients", Annals of Surgery, 2003, 237(1):10-16.

Chanduszko, A., "Determination of Nitinol Transition Temperatures Using a Dynamical Mechanical Analyzer", The International Conference on Shape Memory and Superelastic Technology, 2000 Conference Proceedings, 2001, pp. 375-381.

Chengelis, D.L. et al., "Progression of Superficial Venous Thrombosis to Deep Vein Thrombosis", Journal of Vascular Surgery, 1996, 24:745-749.

Choban, P.S. et al., "The Impact of Obesity on Surgical Outcomes: A Review, "Journal of the American College of Surgeons, Dec. 1997, vol. 185, pp. 593-603.

Chung, J.W. et al., "Acute Iliofemoral Deep Vein Thrombosis: Evaluation of Underlying Anatomic Abnormalities by Spiral CT Venography", Journal of Vascular and Interventional Radiology, 2004, 15:249-256.

Clarke, C.S. et al., "Puerperal Ovarian Vein Thrombosis With Extension Into the Inferior Vena Cava", The American Surgeon, Feb. 1999, vol. 65, No. 2, pp. 147-150.

Cooper, S.G. et al., "Distal Retraction and Inversion of the Simon Nitinol Filter During Surgical Venous Procedures: Report of Two Cases", Journal of Vascular and Interventional Radiology, 1997, 8:433-435.

Cottam, D.R. et al., "Laparoscopic Era of Operations for Morbid Obesity", Archives of Surgery, Apr. 2003, 138(4):367-375.

Cragg, A. et al., "A New Percutaneous Vena Cava Filter", American Journal of Roentgenology, Sep. 1983, 141:601-604.

Dabbagh, A. et al., "Late Complication of a Greenfield Filter Associating Caudal Migration and Perforation of the Abdominal Aorta by a Ruptured Strut", Journal of Vascular Surgery, Aug. 1995, vol. 22, No. 2, pp. 182-187.

Dake, M.D. et al., "Thrombolytic Therapy in Venous Occlusive Disease", Journal of Vascular and Interventional Radiology, 1995, 6:73S-77S.

Dalman, R. et al., "Cerebrovascular Accident After Greenfield Filter Placement for Paradoxical Embolism", Journal of Vascular Surgery, Mar. 1989, vol. 9, No. 3, pp. 452-454.

Davidson, B.L., "Dvt Treatment in 2000: State of the Art", Orthopedics, Jun. 2000, 23(6):pp. S651-s654.

De Gregorio, M.A. et al., "Animal Experience in the Gunther Tulip Retrievable Inferior Vena Cava Filter", Cardiovascular and Interventional Radiology, Nov. 2001, 24:413-417.

De Gregorio, M.A. et al., "Mechanical and Enzymatic Thrombolysis for Massive Pulmonary Embolism, Journal of Vascular and Interventional Radiology", 2002, 13:163-169.

Debing, E. et al., "Popliteal Venous Aneurysm With Pulmonary Embolism", Journal of Cardiovascular Surgery, Oct. 1998, vol. 39, No. 5, pp. 569-572.

Decousus, H. et al., "A Clinical Trial of Vena Caval Filters in the Prevention of Pulmonary Embolism in Patients With Proximal Deep-Vein Thrombosis", The New England Journal of Medicine, Feb. 12, 1998, vol. 338, No. 7, pp. 409-415.

DeMaria, E.J. et al., "Results of 281 Consecutive Total Laparoscopic Roux-en-Y Gastric Bypasses to Treat Morbid Obesity", Annals of Surgery, 2002, vol. 235, No. 5 pp. 640-647.

Dennis, J.W. et al., "Efficacy of Deep Venous Thrombosis Prophylaxis in Trauma Patients and Identification of High-Risk Groups", The Journal of Trauma, 1993, vol. 35, No. 1, pp. 132-137.

Denny, D.F. Jr., "Errant Percutaneous Greenfield Filter Placement Into the Retroperitoneum Journal of Vascular Surgery" Jun. 1991, vol. 13, No. 6.

Dewald, C.L. et al., Vena Cavography With $CO_2$ Versus With Iodinated Contrast Material for Inferior Vena Cava Filter Placement: A Prospective Evaluation, Radiology, 2000, 216:752-757.

Dibie, A. et al., "In Vivo Evaluation of a Retrievable Vena Cava Filter-The Dibie-Musset Filter: Experimental Results", Cardiovascular and Interventional Radiology, 1998, 21:151-157.

Duperier, T. et al., "Acute Complications Associated With Greenfield Filter Insertion i High-Risk Trauma Patients", The Journal of Trauma: Injury, Infection, and Critical Care, Mar. 2003, vol. 54, No. 3, pp. 545-549.

Edlow, J.A., "Emergency Department Management of Pulmonary Embolism", Emergency Medicine Clinics of North America, Nov. 2001, vol. 19, No. 4, pp. 995-1011.

Egermayer, P., "Follow-Up for Death or Recurrence Is Not a Reliable Way of Assessing the Accuracy of Diagnostic Tests for Thromboembolic Disease", Chest 1997, 111:1410-1413.

Ekim, N. et al., "Pulmonary Thromboembolism With Massive Vaginal Bleeding Due to Thrombolytic Therapy", Respirology, 2003, 8:246-248.

Engmann, E. et al., "Clinical Experience With the Antecubital Simon Nitinol IVC Filter", Journal of Vascular and Interventional Radiology, 1998, 9:774-778.

Fava, M. et al., "Massive Pulmonary Embolism: Percutaneous Mechanical Thrombectomy During Cardiopulmonary Resuscitation", Journal of Vascular and Intervention Radiology, 2005, 16:119-123.

Fava, M. et al., "Massive Pulmonary Embolism: Treatment With the Hydrolyser Thrombectomy Catheter", Journal of Vascular and Intervention Radiology, 2000, 11:1159-1164.

Feezor, R.J. et al., "Duodenal Perforation With an Inferior Vena Cava Filter: An Unusual Cause of Abdominal Pain", Journal of Vascular Surgery, 2002, pp. 1-3.

Fernandez, A.Z. Jr. et al., "Multivariate Analysis of Risk Factors for Death Following Gastric Bypass for Treatment of Morbid Obesity", Annals of Surgery, May 2004, vol. 239, No. 5, pp. 698-703.

Ferral, H., "Regarding "Lessons Learned From a 6-Year Clinical Experience With Superior Vena Cava Greenfield Filters"", Journal of Vascular Surgery, Apr. 2001, vol. 33, No. 4.

Ferris, E.J. et al., "Percutaneous Inferior Vena Caval Filters: Follow-Up of Seven Designs in 320 Patients", Radiology 1993, 188:851-856.

Fink, S. et al., "Pulmonary Embolism and Malpractice Claims", Southern Medical Journal, Dec. 1998, vol. 91, No. 12, pp. 1149-1152.

Foley, M. et al., "Pulmonary Embolism After Hip or Knee Replacement: Postoperative Changes on Pulmonary Scintigrams in Asymptomatic Patients", Radiology, 1989, 172:481485.

Fraser, J.D. et al., "Deep Venous Thrombosis: Recent Advances and Optimal Investigation With US", Radiology, 1999, 211:9-24.

Frezza, E.E. et al., "Entrapment of a Swan Ganz Catheter in an IVC Filter Requiring Caval Exploration", Journal of Cardiovascular Surgery, 1999, 40:905-908.

Friedell, M.L. et al., "Case Report: Migration of a Greenfield Filter to the Pulmonary Artery: Case Report", Journal of Vascular Surgery, Jun. 1986, vol. 3, No. 6, pp. 929-931.

Friedland, M. et al., "Vena Cava Duplex Imaging Before Caval Interruption", Journal of Vascular Surgery, Oct. 1995, vol. 24, No. 4, pp. 608-613.

Gamblin, T.C. et al., "A Prospective Evaluation of a Bedside Technique for Placement of Inferior Vena Cava Filters: Accuracy and Limitations of Intravascular Ultrasound", The American Surgeon, May 2003, vol. 69, pp. 382-386.

Garcia, N. D., "Is Bilateral Ultrasound Scanning of the Legs Necessary for Patients With Unilateral Symptoms of Deep Vein Thrombosis", Journal of Vascular Surgery, 2001, 34:792-797.

Gayer, G. et al., "Congenital Anomalies of the Inferior Vena Cava Revealed on CT in Patients With Deep Vein Thrombosis", American Journal of Roentgenology, Mar. 2003, vol. 180, pp. 729-732.

Geerts, W.H., "A Prospective Study of Venous Thromboembolism After Major Trauma", Dec. 15, 1994, vol. 331, No. 24, pp. 1601-1606.

Gelfand, E.V. et al., "Venous Thromboembolism Guidebook, Fourth Edition", Critical Pathways in Cardiology, Dec. 2003, vol. 2, No. 4, pp. 247-265.

Ginsberg, M.S. et al., "Clinical Usefulness of Imaging Performed After CT Angiography That Was Negative for Pulmonary Embolus in a High-Risk Oncologic Population", American Journal of Roentgenology, Nov. 2002, 179:1205-1208.

Girard, P. et al., "Medical Literature and Vena Cava Filters", Chest, 2002, 122:963-967.

Goldberg, M.E., "Entrapment of an Exchange Wire by an Inferior Vena Caval Filter: A Technique for Removal", Anesth Analg., Apr. 2003, 96:4, 1235-1236.

Greenfield, L.J. et al., "Filter Complications and Their Management", Seminars in Vascular Surgery, vol. 13, No. 3, Sep. 2000, pp. 213-216.

Hak, D.J., "Prevention of Venous Thromboembolism in Trauma and Long Bone Fractures", Current Opinion in Pulmonary Medicine, 2001, 7:338-343.

Hammond, F.M. et al., "Venous Thromboembolism in the Patient With Acute Traumatic Brain Injury: Screening, Diagnosis, Prophylaxis, and Treatment Issues", Journal of Head Trauma Rehabilitation, Feb. 1998, vol. 13, No. 1, pp. 36-48.

Hardhammar, P.A. et al., "Reduction in Thrombotic Events With Heparin-Coated Palmaz-Schatz Stents in Normal Porcine Coronary Arteries", Circulation, Feb. 1, 1996, vol. 93, No. 3, pp. 423-430.

Harris, E.J. Jr. et al., "Phlegmasia Complicating Prophylactic Percutaneous Inferior Vena Caval Interruption: A Word of Caution", Journal of Vascular Surgery, 1995, vol. 22, No. 5, pp. 606-611.

Hawkins, S.P. et al., "The Simon Nitinol Inferior Vena Cava Filter: Preliminary Experience in the UK", Clinical Radiology, 1992, 46:378-380.

Headrick, J.R. et al., "The Role of Ultrasonography and Inferior Vena Cava Filter Placement in High-Risk Trauma Patients", American Surgeon, Jan. 1997, vol. 63, Issue 1.

Helfet, D., Magnetic Resonance Venography to Evaluate Deep Venous Thrombosis in Patients With Pelvic and Acetabular Trauma, The Journal of Trauma: Injury, Infection, and Critical Care, Jul. 2001, p. 178.

Heng, J.T. et al., "Occlusion of Persistent Left Superior Vena Cava to Unroofed Coronary Sinus Using Vena Cava Filter and coils", Hears, Jun. 1997, vol. 77, No. 6, pp. 579-580.

Henkle, G. et al., "Patterns of Referral for Inferior Vena Caval Filtration: Delays and Their Impact", American Journal of Roentgenology, Oct. 2004, 183:1021-1024.

Hicks, M.E. et al., "Prospective Anatomic Study of the Inferior Vena Cava and Renal Veins: Comparison of Selective Renal Venography With Cavography and Relevance in Filter Placement", Journal of Vascular and Interventional Radiology, 1995, 6:721-729.

Higa, K.D. et al., "Laparoscopic Roux-en-Y Gastric Bypass for Morbid Obesity", Archives of Surgery, Sep. 2000, vol. 135, No. 9, pp. 1029-1034.

Johnson, M.S., "Current Strategies for the Diagnosis of Pulmonary Embolus", Journal of Vascular and Interventional Radiology, 2002, 13:13-23.

Kaplan, S. et al., "Surgical Management of Renal Cell Carcinoma With Inferior Vena Cava Tumor Thrombus, The American Journal of Surgery", 2002, 183:292-299.

Karmy-Jones, R. et al., "Surgical Management of Cardiac Arrest Caused by Massive Pulmonary Embolism in Trauma Patients", The Journal of Trauma: Injury, Infection, and Critical Care, 2000, vol. 48, No. 3, pp. 519-520.

Kazmers, A. et al., "Duplex Examination of the Inferior Vena Cava", The American Surgeon, Oct. 2000, vol. 66, pp. 986-989.

Kazmers, A. et al., "Intraoperative Insertion of Greenfield Filters: Lessons Learned in a Personal Series of 152 Cases", The American Surgeon, Oct. 2002, vol. 68, pp. 877-882.

Kazmers, A. et al., "Pulmonary Embolism in Veterans Affairs Medical Centers: Is Vena Cava Interruption Underutilized?", The American Surgeon, Dec. 1999, vol. 65, No. 12, pp. 1171-1175.

Kearon, C. et al., "Management of Anticoagulation Before and After Elective Surgery", The New England Journal of Medicine, May 22, 1997, vol. 336, No. 21, pp. 1506-1511.

Kelly, J. et al., "Anticoagulation or Inferior Vena Cava Filter Placemente for Patients With Primary Intracerebral Hemorrhage Developing Venous Thromboembolism?" Stroke, 2003, 34:2999-3005.

Marret, H. et al., "Re: Metastatic Involvement of a Retrieved Inferior Vena Cava Filter", Journal of Vascular and Interventional Radiology, Jul. 2004, vol. 15, No. 7, pp. 775-776.

Matteson, B. et al., "Role of Venous Duplex Scanning in Patients With Suspected Pulmonary Embolism", The Journal of Vascular Surgery, 1996, 24:768-773.

Mattos, M.A. et al., "Prevalence and Distribution of Calf Vein Thrombosis in Patients With Symptomatic Deep Venous Thrombosis: A Color-Flow Duplex Study", Journal of Vascular Surgery, 1996, 24:738-744.

Maxwell, R.A. et al., "Routine Prophylactic Vena Cava Filtration is Not Indicated After Acute Spinal Cord Injury", The Journal of Trauma: Injury, Infection, and Critical Care, 2002, 52:902-906.

McMurtry, A.L. et al., "Increased Use of Prophylactic Vena Cava Filters in Trauma Patients Failed to Decrease Overall Incidence of Pulmonary Embolism", Journal of the American College of Surgeons, 1999, 189:314-320.

Meissner, M.H. et al., Venous Thromoembolism in Trauma: A Local Manifestation of Systemic Hypercoagulability?, The Journal of Trauma: Injury, Infection, and Critical Care, Feb. 2003, vol. 54, No. 2, pp. 224-231.

Participants in the Vena Caval Filter Consensus Conference, "Recommended Reporting Standards for Vena Caval Filter Placement and Patient Follow-Up", Journal of Vascular and Interventional Radiology, 2003, 14:S427-S432.

Pelage, J. et al., "Re: Leiomyoma Recurrence After Uterine Artery Embolization, Journal of Vascular and Interventional Radiology, " Jul. 2004, vol. 15, No. 7, pp. 773-776.

Quality Improvement Guidelines for Percutaneous Inferior Vena Cava Filter Placement for the Prevention of Pulmonary Embolism (European Standards adopted and Modified by CIRSE in Cooperation With SCVIR Standards of Practice Committee), http:www.cirse.org/vena_cava_filter_crise.htm, retrieved May 17, 2002, 11 pages.

RD Heparin Arthroplasty Group, "RD Heparin Compared With Warfarin for Prevention of Venous Thromboembolic Disease Following Total Hip or Knee Arthroplasty", The Journal of Bone and Joint Surgery, Incorporation, Aug. 1994, vol. 76-A, No. 8, pp. 1174-1185.

Millward, SF., "Re: Temporary IVC Filtration before Patent Foramen Ovale Closure in a Patient with Paradoxic Embolism," Journal of Vascular and Interventional Radiology. vol. 14, Issue 7, p. 937, Jul. 2003.

Society of Critical Care Medicine 34th Critical Care Congress Phoenix, Arizona, USA Jan. 15-19, 2005: Poster Presentation: Case Reports, Critical Care Medicine. 32(12):A181-A188 (Suppl.), Dec. 2004.

Society of Critical Care Medicine 34th Critical Care Congress Phoenix, Arizona, USA Jan. 15-19, 2005: Poster: Clinical Science: Pulmonary Disease or Dysfuntion/Mechanical Ventilation/Weaning (Adult) III, Critical Care Medicine. 32(12):A111-A120 (Suppl.), Dec. 2004.

* cited by examiner

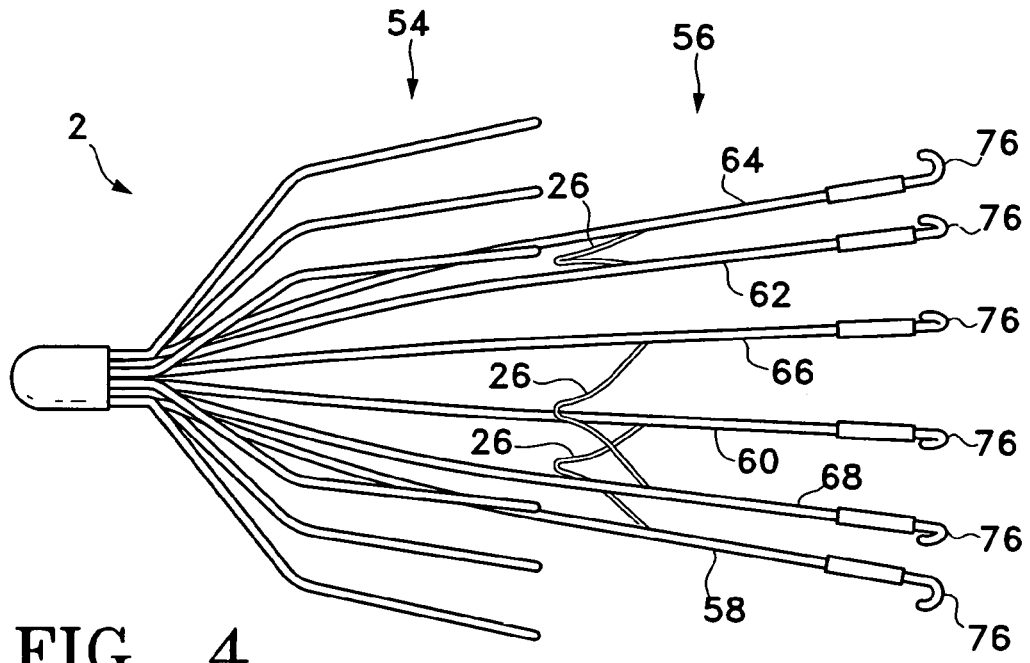
FIG. 4
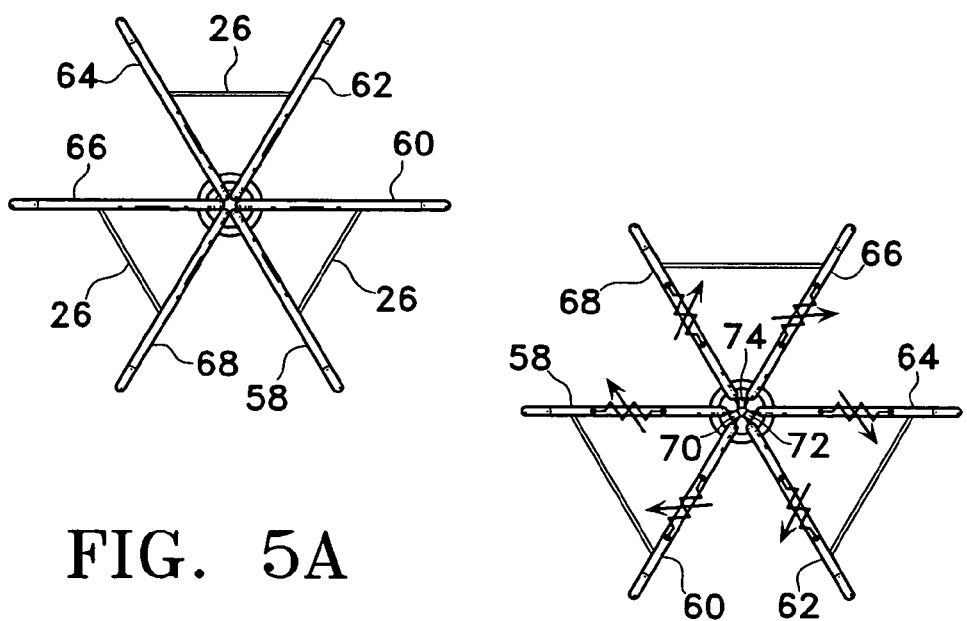
FIG. 5A
FIG. 5B

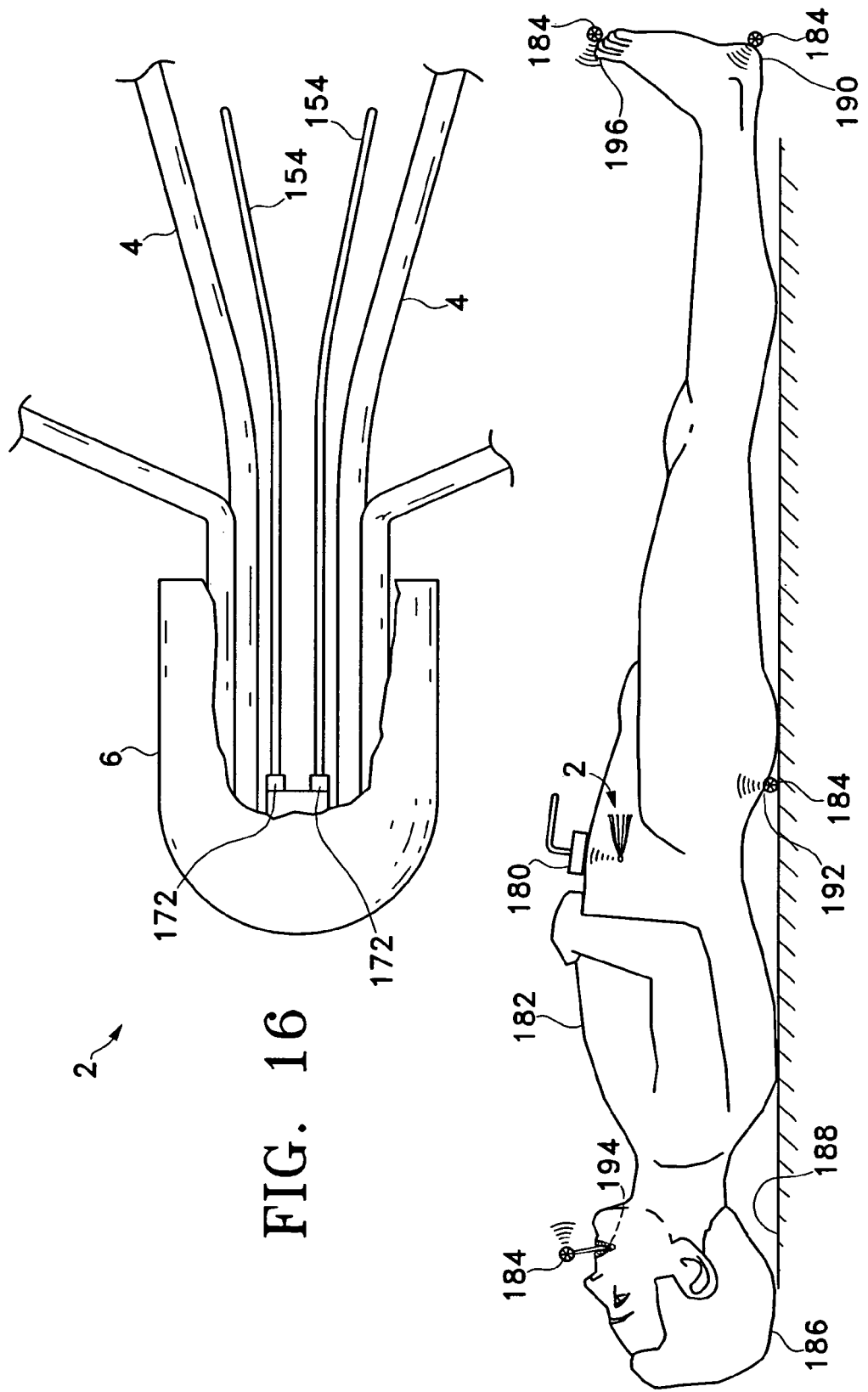

VASCULAR FILTER WITH SENSING CAPABILITY

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

A vena cava filter is a device inserted into a blood vessel to capture particles in the blood flow. Typically the device is inserted into a major vein to prevent a blood clot from reaching the lungs. Patients who have recently suffered from trauma, have had a heart attack (myocardial infarction), or who have experienced a major surgical procedure (e.g., surgical repair of a fractured hip, etc.) may have thrombosis in a deep vein. When the thrombus clot loosens from the site of formation and travels to the lung it may cause pulmonary embolism, a life-threatening condition. A vena cava filter may be placed in the circulatory system to intercept the thrombi and prevent them from entering the lungs.

Examples of various blood vessel filters are disclosed in U.S. patent application, Publication No. 2001/0000799 A1, titled "BODY VESSEL FILTER" by Wessman et al., published May 3, 2001; U.S. patent application, Publication No. 2002/0138097 A1, titled "ATRAUMATIC ANCHORING AND DISENGAGEMENT MECHANISM FOR PERMANENT IMPLANT DEVICE" by Ostrovsky et al., published Sep. 26, 2002; U.S. patent application, Publication No. 2002/0193828 A1, titled "ENDOVASCULAR FILTER" by Griffin et al., published Dec. 19, 2002; U.S. patent application, Publication No. 2003/0199918 A1, titled "CONVERTIBLE BLOOD CLOT FILTER" by Patel et al., published Oct. 23, 2003; U.S. patent application, Publication No. 2003/0208227 A1, titled "TEMPORARY VASCULAR FILTERS AND METHODS" by Thomas, published Nov. 6, 2003; U.S. patent application, Publication No. 2003/0208253 A1, titled "BLOOD CLOT FILTER" by Beyer et al., published Nov. 6, 2003; U.S. Pat. No. 4,425,908, titled "BLOOD CLOT FILTER" issued to Simon, dated Jan. 17, 1984; U.S. Pat. No. 4,643,184, titled "EMBOLU.S. TRAP" issued to Mobin-Uddin, dated Feb. 17, 1987; U.S. Pat. No. 4,817,600, titled "IMPLANTABLE FILTER" issued to Herms et al., dated Apr. 4, 1989; U.S. Pat. No. 5,059,205, titled "PERCUTANEOU.S. ANTI-MIGRATION VENA CAVA FILTER" issued to El-Nounou et al., dated Oct. 22, 1991; U.S. Pat. No. 5,344,427, entitled "FILTER WITH TRIANGULAR FINGERS" issued to Cottenceau et al., dated Sep. 6, 1994; U.S. Pat. No. 5,626,605, entitled "THROMBOSIS FILTER" issued to Irie et al., dated May 6, 1997; U.S. Pat. No. 5,755,790, titled "INTRALUMINAL MEDICAL DEVICE" issued to Chevillon et al., dated May 26, 1998; U.S. Pat. No. 6,258,026 B1, titled "REMOVABLE EMBOLU.S. BLOOD CLOT FILTER AND FILTER DELIVERY UNIT" issued to Ravenscroft et al., dated Jul. 10, 2001; U.S. Pat. No. 6,443,972 B1, titled "VASCULAR FILTER" issued to Bosman et al., dated Sep. 3, 2002; U.S. Pat. No. 6,497,709 B1, titled "METAL MEDICAL DEVICE" issued to Heath, dated Dec. 24, 2002; U.S. Pat. No. 6,506,205 B2, titled "BLOOD CLOT FILTERING SYSTEM issued to Goldberg et al., dated Jan. 14, 2003; and U.S. Pat. No. 6,517,559 B1, titled "BLOOD FILTER AND METHOD FOR TREATING VASCULAR DISEASE" issued to O'Connell, dated Feb. 11, 2003; U.S. Pat. No. 6,540,767 B1, titled "RECOILABLE THROMBOSIS FILTERING DEVICE AND METHOD" issued to Walak et al., dated Apr. 1, 2003; U.S. Pat. No. 6,620,183 B2, titled "THROMBU.S. FILTER WITH BREAK-AWAY ANCHOR MEMBERS" issued to DiMatteo, dated Sep. 16, 2003; each of which is incorporated herein by reference in its entirety.

Typically the vessel filter comprises a plurality of radially expandable legs that supports one or more filter baskets which are conical in configuration. The device is adapted for compression into a small size to facilitate delivery into a vascular passageway and is subsequently expandable into contact with the inner wall of the vessel. The device may later be retrieved from the deployed site by compressing the radially expanded legs and the associated baskets back into a small size for retrieval. Alternatively, the vessel filter may be configured for permanent implantation. The radially expandable leg may further comprise engagements for anchoring the filter in position within a blood vessel (e.g., vena cava). For example, the expandable legs may have hooks that can penetrate into the vessel wall and positively prevent migration of the filter in either direction along the length of the vessel. The body of the filter may comprise various biocompatible materials including compressible spring metals and shape memory materials to allow easy expansion and compression of the filter within the vessel. The hooks on the radially expandable legs may further comprise materials more elastic than the legs to permit the hooks to straighten in response to withdrawal forces to facilitate withdrawal from the endothelium layer without risk of significant injury to the vessel wall. In one variation, the hooks are formed on the ends of a portion of the radially expandable legs, but not on others.

For treatment of recurrent pulmonary embolism, a vessel filter may be permanently implanted in the patient's vena cava. Alternatively, the vessel filter may be implanted in the patient's vena cava for a few weeks, after which the vessel filter is removed. However, during the implanted period, it is generally difficult to monitor the condition of the vessel filter. For example, to verify that the vessel filter has not migrated along the length of the blood vessel or become misaligned post-implantation, complex imaging systems such as MRI, CT Scan or X-ray may be needed to determine the condition of the vessel filter. In addition, the hooks on the implanted vessel filter may penetrate and/or perforate the blood vessel wall. Perforation of the blood vessel may require immediate intervention by the physician. Furthermore, a possible contraindication associated with the implantation of vessel filter is the build-up of significant amount of trapped thrombus either within the implanted filter or directly upstream from the vessel filter. The built of thrombus may result in complications that require intervention by the physician. For example, when too much thrombus has been trapped inside and/or behind the vessel filter, the build-up may impede blood flow in the blood vessel. The pressure build-up due to the partial blockage of the blood flow may also lead to expansion of the blood vessel, which may cause tilting and/or migration of the vessel filter. In addition, for retrievable filter application, too much thrombus build-up may also make it difficult to compress the vessel filter and thus hinder the vessel filter removal process. In some medical condition, it may also be desirable to wait till the captured thrombus has lysed before the physician proceed with the removal of the vessel filter.

Thus, it may be desirable to monitor the position/orientation of the implanted vessel filter and/or the condition/parameter of the implanted vessel filter.

Various vascular devices with built-in sensors have been previously disclosed. Examples of some of these filters are described in U.S. patent application, Publication No. 2003/0171803 A1, titled "ENDOVASCULAR DEVICE FOR ENTRAPMENT OF PARTICULATE MATTER AND METHOD FOR U.S.E" by Shimon, published Sep. 11, 2003; U.S. patent application, Publication No. 2002/0165575 A1, titled "VASCULAR FILTRATION DEVICE" by Saleh, published Nov. 7, 2002; U.S. patent application, Publication No. 2004/0082867 A1, titled "VASCULAR GRAFT WITH INTEGRATED SENSOR" by Esch et al., published Apr. 29, 2004; U.S. Pat. No. 6,652,556, titled "FILTER APPARATU.S. FOR OSTIUM OF LEFT ATRIALAPPENDAGE" issued to VanTassel et al., dated Nov. 25, 2003; U.S. Pat. No. 5,053,008, titled "INTRACARDIAC CATHETER" issued to Bajaj, dated Oct. 1, 1991; U.S. Pat. No. 6,623,507 titled "VASCULAR FILTRATION DEVICE" issued to Saleh, dated Sep. 23, 2003; U.S. Pat. No. 6,702,847 titled "ENDOLUMINAL DEVICE WITH INDICATOR MEMBER FOR REMOTE DETECTION OF ENDOLEAKS AND/OR CHANGES IN DEVICE MORPHOLOGY" issued to DiCarlo, dated Mar. 9, 2004; U.S. Pat. No. 6,053,873 titled "PRESSURE-SENSING STENT" issued to Govari et al., dated Apr. 25, 2000; U.S. Pat. No. 6,092,530 titled "REMOTELY INTERROGATED IMPLANT DEVICE WITH SENSOR FOR DETECTING ACCRETION OF BIOLOGICAL MATTER" issued to Weissman et al., dated Jul. 25, 2000; U.S. Pat. No. 6,206,835 titled "REMOTELY INTERROGATED DIAGNOSTIC IMPLANT DEVICE WITH ELECTRICALLY PASSIVE SENSOR" issued to Spillman et al., dated Mar. 27, 2001; U.S. Pat. No. 6,726,703 titled "DISTAL PROTECTION DEVICE AND METHOD" issued to Broome et al., dated Apr. 27, 2004; each of which is incorporated herein by reference in its entirety. Most of these devices utilize sensors to monitor the physiological condition of the surrounding environment (e.g., blood pressure, temperature, blood chemistry, etc.), and the sensors are not designed to monitor the condition of the device itself.

An improved filter with a mechanism and/or a sensor for monitoring the condition of the implanted vessel filter may be desirable. For example, an electronic circuit that is capable of monitoring a physical parameter of the vessel filter, and thereby notify the user of the condition of the vessel filter may be desirable. A device that can provide efficient and cost-effective verification of the condition of the implanted vessel filter will improve the physicians confidence in the implanted device, and also allow the physician to intervene when the vessel becomes dislodged through migration or when too much thrombus has been captured within the vessel filter. In particular, a device that allows regular monitoring of the vessel filter while the patient is away from the hospital or the treatment facility may be especially useful in preventing occurrences of serious complications while the vessel filter is implanted.

BRIEF SUMMARY OF THE INVENTION

Accordingly, described herein is an implantable vessel filter having an integrated sensing capability for monitoring the conditions that are associated with the filter. For example, an electronic circuit may be implemented on the vessel filter to measure a physical parameter (e.g., strain, position of the filter legs, pressure on the filter body, etc.) that corresponds to the condition of the vessel filter. This improved vessel filter may detect the capturing and/or build-up of thrombus within the implanted vessel filter. In one variation, a vessel filter comprises one or more legs or other members that would themselves perform as a sensor device for detecting distention, which would indicate the presence of a clot or thrombus therein. In one design, a passive inductive circuit is connected to one or more of the filter legs to measure the strain on the filter legs. In another design, technologies similar to the ones implemented on a passive RFID system may be implemented on the vessel filter to direct energy to and receive information from micro-electronics connected to or attached on the legs or members of the filter.

A miniaturized sensor (e.g., pressure sensors, piezoresistive sensors, optical sensors, strain gauge, etc.) may also be positioned on or integrated within the vessel filter body. The miniaturized sensor may be adapted for measuring the strain or other physical parameters on the filter legs. Alternatively, the miniaturized sensor may be configured for measuring the amount of blood clots that are captured within the vessel filter. An external device may be utilized periodically to provide energy to the micro-electronics on the vessel filter, which would then relay information regarding the desired measurements (e.g., distention or migration of the device, increased strain on the vessel filter legs, increase shear stress on the vessel filter legs, etc.). Other electromagnetic and/or inductive mechanisms, that are well known to one of ordinary skill in the art, may also be implanted to provide energy to, and/or establish communication with, the micro-electronics embedded on the vessel filter. The vessel filter monitor may be utilized by the physician to assess the condition of the implanted vessel filter during post-implantation follow-up visits. In another variation, the vessel filter monitoring system may be implemented in the form of a device carried by the patient following implantation of the vessel filter to monitor the condition of the implanted vessel filters. The external device would query the embedded micro-electronics, perhaps, once or twice a day, and should a problem be detected (e.g., distention, migration, uneven distribution of strain or stress, etc.), the device would notify the patient and/or the physician. Although in the preferred design, an electrically passive circuit is implemented to measure the condition of the vessel filter, one of ordinary skill in the art, having the benefit of this disclosure, would appreciate that an active circuit may also be utilized to measure the condition of the vessel filter. For example, an active circuit with an on-board battery may be implemented to measure the strain on the legs of the vessel filter and then transmit the measured data to a remote device. Alternatively, the circuit may be provided with a rechargeable battery that can be energized through electromagnetic waves.

The improved implantable vessel filter may provide one or more of the various advantages described herein, including, for example, early notification of significant thrombus build-up (e.g., detection of distension or increased strain in the vessel filter legs, etc.), early notification of filter migration, displacement, and/or perforation, etc. In the case that the vessel filter provides notification of excessive thrombus build-up, the physician may then remove the filter and the captured thrombus. Alternatively, the physician may clear the captured thrombus from the filter, for example, by introducing a catheter to remove the captured thrombus through suction or by injecting the patient with an anticoagulation medication. In the case that the vessel filter provides notification of migration and/or displaced alignment thereof (e.g., uneven distribution of strain in the various vessel legs may indicate that the vessel filter has moved or has become misaligned with the blood vessel), the physician may remove the migrated and/or misaligned vessel filter.

Detection of uneven strain, stress, and/or pressure distribution on the filter appendages or body structure may suggest that possible complication has occurred with the implanted vessel filter. This would prompt the physician to order additional tests (e.g., X-ray, MRI, etc.) to further verify the condition of the implanted vessel filter. In the event that complications have occurred, the physician may then provide necessary intervention. For example, the detection by the remote monitor of uneven strain distribution on the implanted vessel filter may prompt the physician to order an MRI. The MRI may show that the vessel filter has perforated the blood vessel and blood is leaking out of the blood vessel into the abdomen of the patient. Surgical intervention may then be provided to repair the damage vessel and/or removed the dislodged vessel filter.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIG. 4 illustrates another variation where the vessel filter comprises two filter cones.

FIG. 5A illustrates the physical connections in the distal legs of the vessel filter shown in FIG. 4. The three pairs of filter legs are measured independently with corresponding electronic measurement circuits embedded within the filter sleeve. The vessel filter is shown without its proximal legs.

FIG. 5B is an electrical circuit diagram representing the electrical connections of the vessel filter shown in FIG. 5A.

FIG. 16 illustrates another variation where the sensing members are connected to sensors placed within the sleeve of the vessel filter. The sensors are configured to measure stress and/or displacement of the sensing members.

FIG. 17 illustrates another implementation where a reference beacon is utilized to determine the position of the vessel filter within the body of the patient.

DETAILED DESCRIPTION OF THE INVENTION

Figure 1A:
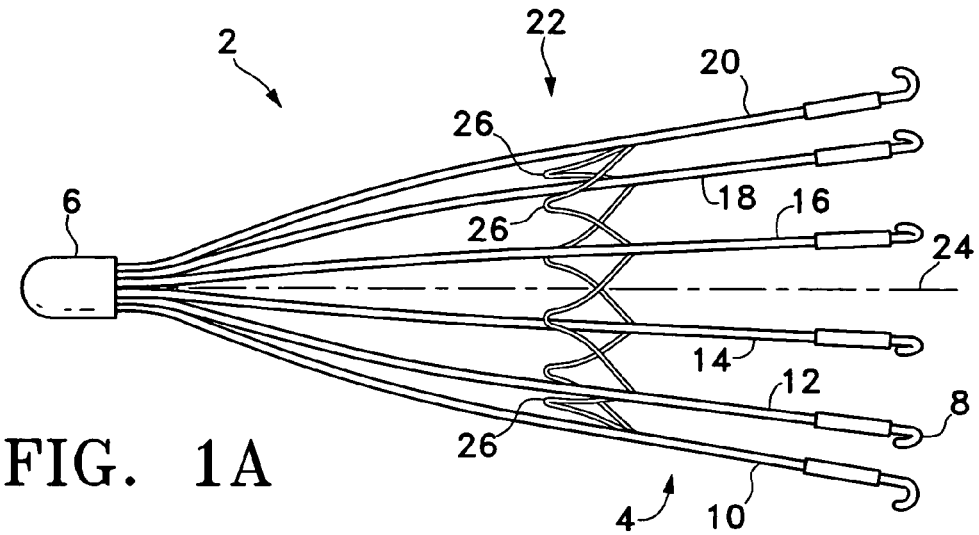
FIG. 1A illustrates a variation of an implantable vessel filter with an integrated electronic circuit for measuring the strain on the radially expandable legs.

The following detailed description should be read with reference to the drawings, in which identical reference numbers refer to like elements throughout the different figures. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated this invention need not be limited to applications in humans. As one of ordinary skill in the art would appreciate, variations of the invention may be applied to other mammals as well. Moreover, it should be understood that embodiments of the present invention may be applied in combination with various catheters, tubing introducers or other filter deployment devices for implantation and/or retrieval of the filter in a vessel within a patient's body.

A vena cava filter is used herein as an example application of the filter device to illustrate the various aspects of the invention disclosed herein. In light of the disclosure herein, one of ordinary skill in the art would appreciate that variations of the filter device may be applicable for placement in various hollow body organs and elongated cavities in a human body for capturing particles in a fluid stream. It is also contemplated that the filter device described herein may be implemented for capturing particles other than blood clots.

It must also be noted that, as used in this specification and the appended claims, the singular forms "a," "an" and "the" include plural referents unless the context clearly dictates otherwise. Thus, for example, the term "a hook" is intended to mean a single hook or a combination of hooks, "a fluid" is intended to mean one or more fluids, or a mixture thereof.

In one aspect of the invention, the implantable vessel filter 2 comprises a plurality of legs 4 (e.g., flexible or semi-flexible wiring, etc.) extending from a sleeve 6 in the radial direction towards the distal end 8 of the device. In this variation, an electronic circuit connected to a leg 4 is provided to measure the strain in the leg 4. It is well known to one of ordinary skill in the art that the electric resistance of a wire increases with increasing strain and decreases with decreasing strain. By measuring the changes in resistance in the deployed metallic legs of a vessel filter, one may determine the increase or decrease in strain experienced by the filter leg. When a thrombus is trapped within a deployed filter, the blood flow pushes the thrombus against the filter legs, thus increasing strain experienced by the filter legs. By measuring the strain on the filter legs one may be able to determine the presence of a thrombus.

An electronic measurement circuit may be connected to the proximal portion of the legs and placed within the sleeve of the vessel filter. The legs are configured with materials such that they may be collapsed toward a central axis along the length of the device for insertion and/or retrieval from a patient's vascular system. A hook is provided on the distal end of each of the legs, such that when the vessel filter is deployed inside a blood vessel, the hooks engage the blood vessel wall and anchor the filter in the blood vessel. Each of the filter legs may comprise various metals or metal alloys (e.g., nitinol) that are well known to one of ordinary skill in the art for implantation within a blood vessel. In one variation, each of the filter legs comprises a conductive alloy which increases the sensitivity factor of the resistive characteristics of the filter leg in response to strain exerted on the filter leg. Various metals and metal alloys that are well known to one of ordinary skill in the art to have high sensitivity to strain (e.g., platinum, platinum-iridium, platinum-tungsten, isoelastic alloy, constantan alloy, Nichrome V, Karma, etc.) may be incorporated during the manufacturing of the vessel filter legs.

Figure 1B:
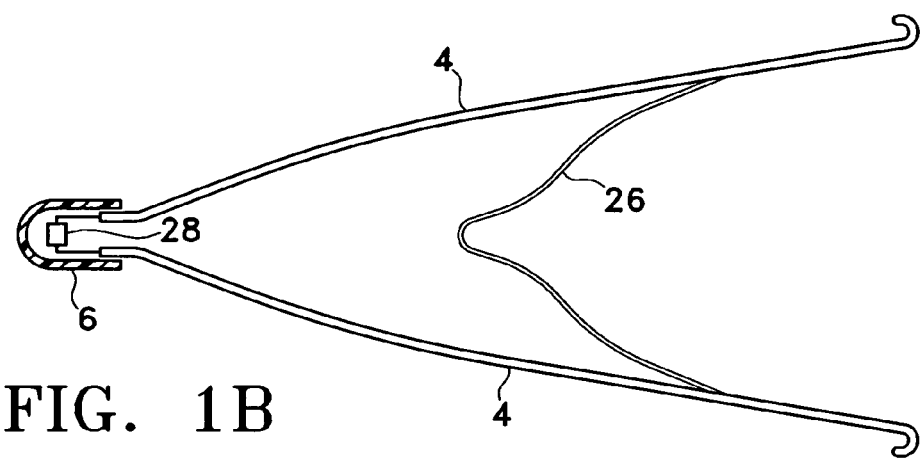
FIG. 1B illustrates the particular electronic circuit connection for measuring the strain on the vessel filter legs which are implemented in the vessel filter of FIG. 1A. In this variation, conductive bridges are provided between the legs.

The plurality of legs 4 may be configured for deployment into one or more cone shaped filters. FIG. 1A illustrates an example implementing a single cone filter design where six legs 10, 12, 14, 16, 18, 20 expand to form a conical-shaped filter basket 22 centered around the longitudinal axis 24 of the device. In this particular design, electric conductive bridges 26 connect each of the filter legs 10, 12, 14, 16, 18, 20 with adjacent filter legs. An electronic measurement circuit 28 may be configured, a shown in FIG. 1B, to measure the changes in strain in the pairs of corresponding legs 4. Each pair of legs 4 may be configured with a corresponding electronic measurement circuit. Alternatively, a single electric measurement circuit may be adapted to measure the strain on different pairs of filter legs 4 either serially or simultaneously. The electronic measurement circuit may comprise an integrated circuit implemented on a silicon-based chip. Alternatively, the electronic measurement circuit may be implemented on a thin polymeric film. The electronic measurement circuit may comprise various active or passive circuits that are well known to one of ordinary skill in the art for measuring resistance and/or impedance.

Figure 1C:
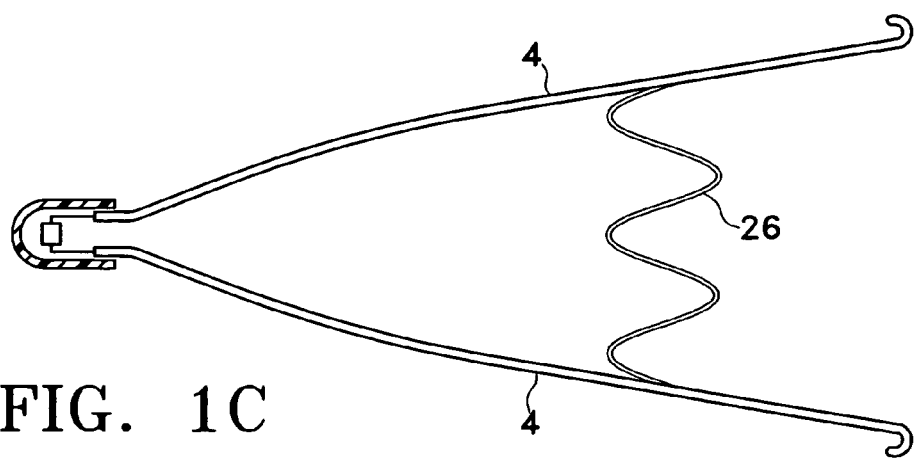
FIG. 1C illustrates another variation where the conductive bridge between the two legs comprises a strain gauge which is highly sensitive to extension due to pressure and/or stress that is exerted on it.
Figure 1D:
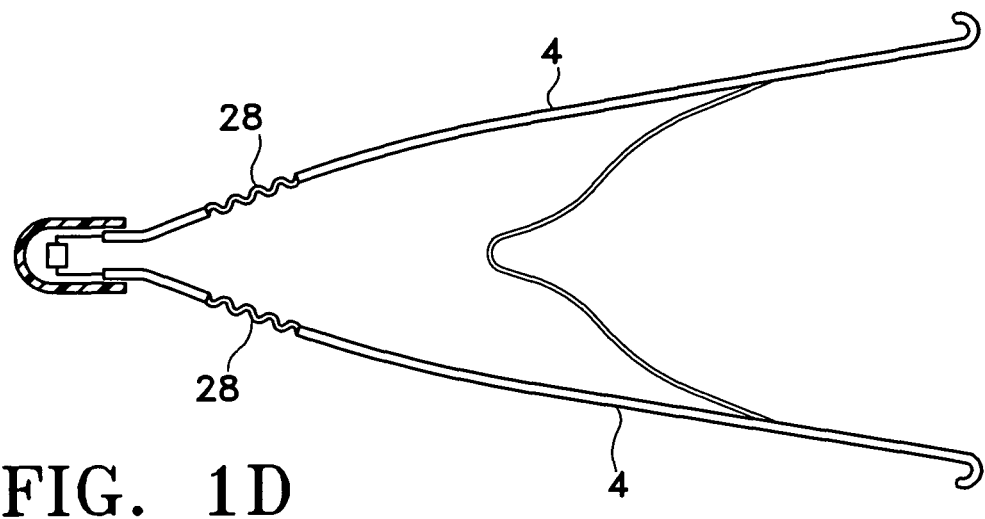
FIG. 1D illustrates yet another variation where the structure of the legs is configured with materials/profile that are highly sensitive to increase in strain due to distension of the filter structure.

The conductive bridge 26 may comprise material with low sensitivity to strain and serves the primary purpose of conducting electricity between the filter legs, such that the resistant changes detected by the electronic measurement circuit are primarily dependent on the strain exerted on the filter legs 4. Alternatively, the conductive bridge 26 may be sensitive to strain, whereby the variation in resistance detected by the electronic measurement circuit 28 represents the combined change in resistance in the leg portions and the conductive bridge. In another design, as shown in FIG. 1C, the filter legs 4 comprise material with low sensitivity to strain while the conductive bridge 26 is comprised of a strain gauge material or other materials that are sensitive to strain, such that when a trapped thrombus pushes on the filter legs 4 and/or the conductive bridge 26, an increase in strain in the conductive bridge occurs. In yet another design, as shown in FIG. 1D, portions 28 of the filter legs 4 comprise strain gauge material. The strain gauge portion 28 of the filter leg 4 may also have structure or pattern that increases its sensitivity factor. When a thrombus is trapped between the filter legs 4, the blood flow pushes on the thrombus which in turn applies pressure on the filter legs 4 and forces them to divert from each other. As a result, the strain gauge portion 28 of the filter leg 4 will experience increase in strain.

Figure 2:
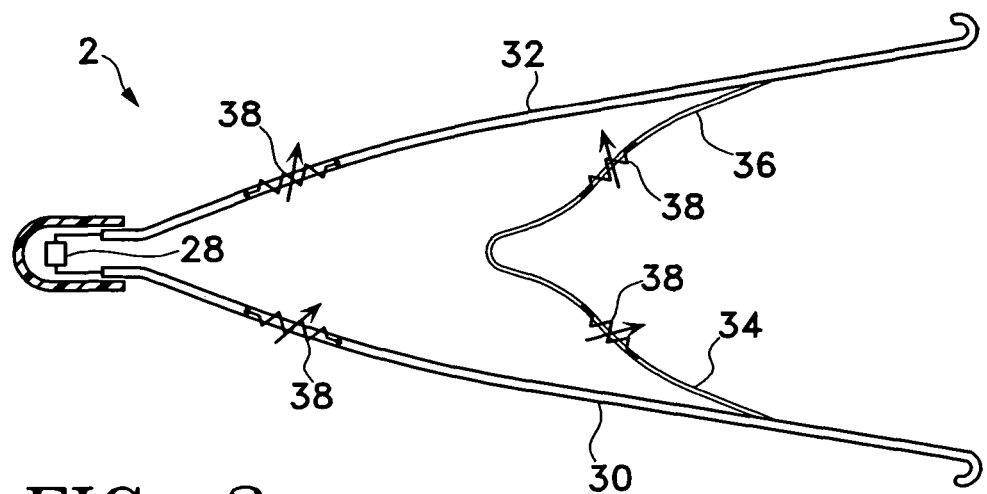
FIG. 2 is a circuit representation illustrating the variable resistive characteristics due to strain exerted on each of the legs and the corresponding conductive bridge.

Referring to FIG. 2, a circuit model illustrating the variable resistive characteristic of a pair of filter legs 30, 32 within a deployed filter 2 is shown. In this model each segment of the leg 30, 32 and each segment of the conductive bridge 34, 36 within the electric circuit loop is represented by a variable resister 38. Increase in strain in any of the segments will result in change in overall resistance and/or impedance of the circuit loop which is measured by the electronic measurement circuit 28 connected to the filter legs 30, 32. As one of ordinary skill in the art having the benefit of this disclosure would appreciate, various circuit configurations may be applicable for measuring the strain in the plurality of legs in a vessel filter. Selective examples of connections between the electronic measurement circuit and the filter legs are illustrated below.

Figure 3A:
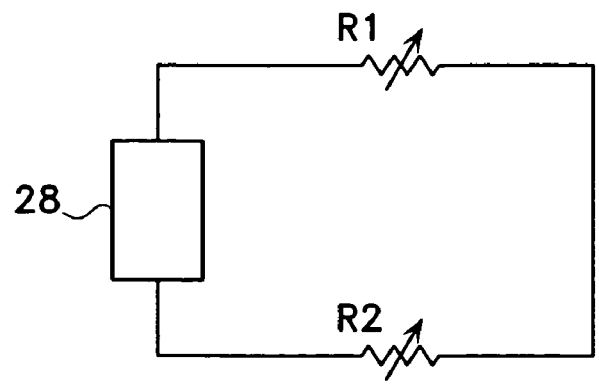
FIG. 3A illustrates one configuration where the electronic circuit is designed to measure the change in strain on the two filter legs.

In one variation, as shown in FIG. 3A, the strain in the filter legs is measured in pairs. R1 and R2 represent the variable resistive characteristics in a corresponding pair of filter legs. For each pair of filter legs that needs to be monitored, an electronic measurement circuit 28 is provided. In one configuration, each pair of adjacent filter legs is connected to a measurement circuit 28 such that for a six leg filter, five measurement circuits are provided. Each of the measurement circuits may transmit information regarding the strain experienced by its corresponding pair of legs to a receiving device at a different transmission frequency. A control circuit in the receiving device may poll the different measurement circuits to collect the data and then determine the strain distribution in the filter legs. Uneven strain distribution in the filter legs may suggest that the filter is misaligned with the blood vessel, or that the vessel filter has penetrated through or perforated the blood vessel wall. Alternatively, a control circuit may be implemented to collect strain information on the different pairs of filter legs and then transmit the data as a group to a remote receiving device.

Figure 3B:
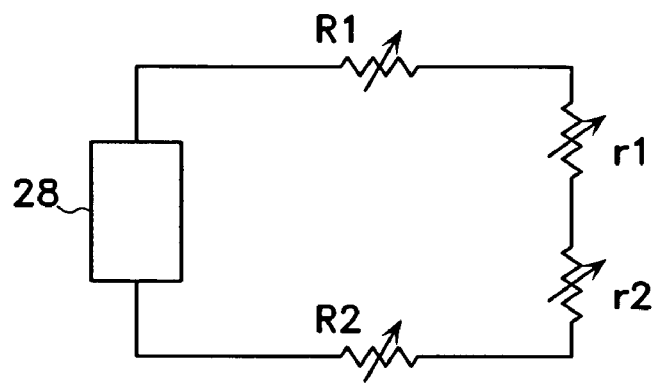
FIG. 3B illustrates another configuration where the conductive bridge is configured with a strain gauge material with resistive characteristics that are highly sensitive to changes in strain.

FIG. 3B illustrates a variation where the conductive bridge has two segments and each segment is sensitive to changes in strain. The variable resistive characteristics of the two conductive bridge segments are represented as r1 and r2. A thrombus may apply pressure directly on the conductive bridge and cause an increase in strain. The thrombus may also force the filter legs apart and indirectly extend the conductive bridge laterally and cause an increase in strain. Similar to the above configuration, each pair of filter legs R1, R2 and its corresponding bridge r1, r2 may be connected to a separate measurement circuit 28.

Figure 3C:
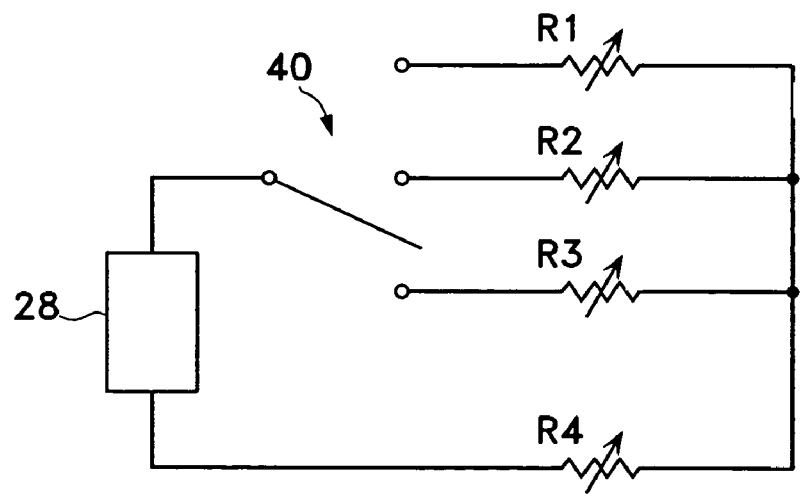
FIG. 3C illustrates another configuration where the electronic circuit for strain measurement is configured to measure the strain on selective pairs of filter legs independent of the other legs.
Figure 3D:
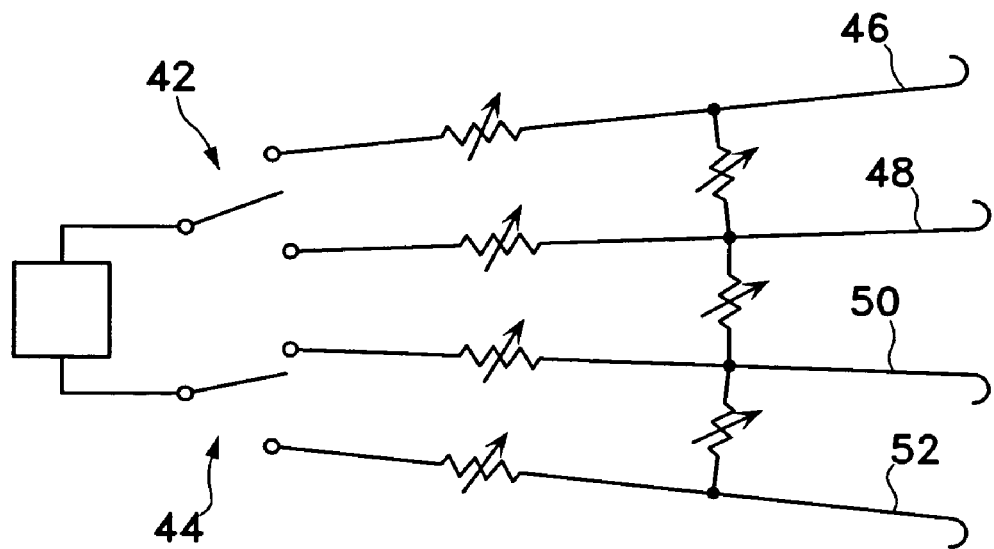
FIG. 3D illustrates another configuration where the electronic circuit for strain measurement is configured to measure the strain on each of the conductive bridges independently.
Figure 3E:
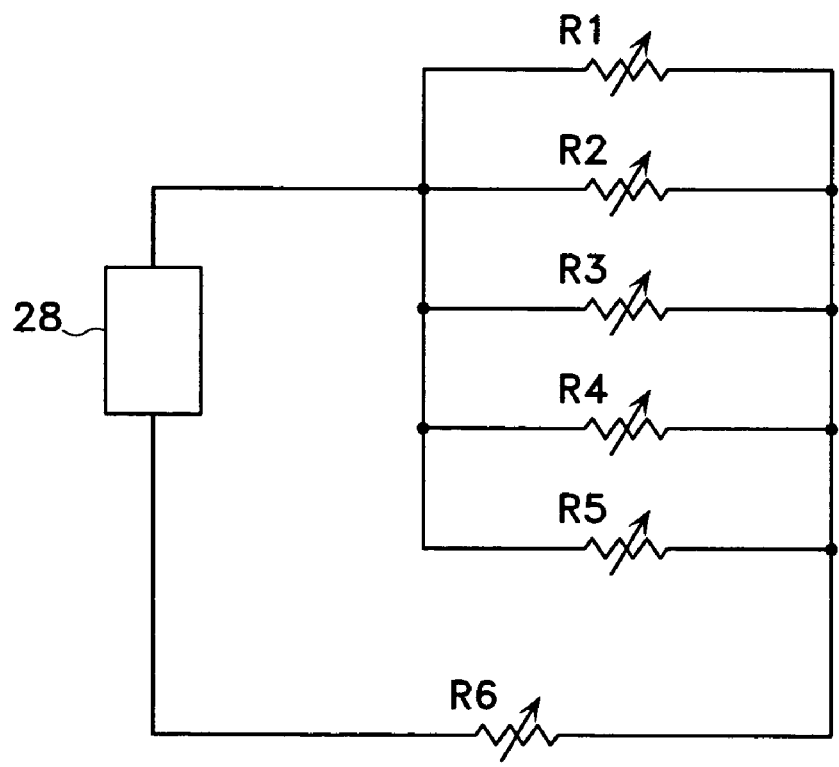
FIG. 3E illustrates another configuration where the filter legs are electrically connected in a parallel manner such that an electronic measurement circuit may be utilized to measure the strain on all the legs in the vessel filter as a single consolidated parameter.

In FIG. 3C, a variation utilizing a single measurement circuit 28 to measure the strain in the various filter legs 4 is shown. A switch 40 is provided such that different electric loops may be established to measure the resistance R1, R2, R3, R4 in the different filter legs. The switch may comprise electronic gates implemented on an integrated circuit. FIG. 3D illustrates another variation where a pair of switches 42, 44 are implemented to measure strain in the different pairs of filter legs 46, 48, 50, 52 selectively. FIG. 3E illustrates yet another variation where the electric connection between the legs are configured such that the strain in the various filter legs is measured simultaneously to determine the overall strain on the vessel filter. The overall strain on the vessel filter may correspond to the distension of the filter structure. In the example shown in FIG. 3E, the filter has six legs and their corresponding variable resistive characteristics in response to strain are represented by R1-R6. As one of ordinary skill in the art having the benefit of this disclosure would appreciate, electric measurement circuits 28 may be configured to support measurement of strain in filters with any number of legs, including those of configurations described herein.

Referring now to FIG. 4, another variation of a vessel filter 2 implementing a dual cone filter 54, 56 structure is shown. An electronic circuit 28 may be provided to measure the strain in one or more of the filter legs. Strain in both the distal 56 and proximal filters 54 may be measured. However, in this particular design, passive circuits are implemented to measure the strain on only the six distal filter legs 58, 60, 62, 64, 66, 68. The six distal legs are configured as three separate pairs for measurement. A simplified drawing illustrating the connections in the six distal legs 58, 60, 62, 64, 66, 68 is shown in FIG. 5A. The passive electronic circuits 70, 72, 74 are connected to the three pairs of distal legs 58, 50, 62, 64, 66, 68 as shown in FIG. 5B. Each of the passive circuits 70, 72, 74 may be configured with a different resonance frequency such that a remote device with an interrogation circuit may utilize the different resonance frequency to query each of the three passive electronic circuits 70, 72, 74 independently of each other. The data collected from the three passive electronic circuits 70, 72, 74 may be utilized by a control circuit in the remote device to determine whether there are changes in the overall strain experienced by the filter legs and the strain distribution between the different pairs of filter legs.

Although in the example discussed above, the plurality of legs forms two filter baskets along the longitudinal length of the device, one may configure the device with only one filter basket, or alternatively with three or more filter baskets. In addition, the device may be configured with three or more legs forming each basket and is not limited to the six-legged basket as shown above. Also discussed earlier, hooks 76 may be provided on the distal end of each leg. As one of ordinary skill in the art would appreciate, the precise length and angle of the hooks 76 may be designed to provide secure attachment to the vessel wall without causing perforation or tearing. Moreover, hooks may be provided on all the distal legs or only on some of the distal legs. Hooks may also be provided on the proximal legs if desired. Furthermore, secondary struts, which may also serve as a conductive bridge, may be provided for interconnecting two or more of the radially expandable legs. The secondary struts may increase wiring density for each filter basket, which may in turn increase the filters capability to capture smaller particles.

Figure 6:
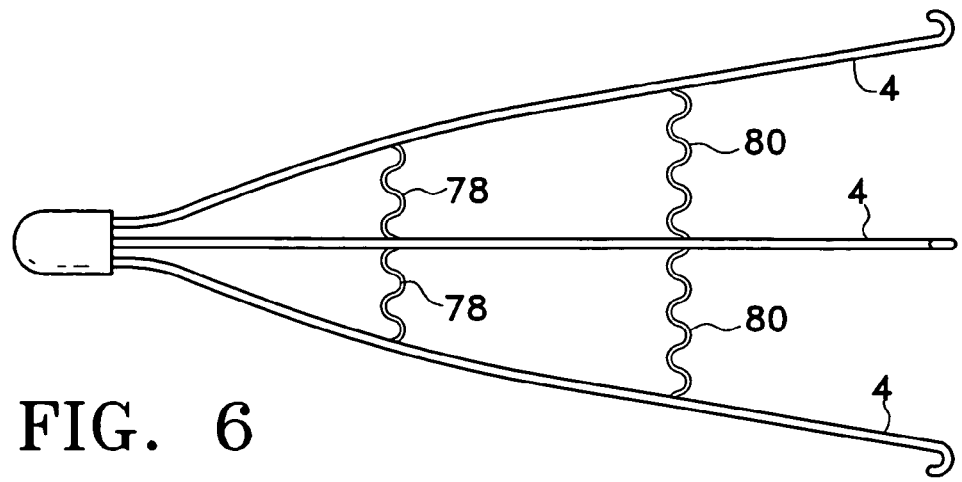
FIG. 6 illustrates another design, where pairs of strain gauge are implemented between the adjacent legs to measure the distention of the vessel filter due to trapping of thrombus within the vessel filter.
Figure 7A:
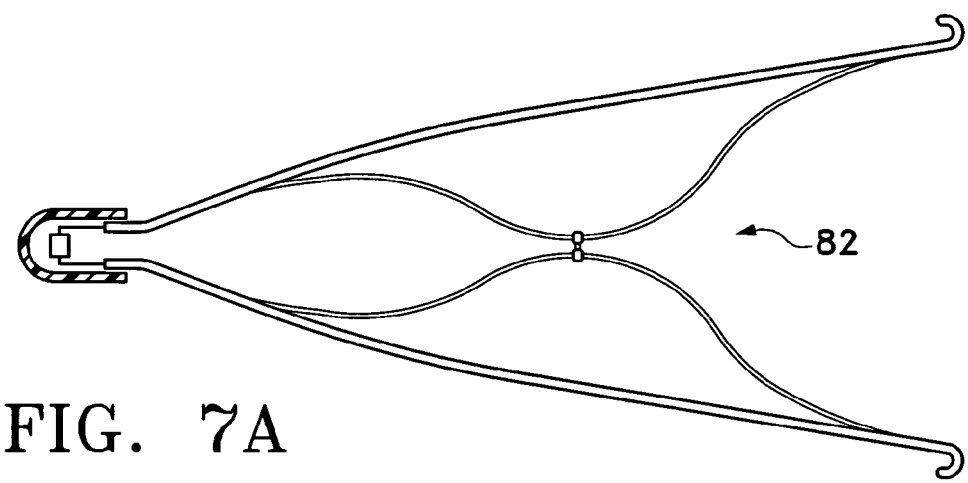
FIG. 7A illustrates another variation of the vessel filter where the conductive bridge comprises interlinks.
Figure 7B:
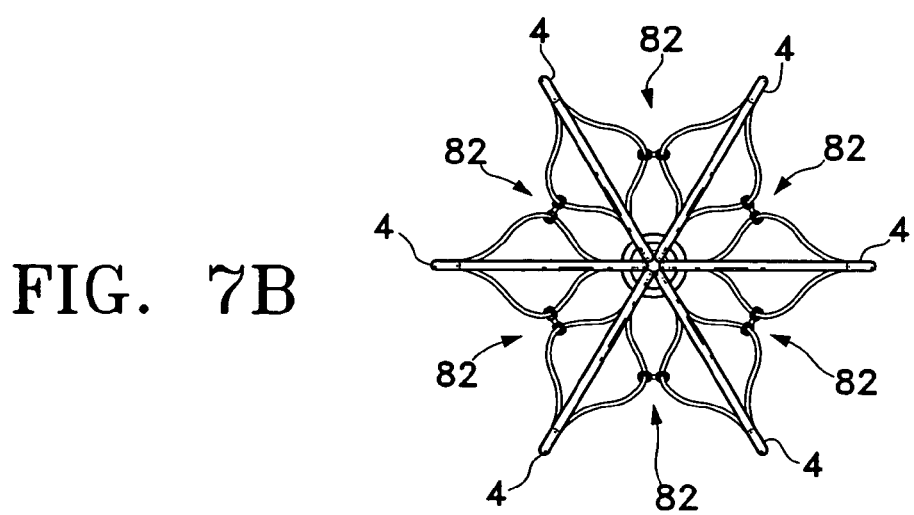
FIG. 7B is a frontal view of an expanded vessel filter implementing the interlinked bridge design shown in FIG. 7A. The vessel filter is viewed from the proximal end (i.e., head end) down the longitudinal axis of the filter toward the distal end of the vessel filter.

In addition, two or more conductive bridges may also be implemented. For example, as shown in FIG. 6, a pair of conductive bridges 78, 80 is implemented between each pair of adjacent filter legs 4. Each segment of the conductive bridges may also be configured as a strain gauge. FIG. 7A illustrates another variation where the conductive bridges are configured as interlinks 82. FIG. 7B shows a six-legged filter 84 utilizing interlined 82 connections between the filter legs 4.

Figure 8A:
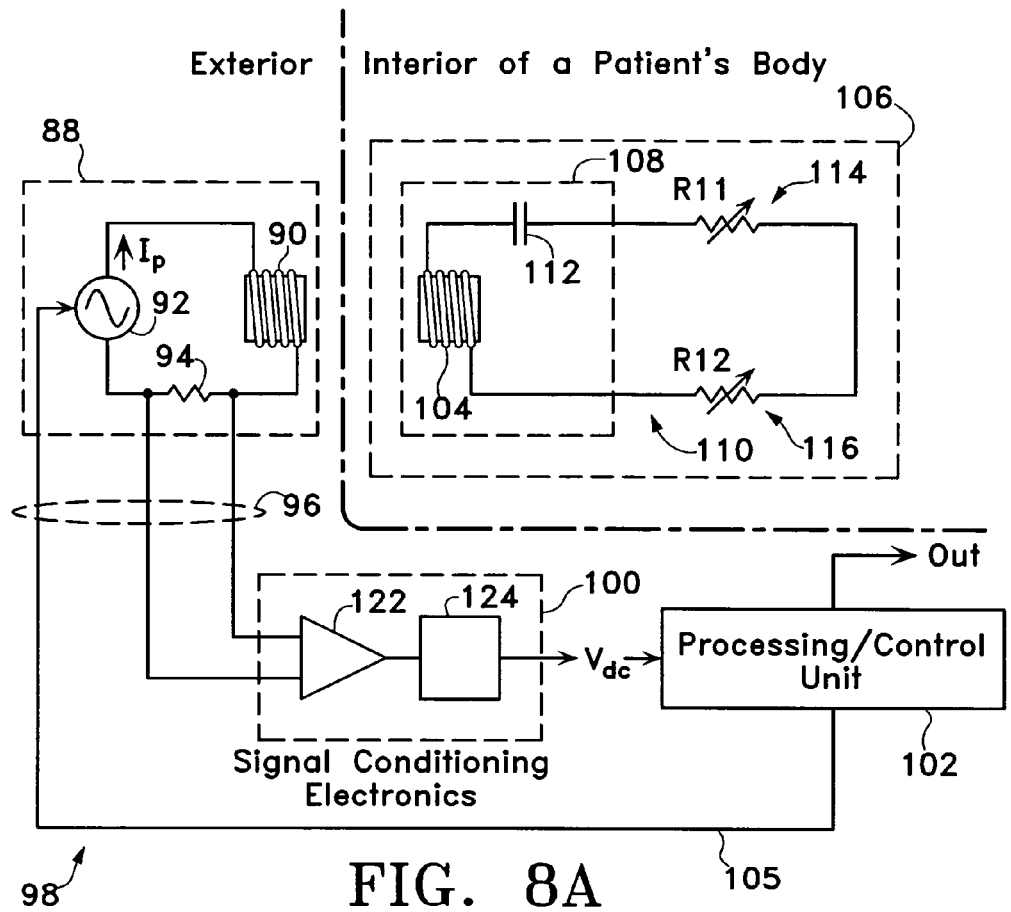
FIG. 8A illustrates one variation of a passive circuit system for measuring the strain on the vessel filter legs by remotely energizing a passive measurement circuit and detecting changes in the passive measurement circuit due to resistive changes on the vessel legs as a result of change in strain.

As discussed above, various passive sensing circuits may be implemented to measure the strain in the filter legs. Passive circuits, such as those described in U.S. Pat. No. 5,581,248, U.S. Pat. No. 6,206,835 B1, U.S. Pat. No. 6,682,490, and U.S. Patent Application No. 2004/0082867 A1, each of which is incorporated by reference in its entirety, may be used to measure the strain in the vessel filters described herein. An example of a passive circuit implemented to measure the strain in the filter legs is shown in FIG. 8A. The exciter/ interrogator unit 88 includes an exciter/interrogator coil 90, a voltage controlled oscillator 92, and a load sensing resistor 94. The oscillator 92 provides an excitation signal to the exciter/interrogator coil 90 and the load sensing resistor 92 which are coupled in series. The exciter/interrogator unit 88 is coupled via the cable 96 to the main circuitry 98 which includes signal conditioning electronics 100 and a data processing and control section 102. The data processing and control section 102 produces a control signal on line 105 for controlling the frequency and the magnitude of the excitation signal that the oscillator 92 applies to the exciter/interrogator coil 90. The exciter/interrogator coil 90, sensing resistor 94 and oscillator 92 provide a resonant exciter/interrogator circuit that is used to induce currents in a coil 104 within the implant device 106 in order to perform interrogation.

The electronic measurement circuit 108 embedded in the vessel filter is connected to two of the filter legs. The variable resistive characteristics of the filter legs are represented as R11 and R12. The electronic measurement circuit 108 comprises a sense coil 104 for receiving electromagnetic energy from the exciter/interrogator unit 88. The sense coil 104 may be integrally secured to a surface on the sleeve of the vessel filter. The sense coil 104 is part of a passive resonant sensing circuit 110 which includes, for example, a capacitor 112 and the strain gauges (i.e., the filter legs to be measured) 114, 116 in electrical series with the sense coil 104. In applications where sensors are applied on the vessel filter to measure strain or distension of the vessel filter, the electronic measurement circuit 108 may be connected to the sensor instead of the vessel filter legs. The sensor can be any sensor which produces a variable impedance (e.g., resistance, capacitance or inductance), or which produces an output that can be converted into a variable impedance that can change or modulate the impedance of one or more of the resonant circuit components. The sensor can be any of a variety of known types of sensors which may be used to sense the condition of the vessel filter. Such parameters to be measured may include, but are not limited to, strain on the sensor legs, force or pressure on the filter legs, shear stress on the filter legs, displacement of the filter legs, distension of the vessel filter, presences of a blood clot in the vessel filter. Exemplary sensor types include electrical sensors, piezoelectric sensors, sonic sensors, optical sensors, microfluidic sensors, chemical sensor, membrane, strain gauge, thermal sensors, pressure sensors, magnetohydrodynamic sensor, magnetic sensors, magnetostrictive sensors, biological sensors, microelectromechanical sensors (MEMs), etc. The sensor itself may be characterized as an impedance-based sensor whose resistance, capacitance and/or inductance varies directly with respect to frequency as a function of the sensed parameter, or another type of sensor whose output can be converted into a variable impedance.

As shown in FIG. 8A, the sensors 114, 116 (i.e., the filter legs) are represented by a variable resistance R11, R12, which varies based on the strain exerted on the filter legs. In an alternative variation, the sensor may provide a capacitance, inductance and/or resistance which varies based on a sensed parameter. When a sensor is combined with the sense coil 104 alone or together with one or more elements (e.g., capacitor 112), a resonant sensing circuit 110 (e.g., LC or LRC) may be obtained.

The sensing circuit 110 exhibits a resonant frequency which is defined as the frequency which is the point of maximum sensitivity to changes in the excitation current $I_p$ for a given change in the impedance of the filter legs R11, R12. The resonant frequency $f_s$ is determined by the sum total of the reactive elements of the circuit, which includes the inductance 118 of the sense coil 104, and the inductance 120 of the exciter/interrogator coil 90, as well as the capacitance 112 and parasitic capacitances $C_{p1}$ and $C_{p2}$, shown in FIG. 8B, and the value of a coupling constant K. The amplitude of the current through the coil 104 is also a function of the sensors 114, 116, particularly at the resonant frequency of the sensing circuit 110. When the exciter/interrogator coil 90 has an AC signal applied, current in the primary or exciter/interrogator coil 90 induces current in the secondary or sense coil 104, as in an air gap transformer. This current in the sense coil 104, however, is reflected back to the exciter/interrogator coil 90 by the mutual coupling of the two coils. The sensing resistor 94 is used to detect the current in the exciter/interrogator coil 90.

When the excitation frequency is approximately at the resonant frequency of the sensing circuit 110, the current in the exciter/interrogator coil 90 changes maximally in relation to the value of the filter legs 114, 116. Thus, the condition of the filter legs can be determined as a function of the detected current in the exciter/interrogator coil 90. Using an amplifier 122, the signal conditioning electronics 100 amplify the voltage developed across the sensing resistor 94 by the exciter/interrogator circuit current $I_p$. This amplified voltage is then rectified and low pass filtered via a rectifier and low pass filter circuit 124 to provide a DC voltage output $V_{dc}$. The control circuit 102 then uses the DC value to determine the state or output of the filter legs 114, 116.

Figure 8B:
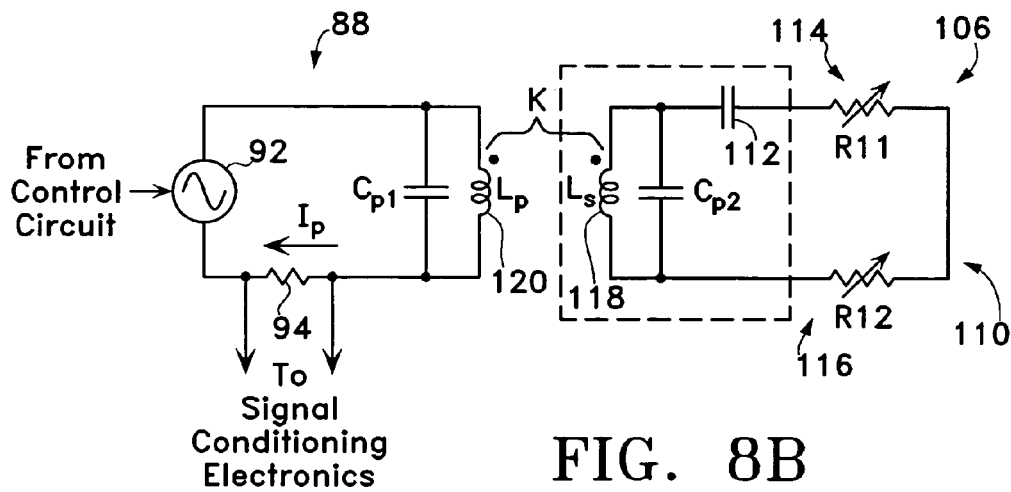
FIG. 8B illustrates another representation of a passive circuit measurement system showing the inductive elements of the circuit.

FIG. 8B provides a more detailed circuit model of an exciter/interrogator unit 88 and the implant device 106. As shown, the exciter/interrogator unit 88 includes the exciter/interrogator coil 90 that has a determinable inductance $L_p$. The coil 90 and associated components of the exciter/interrogator unit 88 also will exhibit an overall parasitic capacitance, $C_{p1}$, that appears in parallel with the coil inductance. The exciter/interrogator unit 88 further includes the variable frequency oscillator 92 and the sensing resistor 94 used to sense the primary or excitation current $I_p$. Thus, all components in the exciter/interrogator unit 88 are known quantities for each application.

The resonant sensing circuit 110 includes the sense coil 104 which has a determinable inductance, $L_s$, in one embodiment; or in another embodiment an inductance which varies in relation to the sensed parameter. In such an embodiment, the sense coil 104 itself forms part of the sensing element. The sense coil 104 also has an associated parasitic capacitance, which parasitic capacitance is in effect part of the capacitance $C_{p2}$ which is a discrete capacitor selected to optimize the sensitivity of the device 106 to changes in the value of the sensing elements 114, 116. In other words, the value of $C_{p2}$ can be selected, such as based on experimental data for specific circuits, to maximize the current $I_p$ induced in the exciter/interrogator unit 88 as a function of changes in the resistance of the sensing element 114, 116. The sensing circuit 110 also includes the additional discrete capacitor 112 which is selected to adjust the frequency at which the change in current versus change in sensing element resistance ratio is optimized. The basic operation of a passive circuit system 30 is explained more fully in U.S. Pat. No. 5,581,248, which is incorporated herein by reference in its entirety.

Figure 9A:
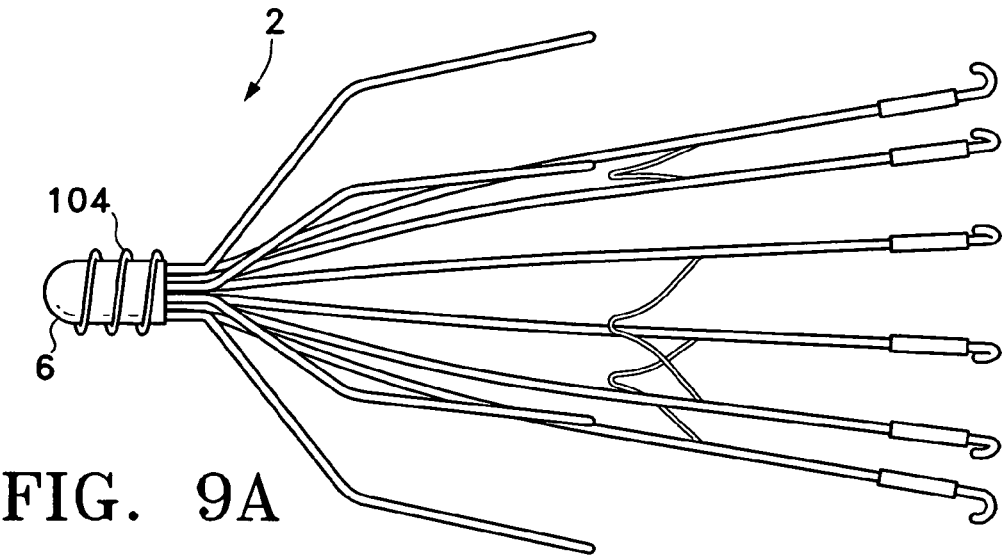
FIG. 9A illustrates one variation where the inductive circuit loop is provided on the circumferential surface of the filter sleeve.
Figure 9B:
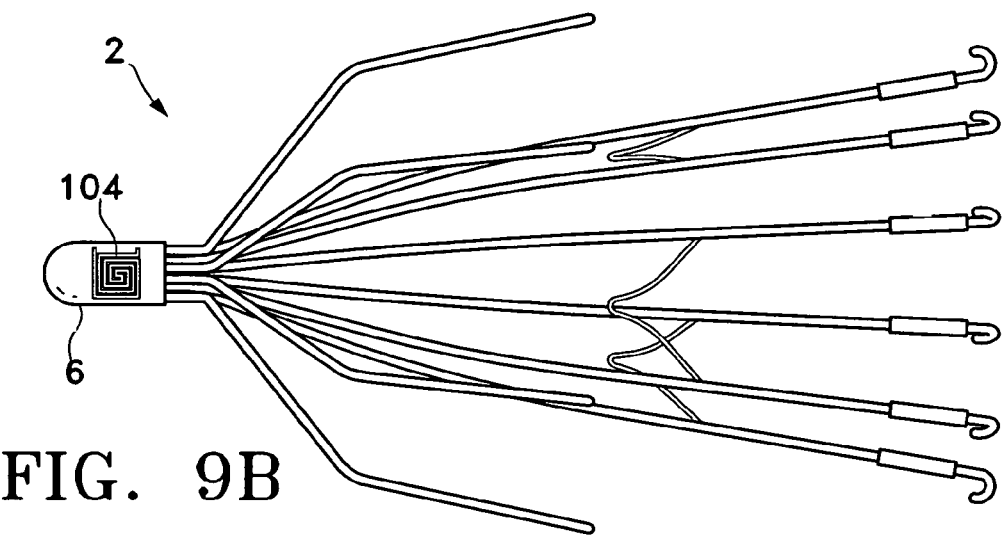
FIG. 9B illustrates another design where the inductive circuit loop is provided on a surface on the vessel filter sleeve.

The sense coil may be integrated with the vessel filter through various methods well known to one of ordinary skill in the art. An example of sense coil integration is shown in FIG. 9A where the sense coil 104 is wrapped around the sleeve 6 of the filter head. The coil 104 may be also be placed on the inner surface of the sleeve or be embedded within the sleeve. In another variation, the sense coil 104 is printed on a surface on the filter sleeve 6 as shown in FIG. 9B.

Figure 10:
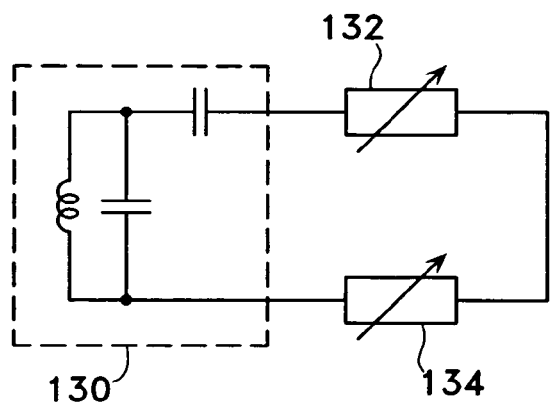
FIG. 10 illustrates another design variation where sensors are connected to the legs of the vessel filter to measure strain and/or strain on the vessel filter legs. In the configuration shown in FIG. 10, a passive circuit is utilized to measure changes in the sensors and transmit data to a remote device.

In another aspect of the invention, a sensor is placed on the vessel filter to determine the condition of the vessel filter. For example, a strain gauge may be placed on the vessel legs to detect the strain and/or distension of the legs. Although both passive and active electronic circuit may be implemented to measure changes detected by the sensor, a passive circuit is used in the preferred design. For example, a passive circuit 130 shown in FIG. 10 may be utilized to measure the two sensors 132, 134 which are placed on the vessel filter.

Figure 11A:
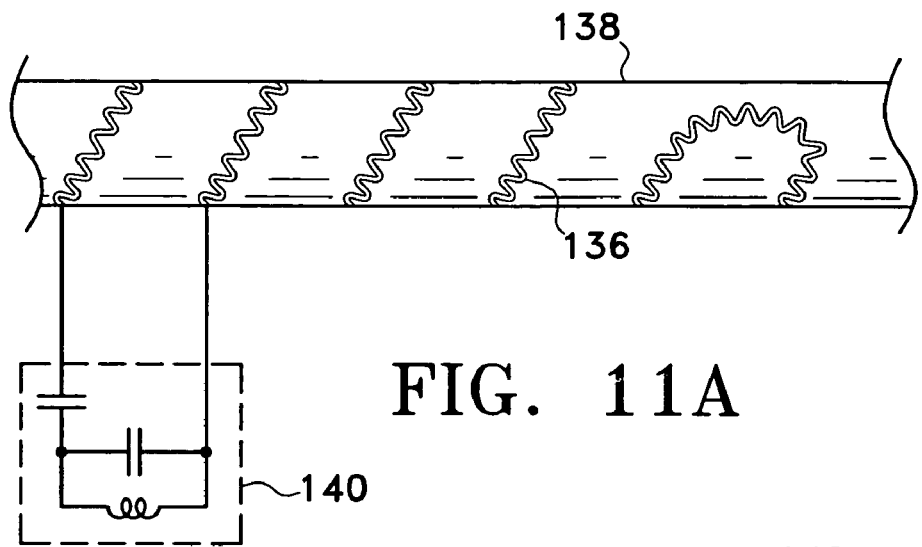
FIG. 11A illustrates a design variation where a strain gauge is wrapped around a filter leg on the vessel filter in a helical manner for measuring the distension of the leg due to pressure exerted on the filter leg. The figure also illustrates a corresponding passive circuit for measuring the strain gauge.
Figure 11B:
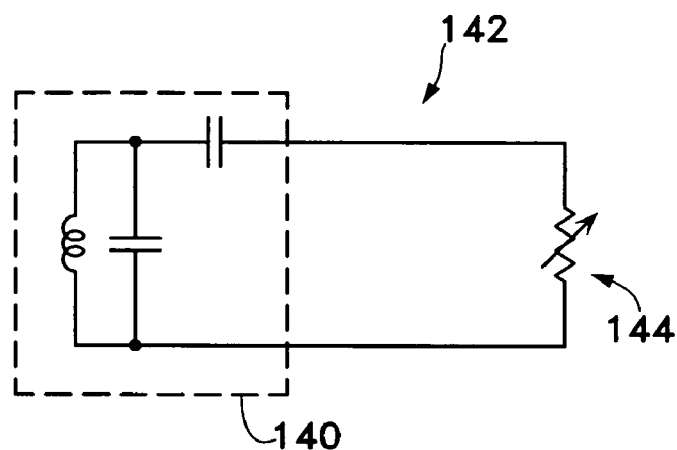
FIG. 11B is a circuit diagram representing the electrical connection of the strain gauge measurement circuit shown in FIG. 11A. The strain gauge is represented by a variable resister in the diagram.

In one variation, the sensor comprises a strain gauge 136 wrapped around a vessel leg 138 in a helical manner, as shown in FIG. 11A. A pressure applied on the filter leg that causes distension or bending of the filter leg can lead to the strain on the strain gauge 136 to increase. This change in strain may be measured with an exciter/interrogator circuit interacting with the passive electronic measurement circuit 140 that is connected to the strain gauge 136 on the filter leg 138. FIG. 11B illustrates the complete passive circuit loop 142, with the strain gauge 136 being repressed as a variable resister 144 that changes resistance in response to strain exerted on the strain gauge 136.

Figure 11C:
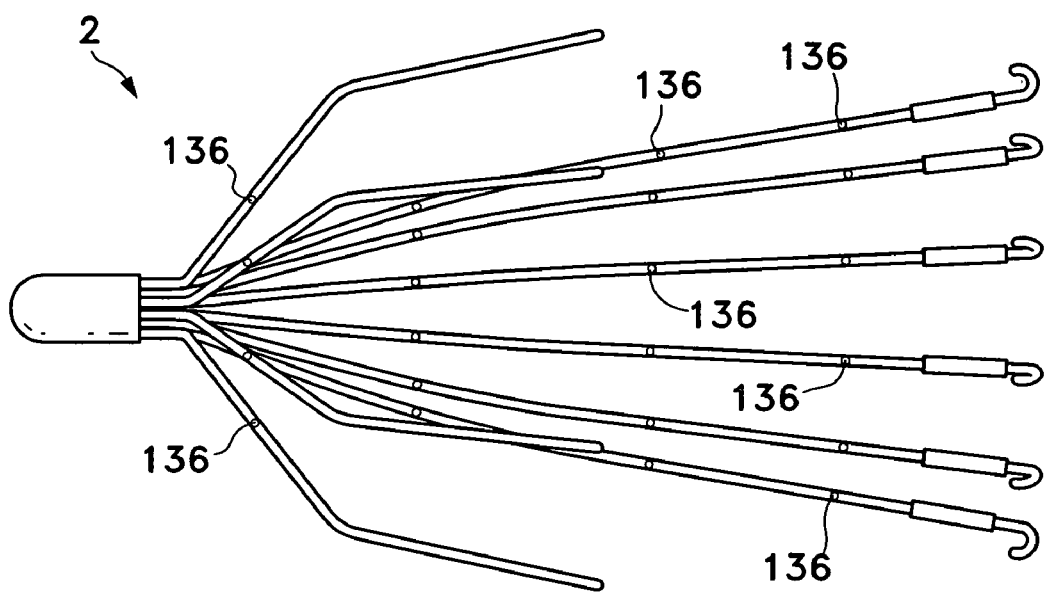
FIG. 11C illustrates a variation where multiple sensors are implemented on the vessel filter to determine the condition of the filter.

A strain gauge may be implemented on one or more of the filter legs to detect distension of the vessel filter. The strain gauge may be placed on the filter legs in various patterns and configurations well known to one of ordinary skill in the art. For example, the strain gauge material may be deposited on the filter legs through plasma deposition. The strain gauge material may also be embedded on or within a polymer coating placed on the surface of the vessel filter. In addition, two or more strain gauges 136 may be placed on different portions of a given leg to monitor strain distribution along the length of the filter 2, as shown in FIG. 11C. Furthermore, other sensors that are well known to one of ordinary skill in the art may also be implemented on the vessel filter to monitor the condition of the filter legs. For example, pressure sensors may be distributed along the vessel filter body to detect pressure distribution on the body of the vessel filter. In another design, wire mounted pressure sensors may be implemented on the vessel filter legs. In yet another design, a sensor similar to the PressureWire® Sensor (RADI Medical Systems) may be integrated within the vessel filter.

Figure 12:
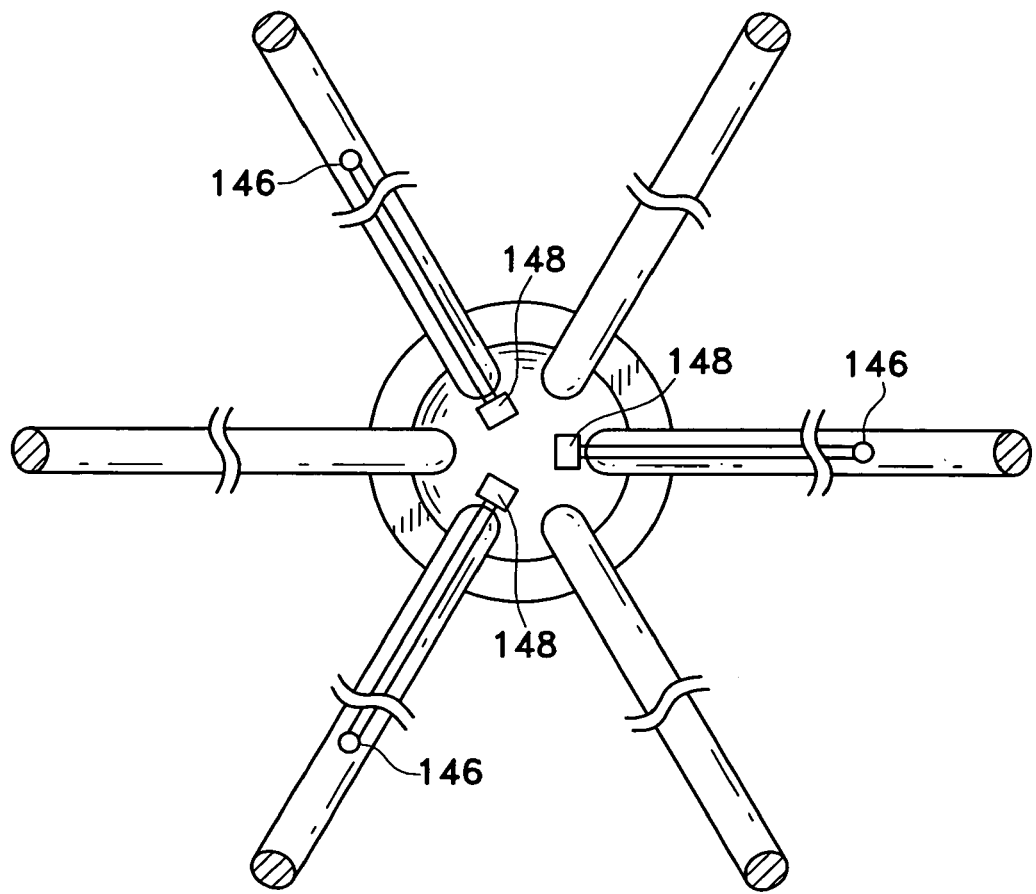
FIG. 12 is another design variation where sensors are provided on the vessel filter to detect the presence of thrombus within the vessel filter.

In another aspect of the invention, a sensor 146 is provided on the vessel filter to detect the presence of a thrombus or other objects that have been captured within a deployed filter. For example, as shown in FIG. 12, pressure sensors 146 are placed on the legs of the vessel filter to detect the presence of blood clots. A passive or active circuit 148 may be implemented to drive the sensor and detect signals provided by the sensor 146. Other sensors 146 that are well known to one of ordinary skill in the art may also be implemented on the vessel filter to detect thrombus.

Figure 13:
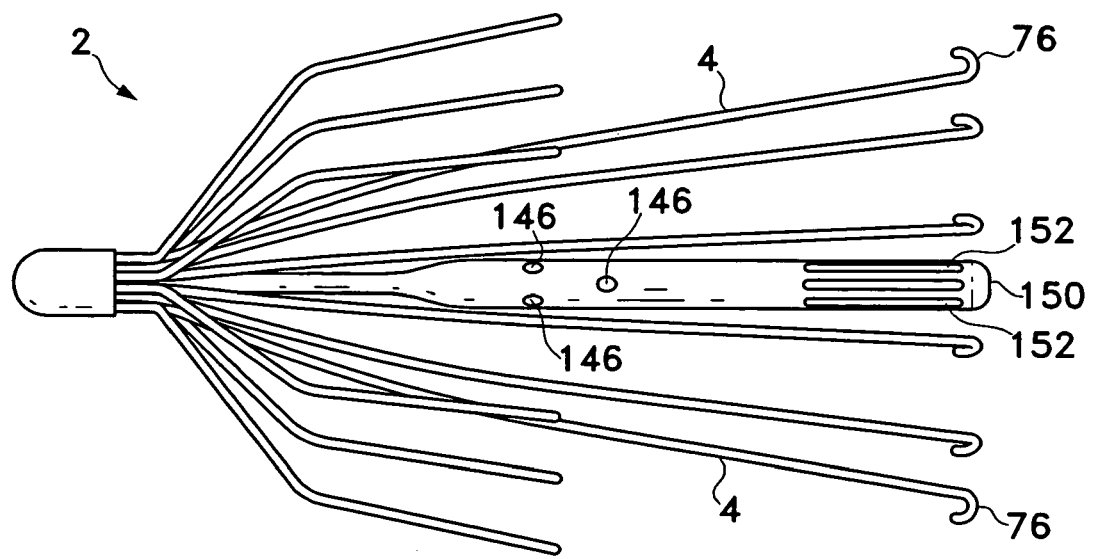
FIG. 13 is yet another design where the vessel filter is configured with a center post with embedded sensors to detect the presence of thrombus within the vessel filter. The center post may be further configured with slots or grooves to prevent the entanglement of the filter legs when the filter legs are collapsed onto the center post in the compressed configuration. The rod may also serve as an antenna for transmission of electrical signals.

In another variation, the vessel filter comprises a center post 150 extending along the longitudinal axis of the vessel filter 2, as shown in FIG. 13. Sensors 146 placed on the center post 150 may be used to detect the presence of thrombus. An electronic circuit may be provided either within the center post 150 or embedded in the sleeve of the vessel filter for detecting signals from the sensors. The center post 150 may be configured with slots 152 for receiving the hooks 76 on the filter legs 4 when the filter legs 4 are compressed onto the center post. The slots on the center post may be adapted to prevent the filter legs 4 hooks from entanglement while the filter 2 is in the compressed position, as described more fully in pending U.S. patent application Ser. No. 10/912,601, which is incorporated herein by reference in its entirety.

Figure 14A:
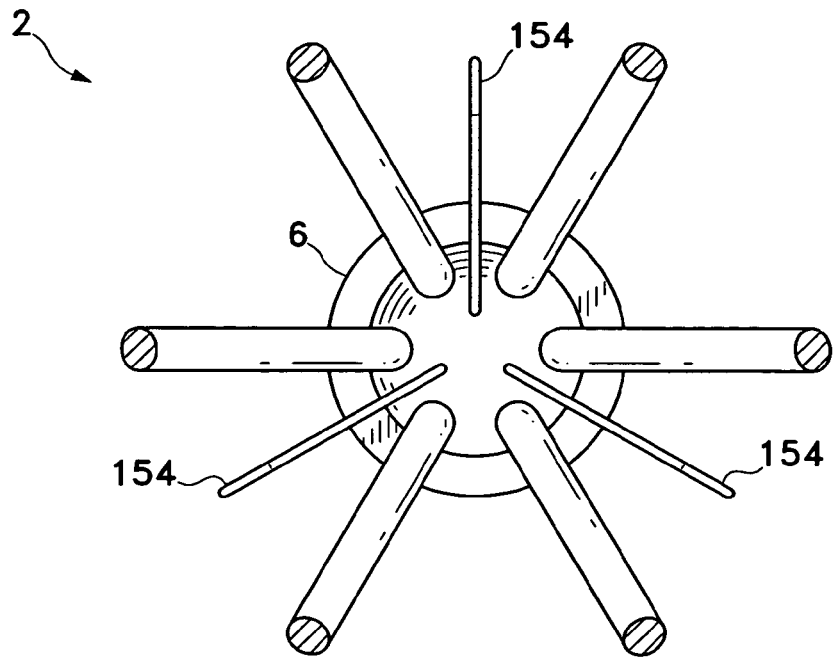
FIG. 14A illustrates another variation where sensing members extending from the sleeve (i.e., head portion) of the vessel filter are provided to detect the presence of blood clots within the vessel filter.
Figure 14B:
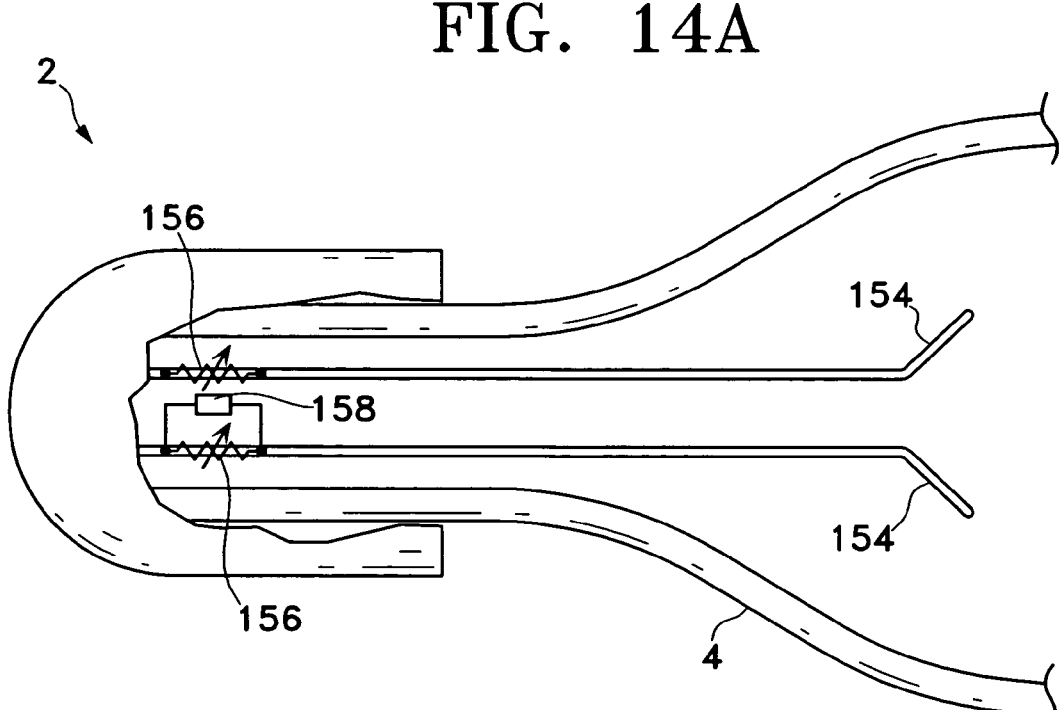
FIG. 14B illustrates one particular design where the proximal portion of the sensing members are connected to strain gauges for detecting or distension of the sensing members. A passive circuit may be implemented to measure the variable resistance of the strain gauges.

In yet another variation, sensing members 154, (which may be whisker-like extension elements) extending from the sleeve 6 of the vessel filter 2 are utilized to detect the presence of thrombus in the deployed filter. An example, illustrated in FIG. 14A, shows the sensing members 154 extending from the base of the sleeve 6 towards the distal end of the filter 2. When a blood clot is captured by the vessel filter 2 it will glide towards the sleeve 6 and engage the sensing members 154. FIG. 14B illustrates one variation of a circuitry for detecting the presence of the blood clot. In this variation, the proximal end of the sensing member is connected to a strain gauge 156. The blood clot applies pressure on the sensing member and a force is transmitted through the sensing element to the strain gauge 156. An electronic measurement circuit 158 is used to measure the strain gauge. The electronic circuit 158 may be either a passive or an active circuit.

Figure 14C:
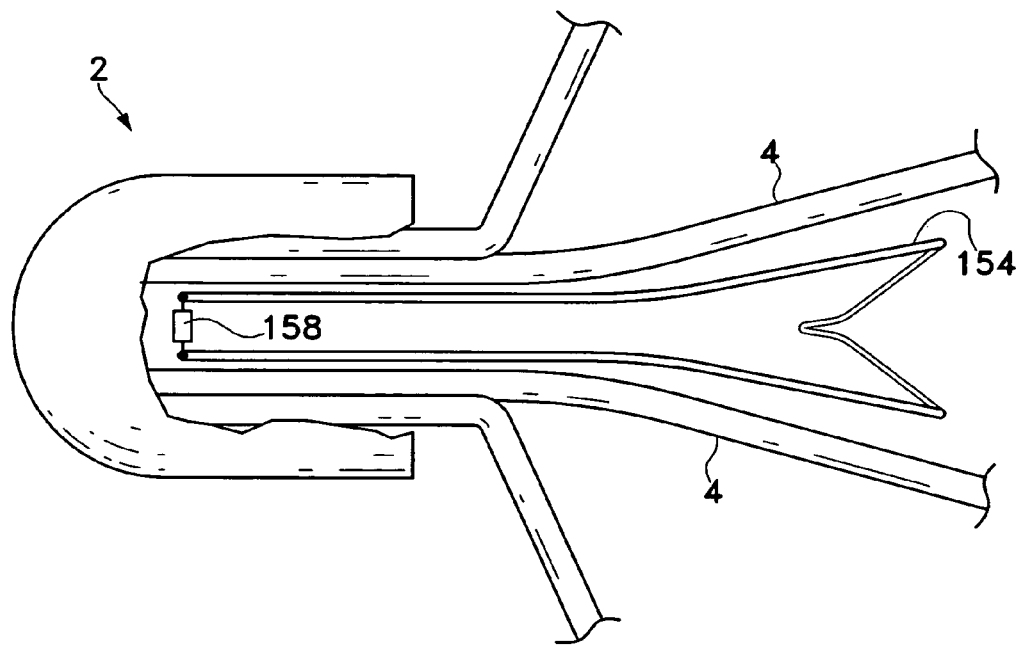
FIG. 14C illustrates another configuration of the sensing members where an electronic circuit is provided to measure the strain on the sensing members by directing current through the sensing members and measuring the changes in the strain of the sensing members.
Figure 14D:
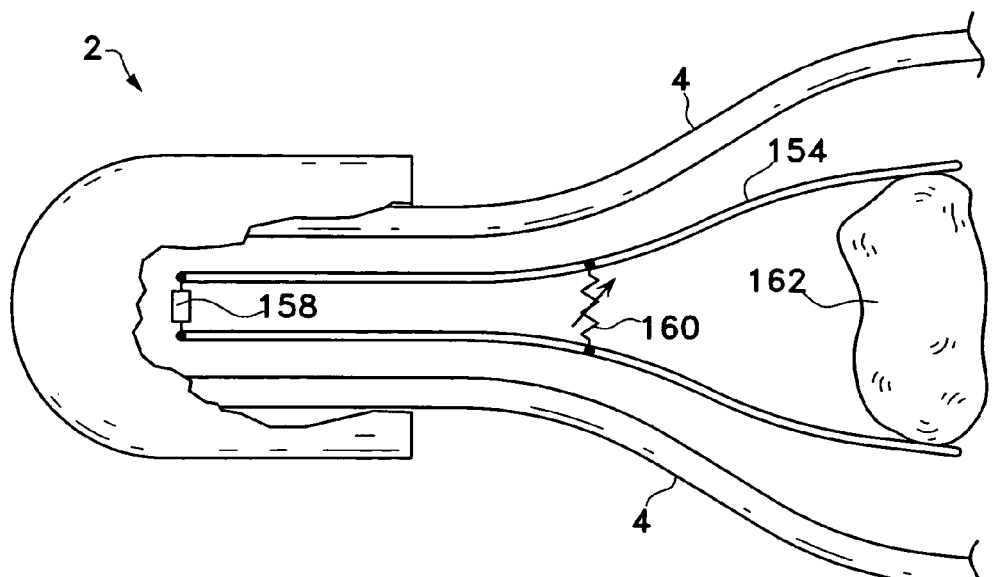
FIG. 14D illustrates another variation where a strain gauge is provided between a pair of sensing members to measure the displacement and/or distension of the sensing members due to the presence of a blood clot in the vessel filter. The figure is shown within a blood clot engaging the sensing members.

In another variation, the sensing member 154 comprises a strain gauge material itself. An electronic measurement circuit 158 is connected to the sensing member 154 in a serial manner to detect changes in the sensing member as shown in FIG. 14C. In yet another design, a strain gauge 160 is placed between the two sensing members 154 as shown in FIG. 14D. The blood flow forces the blood clot 162 onto the sensing members 154, which in turn extend the strain gauge 160. An electronic measurement circuit 158 is connected to the proximal end of the sensing members 154. The electronic circuit 158 is configured to measure the strain experienced by the strain gauge 160.

Figure 15A:
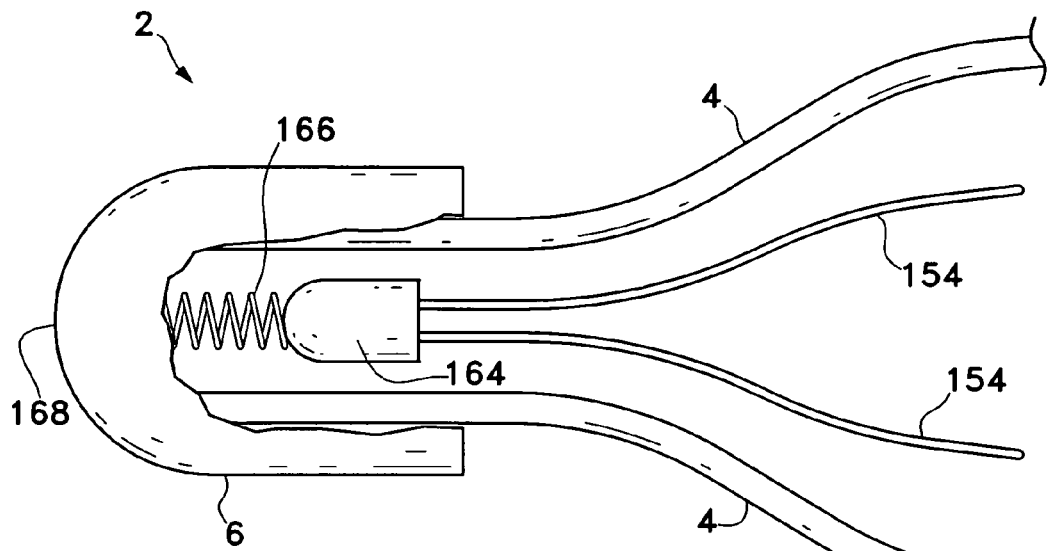
FIG. 15A illustrates another variation of a vessel filter with integrated sensing members where the presence of blood clots can cause the displacement of the sensing members.
Figure 15B:
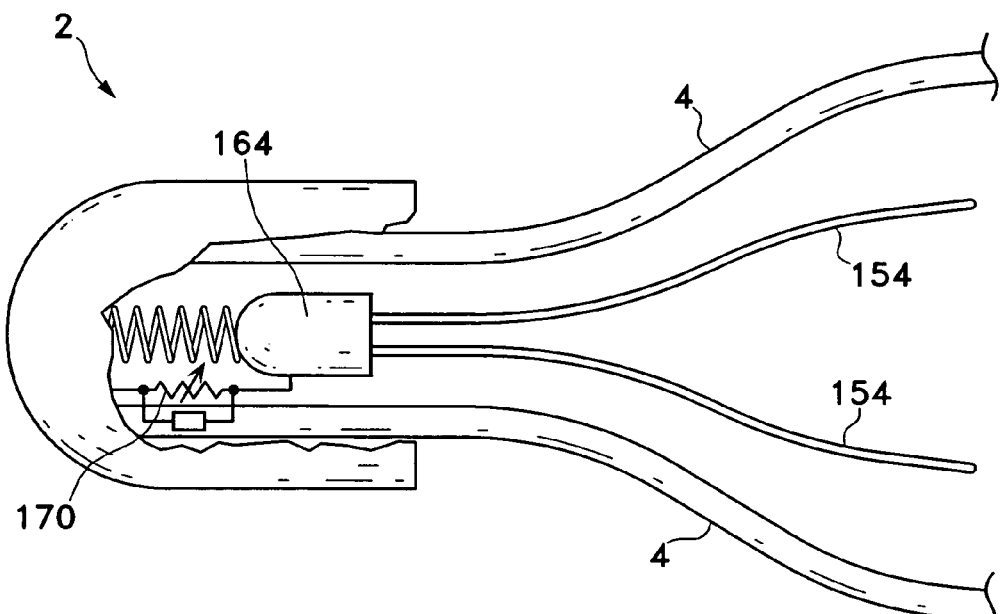
FIG. 15B illustrates a design where a strain gauge positioned parallel to a spring, which supports the sensing members, is implemented to measure the displacement of the sensing members.

In yet another design variation, the sensing members 154 are connected to a hub 164 that can be moveably displaced within the sleeve 6 of the vessel filter 2, as shown in FIG. 15A. A spring 166 or other elastic material positioned between the hub 164 and the top surface 168 of the sleeve keeps the tip of the hub 164 from contacting the top surface 168 of the sleeve 6. A trapped blood clot can force the hub 164 to compress the spring 166 and displace the hub 164 toward the proximal direction of the filter 2. A sensor may be implemented to measure this displacement. FIG. 15B illustrates one variation where a strain gauge 170 is placed at the proximal end of the hub 164 to measure the displacement of the hub.

In another variation, illustrated in FIG. 16, each of the sensing members 154 is connected to a microelectromechanical sensor 172 positioned within the sleeve 6 of the vessel filter. The microelectromechanical sensor 172 is configured to detect the movement of the sensing member 154 in the longitudinal direction and in the horizontal direction. Objects trapped within the vessel filter 2 will force the sensing members 154 to move, and such movement can be detected by the microelectromechanical sensor 172. As discussed above, an active or passive measurement electronic circuit may be utilized to receive signals from the microelectromechanical sensor. Although in the above examples two sensing elements are illustrated, one of ordinary skill in the art would appreciate that one, three or more sensing elements may be implemented in these devices.

In another aspect of the invention, shown in FIG. 17, a remote monitor 180 is utilized to detect the position of the vessel filter 2 within the patient's body 182 to determine whether the implanted vessel filter has migrated from its original implant location. An electronic circuit embedded in the vessel filter 2 is configured to transmit electromagnetic signals to a monitor 180, such that the monitor can determine the position of the vessel filter 2. Although active transmission circuits may be used, preferably a passive circuit is used. In a passive circuit configuration, the monitor 180 is configured to transmit an electromagnetic energy to the passive circuit through methods well known to one of ordinary skill in the art. The signals directed back to the monitor from the passive circuit allows the monitor 180 to determine the location of the vessel filter. A reference beacon 184 is provided so the monitor 180 can determine a reference position and calculate the position of the vessel filter 2 relative to the reference beacon 184. Preferably, the reference beacon 184 has an active circuit that transmits electronic signals to the monitor 180. The reference beacon 184 may be placed at a position on the patient's body that is in a relatively fixed position. For example, when the patient 186 is lying flat on a flat surface 188, the reference beacon 184 may be placed at the heel of the foot 190, next to the tip of the toe 196 and vertically aligned with the heel of the foot 190, next to the tip of the tail bone 192, or be secured between teeth 194.

In one variation, when there are no obstructions between the monitor 180 and the reference beacon 184, infrared light, laser or ultrasound may be implemented to emit from the reference beacon for identifying its position. Alternatively, the monitor 180 may emit a radio, light or ultrasound energy towards the reference beacon 184 and/or the vessel filter 2, and relying on the reflected energy to determine the distance and/or location of the reference beacon 184 and/or the vessel filter 2. In another design, the monitor 180 sent out an interrogating signal towards the reference beacon 184 and/or the vessel filter 2. In response to the interrogating signal the reference beacon 184 or the vessel filter 2 may send back a responding signal. The monitor 180 may then calculate the time between sending of the interrogating signal and receiving of the responding signal, taking into account the delays in electronic circuit response time, and determine the distance between the monitor 180 and the reference beacon 184 or the vessel filter 2. The interrogating signal may be transmitted in various form of energy (e.g., light, electromagnetic wave, sound, etc.). The responding signal may also be transmitted in various form of energy (e.g., light, electromagnetic wave, sound, etc.).

In one variation, the monitor 180 is configured to determine the relative position between the reference beacon 184 and the implanted vessel filter 2 through electromagnetic signals transmitted from both the reference beacon and the vessel filter. In another variation, the monitor 180 is configured to detect the implanted vessel filter 2, and as the monitor 180 is moved about the surface of the patient's body the monitor 180 indicates its closeness to the vessel filter. Once the monitor 180 (positioned on the frontal surface of the patient) is directly on top of the filter, it may then calculate its position relative to the reference beacon 184. A measurement is made immediately after the implantation of the vessel filter, and a subsequent measurement may be compared with the data collected post-implantation to determine if the filter has migrated within the blood vessel. The monitor may further comprise memory to record and compare measurements to determine whether the vessel filter has migrated. One of ordinary skill in the art having the benefit of this disclosure herein would appreciate the device location detection monitor describe above may be adapted to monitor the position other devices which are configured for implantation inside a patients body.

Figure 18A:
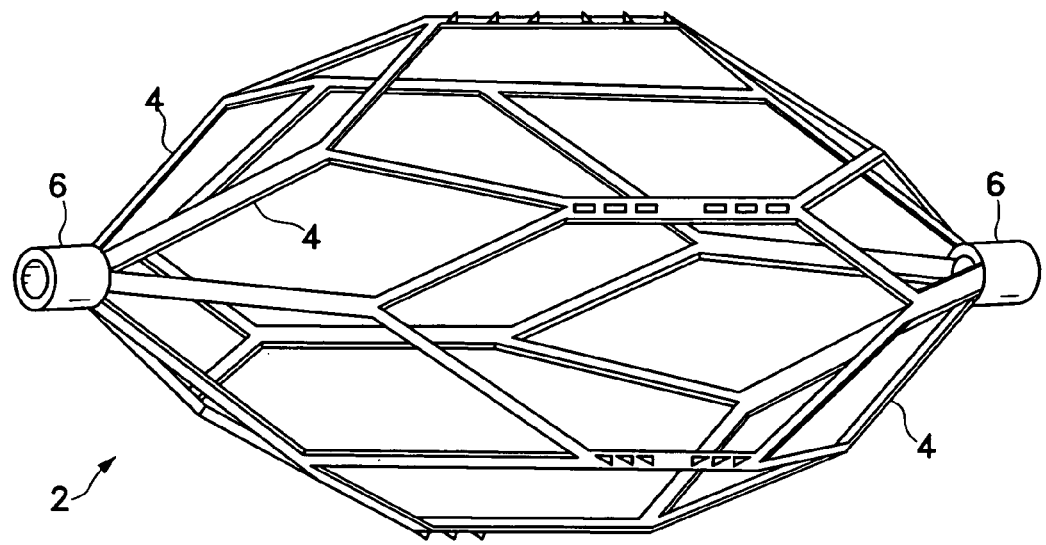
FIGS. 18A-18D illustrate examples of vessel filters that may be adapted with electronic measurement circuits
Figure 18B:
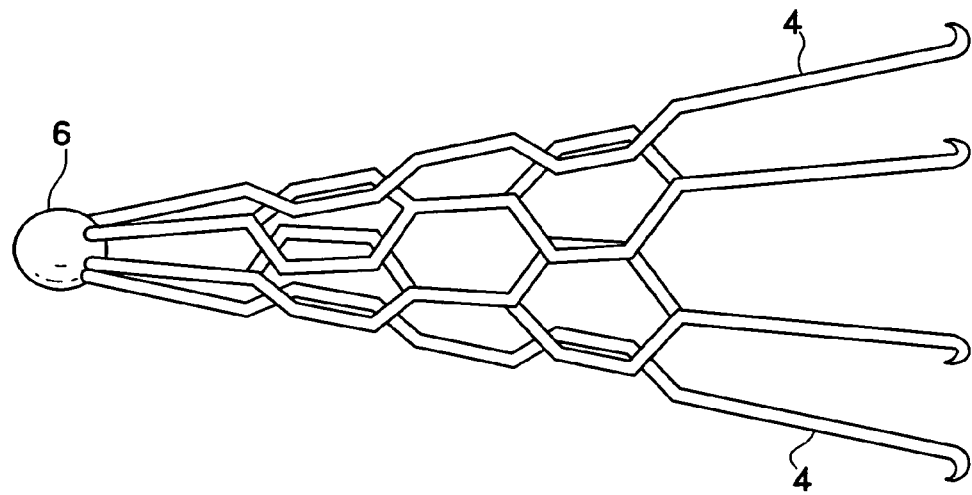
Figure 18C:
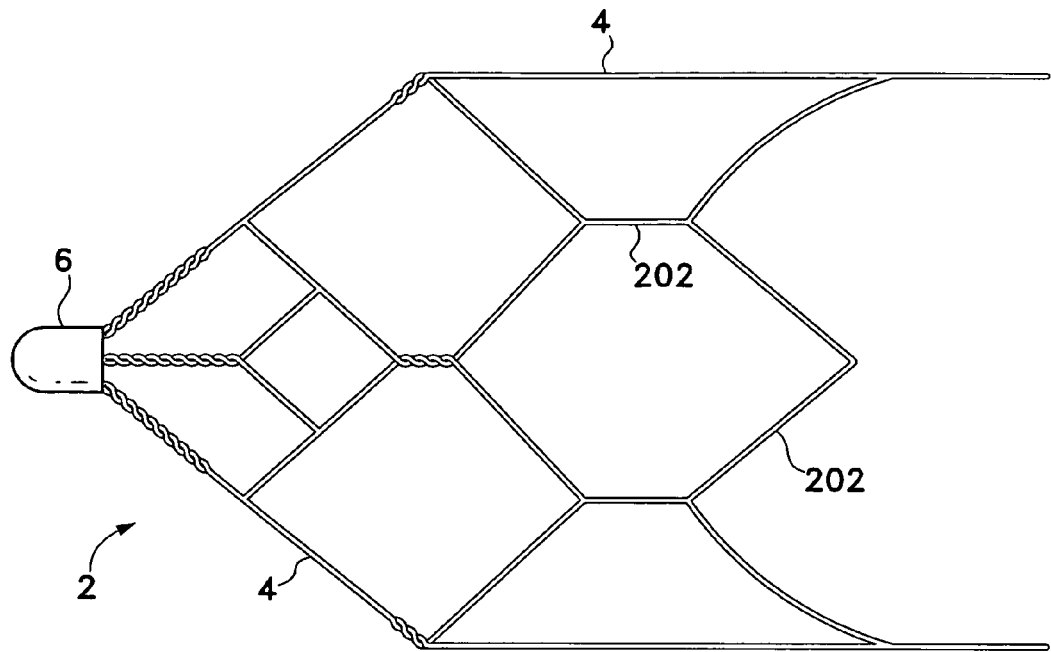
Figure 18D:
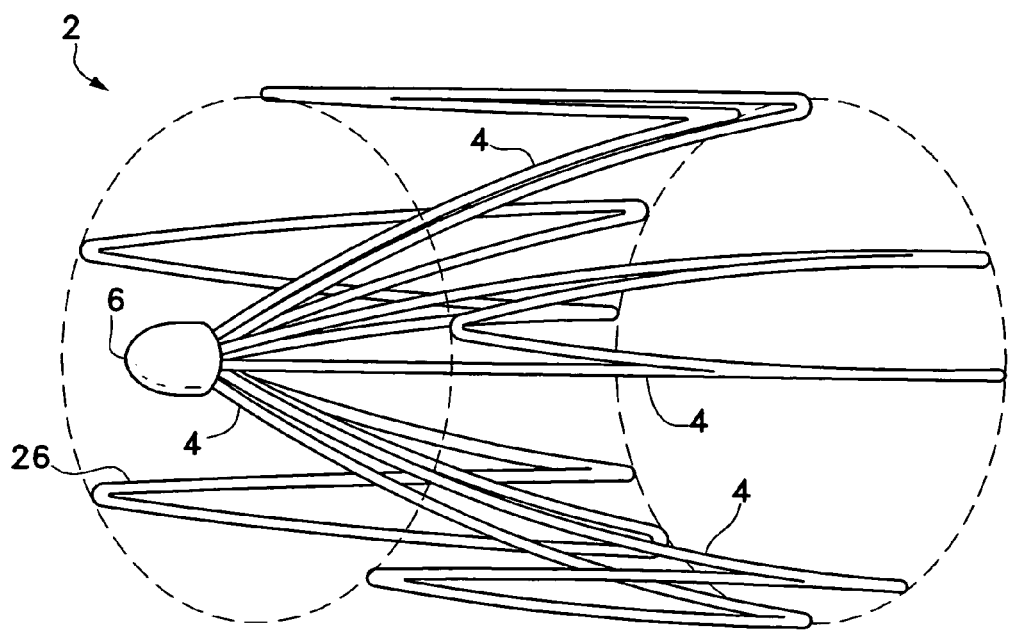

One of ordinary skill in the art having the benefit of this disclosure would appreciate that the electronic measurement circuit may be implemented on various vessel filters designs. Examples of vessel filters that may be adapted with electronic measurement circuits are illustrated in FIGS. 18A, 18B, 18C, and 18D. In FIG. 18A, the vessel filter 2 comprises two sleeves 6, where each sleeve 6 is configured to couple a plurality of appendages 4. The appendages 4 are interlinked to form an expendable filter. An electronic measurement circuit may be positioned in one or both of the sleeves to measure the strain on one or more of the appendages. Portion of the interconnecting links of the vessel filter appendages may comprise non-conductive material such that electric conductive loops may be formed to measure the strain on one or more of the appendages. Alternatively, sensors, which are connected to an electronic measurement circuit, may be attached to one or more of the appendages to measure a parameter on the appendages. FIG. 18B shows a vessel filter 2 with jagged leg 4 configuration. An electronic measurement circuit may be positioned in the sleeve 6 to measure a parameter of one or more of said legs 4. Alternatively, the electronic measurement circuit may be attached to one or more of the legs. FIG. 18C illustrates another variation of a vessel filter 2 with multiple interlinks 202. A measurement circuit may be implemented either in the sleeve 6, attached to the sleeve 6, or attached to one or more of the legs. The electronic measurement circuit may be adapted to measure the strain on the legs 4 and/or interlinks 202. In yet another design, the vessel filter 2 is configured with a reverse loop 26 extending from each pair of legs 4 as show in FIG. 18D. Each pair of legs 4 and their corresponding reverse loop 26 may form a complete circuit loop, and an electronic measurement circuit positioned on or within the sleeve of the vessel filter may be connected to the pair of legs to measure the strain in each pair of legs. One of ordinary skill in the art having the benefit of this disclosure would appreciate that the electronic measurement circuit may be implemented on these filters with other electronic configurations.

In addition, one of ordinary skill in the art having the benefit of this disclosure would also appreciate that the electronic measurement circuit is not limited to implementation for measuring strain on the legs of a vessel filter. The electronic measurement circuit, which may be a passive circuit, may be adapted to measure strain and/or other parameters on various portions or structures on a vessel filter.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed as new and desired to be protected by Letters Patent of the United States is:

1. An implantable particle capturing device comprising:
   a vessel filter adapted for implantation into a body vessel, including a plurality of elongated appendages with proximal ends and free distal ends;
   a sleeve enclosing the proximal ends of the elongated appendages;
   a hub connected to the sleeve by a spring, the spring maintaining a first distance between the hub and the sleeve in an unstressed state and a second distance less than the first distance between the hub and the sleeve in a stressed state, the stressed state created by application of an external force;

a sensing member coupled to the hub and movably displaceable with respect to the sleeve; and an electronic circuit between the hub and the sleeve, measuring a displacement therebetween.

2. The implantable particle capturing device according to claim 1, wherein said electronic circuit measures a strain.

3. The implantable particle capturing device according to claim 2, wherein said electronic circuit is configured to transmit information regarding said strain to a remote monitor.

4. The implantable particle capturing device according to claim 2, wherein said electronic circuit is configured to transmit information regarding a distribution of said strain on said vessel filter to a remote monitor.

5. The implantable particle capturing device according to claim 1, wherein said electronic circuit is configured to transmit information regarding a parameter to a remote monitor.

6. The implantable particle capturing device according to claim 5, wherein said electronic circuit comprises a passive electronic circuit.

7. The implantable particle capturing device according to claim 1, wherein the electronic circuit is within the sleeve.

8. The implantable particle capturing device according to claim 1, further comprising a strain gauge coupled to the hub, wherein the electronic circuit measures the strain gauge.

9. The implantable particle capturing device according to claim 1, further comprising a strain gauge coupled between the sensing member and a second sensing member coupled to the hub, wherein the electronic circuit measures the strain gauge.

10. The implantable particle capturing device according to claim 1, further comprising a microelectromechanical sensor coupled to the sensing member.

11. The implantable particle capturing device according to claim 10, wherein the microelectromechanical sensor detects a movement of the sensing member.

12. The implantable particle capturing device according to claim 1, wherein the sensing member is looped to complete the electronic circuit.

13. The implantable particle capturing device according to claim 1, wherein the hub is movably displaceable inside the sleeve.

14. The implantable particle capturing device according to claim 13, wherein the hub is movably displaceable with respect to the sleeve along a longitudinal axis of the implantable particle capturing device.

15. The implantable particle capturing device according to claim 1, wherein the spring biases the hub away from the sleeve during use, and is compressed when an object contacts the sensing member.

* * * * *